United States Patent [19]

Carruthers et al.

[11] Patent Number: 5,654,316

[45] Date of Patent: Aug. 5, 1997

[54] PIPERIDINE DERIVATIVES AS NEUROKININ ANTAGONISTS

[75] Inventors: Nicholas I. Carruthers, N. Plainfield; Cheryl A. Alaimo, Somerset, both of N.J.

[73] Assignee: Schering Corporation, Kenilworth, N.J.

[21] Appl. No.: 466,551

[22] Filed: Jun. 6, 1995

[51] Int. Cl.$^6$ .......................... A61K 31/47; C07D 401/12
[52] U.S. Cl. .................. 514/307; 514/314; 514/327; 514/329; 514/331; 514/227.8; 514/232.5; 544/62; 544/128
[58] Field of Search .................... 514/307, 314, 514/327, 329, 331; 546/146, 165, 217, 221, 224, 234

[56] References Cited

U.S. PATENT DOCUMENTS

| | | |
|---|---|---|
| 5,350,852 | 9/1994 | Emonds-Alt et al. . |
| 5,387,595 | 2/1995 | Mills . |
| 5,411,971 | 5/1995 | Emonds-Alt . |
| 5,434,158 | 7/1995 | Shah . |

FOREIGN PATENT DOCUMENTS

| | | |
|---|---|---|
| 0428434 | 5/1991 | European Pat. Off. . |
| 0474561 | 3/1992 | European Pat. Off. . |
| 0518805 | 12/1992 | European Pat. Off. . |
| 0655442 | 5/1995 | European Pat. Off. . |
| 2696178 | 9/1992 | France . |
| 9413694 | 6/1994 | WIPO . |
| 9429309 | 12/1994 | WIPO . |

*Primary Examiner*—Jacqueline Haley
*Attorney, Agent, or Firm*—John Blasdale; Matthew Boxer

[57] ABSTRACT

The invention relates to compounds of the formula

I wherein X, i, j, n, n', A, A', $R_2$, $R_3$, and U are as described herein. The compounds of the invention are $NK_1$ or $NK_2$ or $NK_3$ receptor antagonists and as such are useful in the treatment of diseases such as asthma.

24 Claims, No Drawings

PIPERIDINE DERIVATIVES AS NEUROKININ ANTAGONISTS

BACKGROUND OF THE INVENTION

The present invention relates to a genus of compounds useful as antagonists of neurokinin receptors. In particular, these can be neurokinin-1 receptor ($NK_1$) antagonists, neurokinin-2 receptor ($NK_2$) antagonists, and neurokinin-3 receptor ($NK_3$) antagonists.

Neurokinin receptors are found in the nervous system and the circulatory system and peripheral tissues of mammals, and therefore are involved in a variety of biological processes. Neurokinin receptor antagonists are consequently expected to be useful in the treatment or prevention of various mammalian disease states, for example asthma, cough, bronchospasm, inflammatory diseases such as arthritis, migraine, nociception, and various gastrointestinal disorders such as Crohn's disease.

In particular, $NK_1$ receptors have been reported to be involved in microvascular leakage and mucus secretion, and $NK_2$ receptors have been associated with smooth muscle contraction, making $NK_1$ and $NK_2$ receptor antagonists especially useful in the treatment and prevention of asthma.

SUMMARY OF THE INVENTION

The invention relates to compounds of the formula

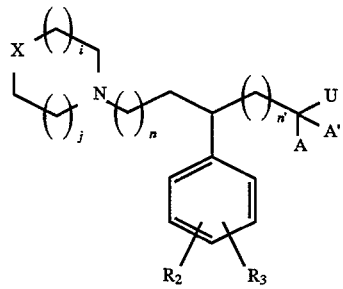

I wherein each i and j is independently selected from the group consisting of 1 and 2;

each n is independently selected from the group consisting of 0, 1, 2 and 3; and each n' is independently selected from the group consisting of 1, 2 and 3;

wherein A and A' are H, or A and A' taken together are =O, =S; or =N—$R_4$;

X is selected from the group consisting O, CO, C(R, $R_1$), C=C($R_1,R_8$), $NR_1$, and $S(O)_e$ wherein e is 0, 1, or 2;

R is selected from the group consisting of H, $OR_8$, $CON(R_8)_2$, CN, $S(O)_eR_8$, $SO_eN(R_8)_2$, $CO_2R_8$, and $NR_4COR_8$;

$R_1$ is selected from the group consisting of H, ($C_1-C_6$)-alkyl ($C_3-C_8$)-cyclo-alkyl, 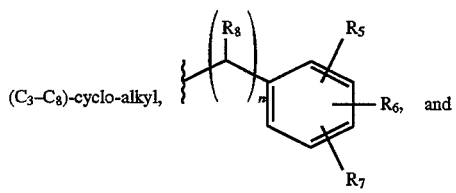 and

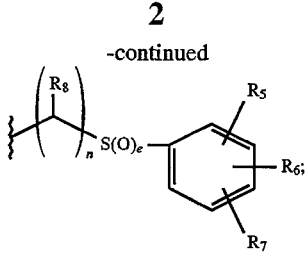

$R_2$, $R_3$, $R_5$, $R_6$ and $R_7$ are independently selected from the group consisting of H, halogen, ($C_1-C_6$)-alkyl, $CF_3$, $C_2F_5$, $OR_8$, $COR_8$, $CO_2R_8$, $CON(R_8, R_8)$, $N(R_8, R_8)$, $N(R_8)COR_8$, $S(O)_eR_8$, $OC(O)R_4$, $OC(O)N(R_8, R_4)$, $NR_8CO_2R_4$, $NR_8(CO)N(R_8,R_8)$, $R_{15}$-phenyl, $R_{15}$-benzyl, $NO_2$, $NR_8SO_2R_4$, —$S(O)_2N(R_8)_2$ or when $R_2$ and $R_3$ or any two of $R_5$, $R_6$ and $R_7$ are on adjacent carbons they may form a —O—$CH_2$—O— group;

each $R_4$ is independently selected from the group consisting of alkyl, substituted alkyl, substituted aryl, and substituted benzyl;

each $R_8$ is independently selected from the group consisting of H, alkyl, substituted alkyl, substituted aryl, and substituted benzyl;

each $R_{15}$ is independently H, halogen, lower alkyl, lower alkoxy; and

U is

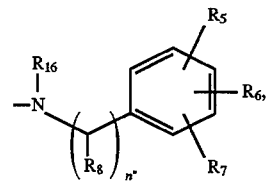 (A)

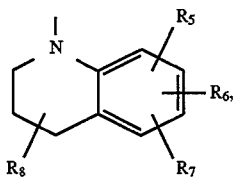 (B)

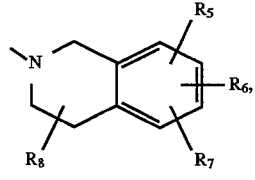 (C)

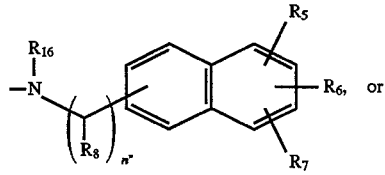 (D)

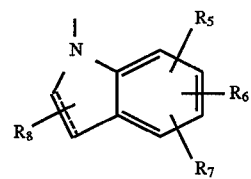 (E)

n" is independently selected from the group consisting of 0, 1, 2 and 3;

the dashed line is an optional carbon-carbon bond;

$R_{16}$ is H, $(C_1-C_6)$-alkyl, $-S(O)_2R_4$, $COR_8$, $CO_2R_4$, $CON(R_8)_2$, $R_{15}$-phenyl or $R_{15}$-benzyl.

Substituted means substituted with a substituent selected from the group consisting of H, $(C_1-C_6)$ alkyl, $OCF_3$, $CF_3$, and $C_2F_5$.

Also preferred are compounds of formula I, wherein i is 1 and j is 1.

Also preferred are compounds of formula I, wherein n is 1, n" is 0, 1, or 2, and n' is 1.

Also preferred are compounds of formula I, wherein n, n' and n" are all 1.

Also preferred are compounds of formula I, wherein n and n' are both 1 and n" is 0.

Also preferred are compounds of formula I, wherein n and n' are both 1 and n" is 2.

Also preferred are compounds of formula I, wherein A and A' are both H

Also preferred are compounds of formula I, wherein A and A' taken together are =O.

Also preferred are compounds of formula I, wherein X is $C(R, R_1)$.

Also preferred are compounds of formula I, wherein R is $OR_8$, $CON(R_8)_2$, CN, or $NR_8COR_8$.

Also preferred are compounds of formula I, wherein X is $NR_1$.

Also preferred are compounds of formula I, wherein $R_1$ is

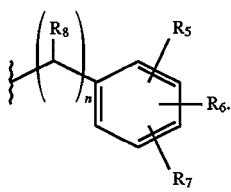

Also preferred are compounds of formula I, where n is 0 or 1 and $R_8$ is H.

Also preferred are compounds of formula I, wherein $R_2$, $R_3$, $R_5$, $R_6$ and $R_7$ are H, halogen, $C_1-C_6$ alkyl, $CF_3$, $OR_8$, $COR_8$, $CO_2R_8$, $CONR_8,R_8$, or $NR_8,R_8$ Also preferred are compounds of formula I, wherein $R_{16}$ is H or alkyl.

Also preferred are compounds of formula I, wherein each $R_8$ is H, $C_1-C_6$ alkyl, or $R_{15}$-phenyl Also preferred are compounds of formula I, wherein $R_8$ is H or substituted alkyl.

Also preferred are compounds of formula I, wherein U is

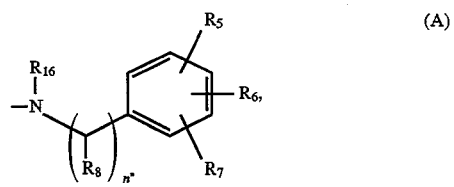 (A)

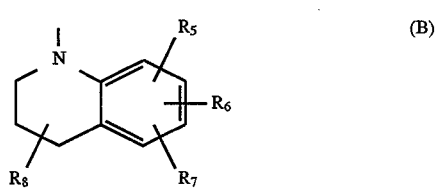 (B)

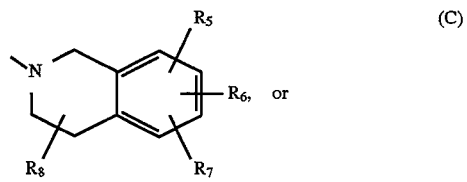 (C), or

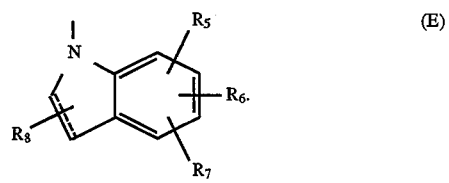 (E)

Exemplary compounds of the invention are:

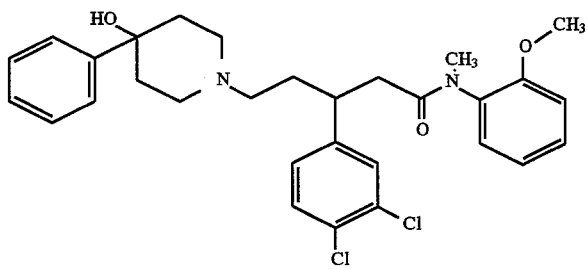

-continued
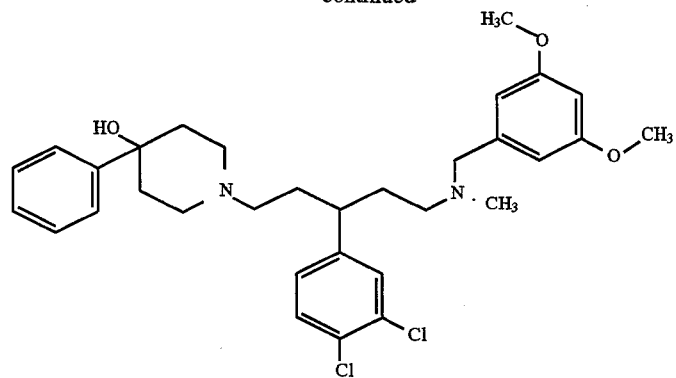
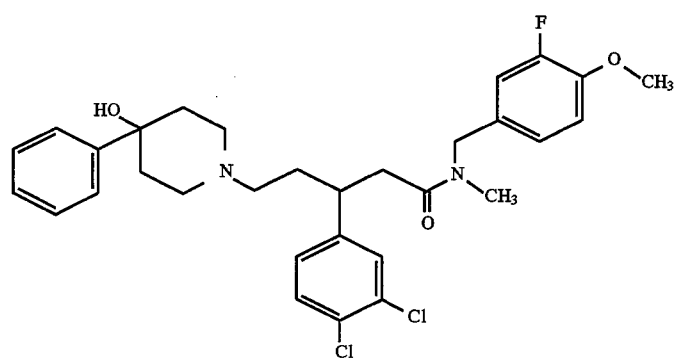
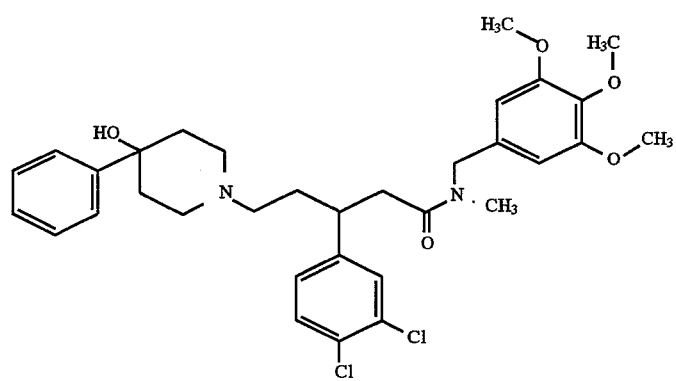
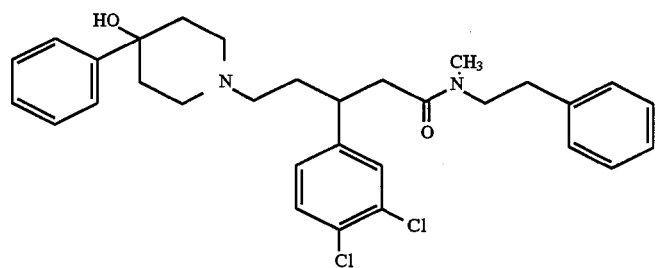
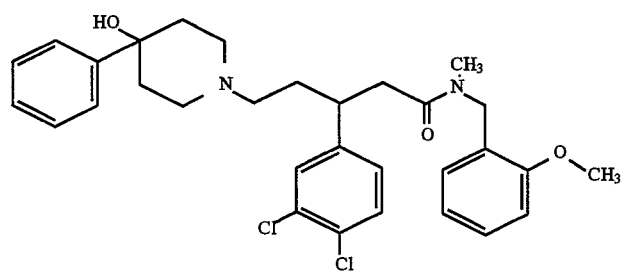

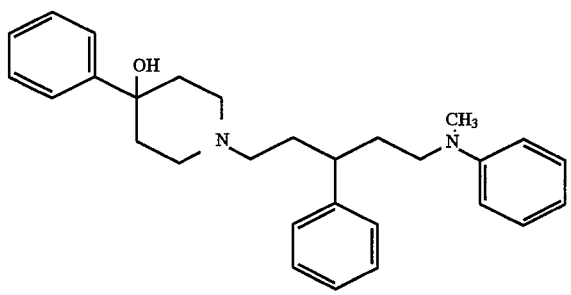
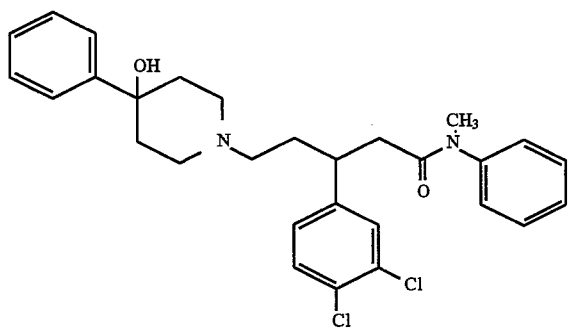
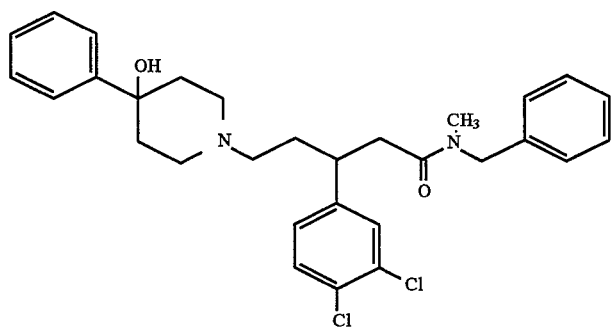
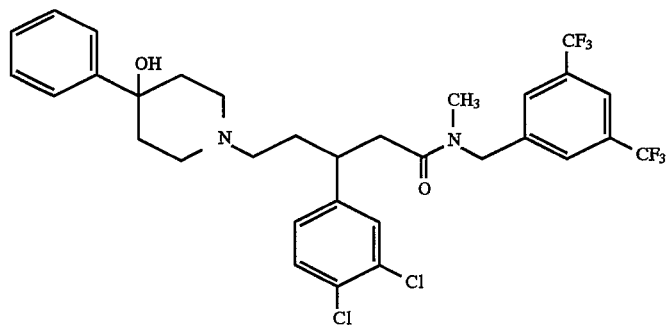
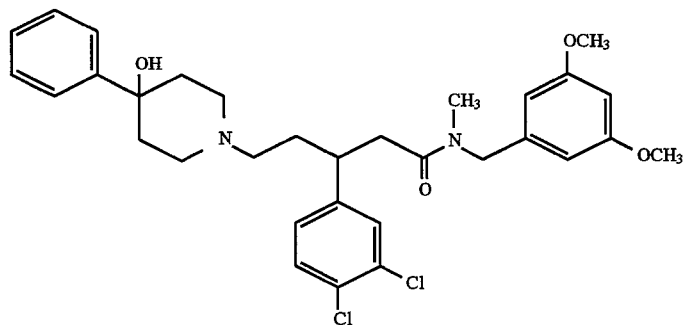

-continued
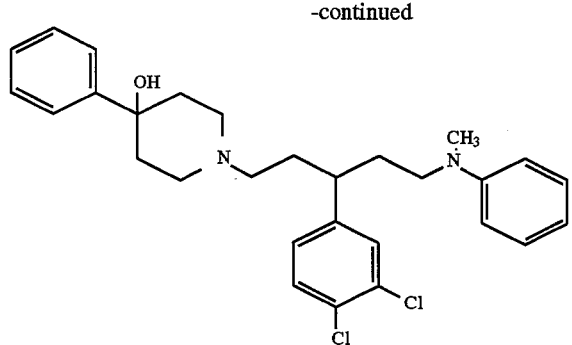
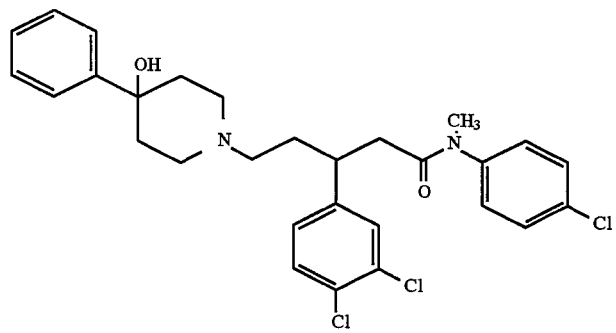
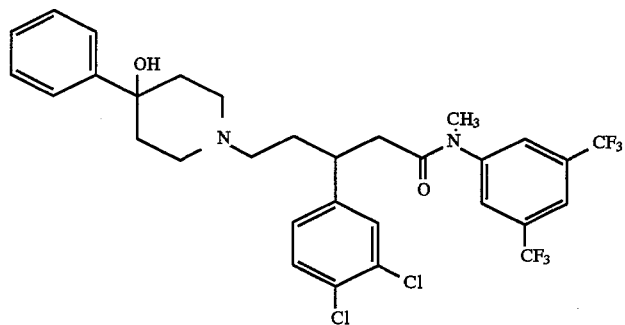
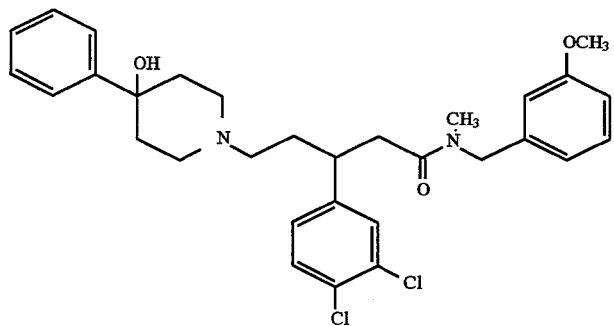
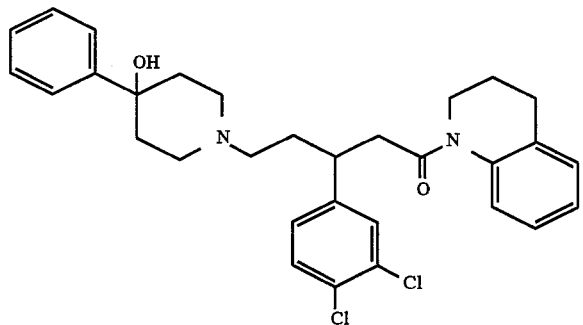

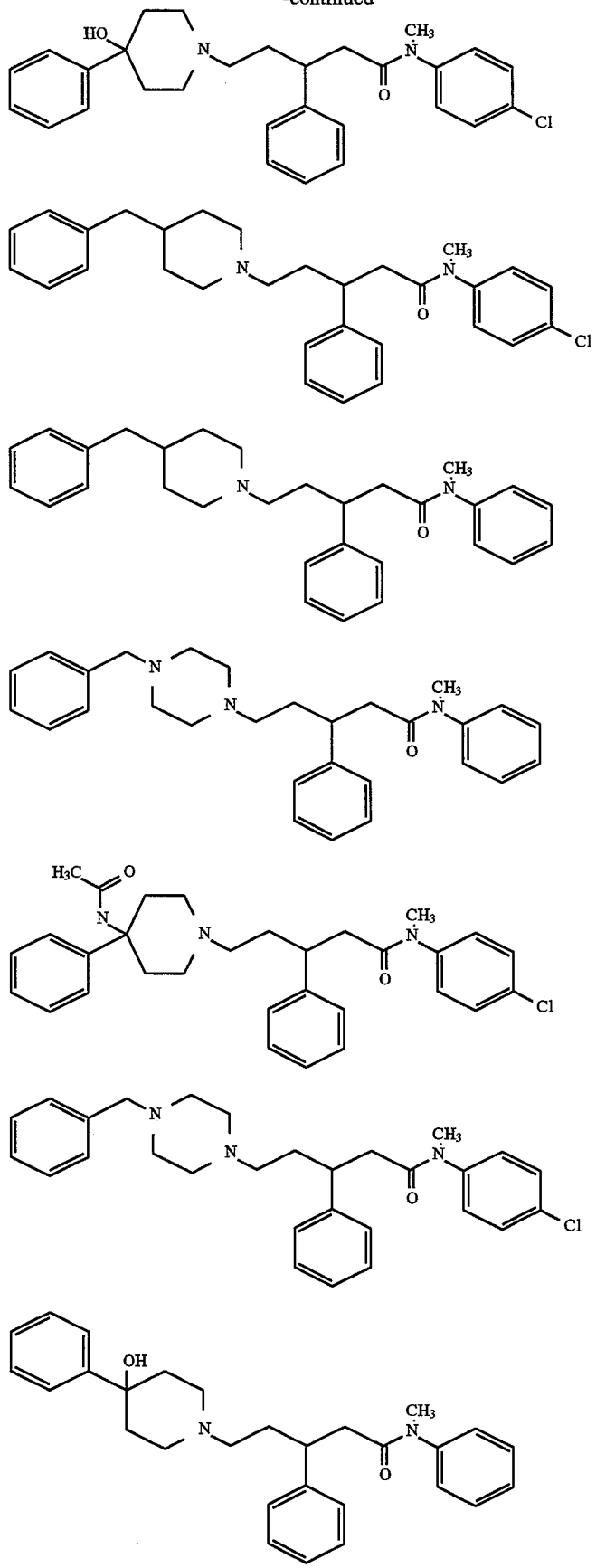

-continued
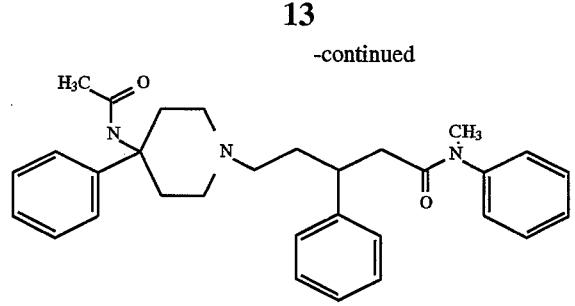
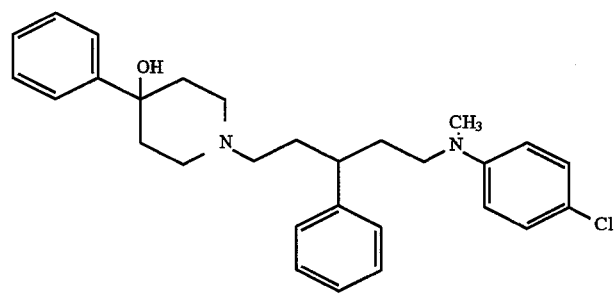
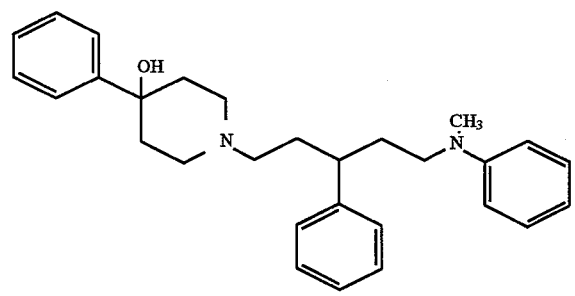
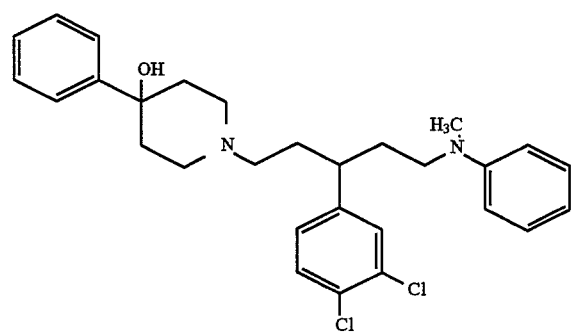
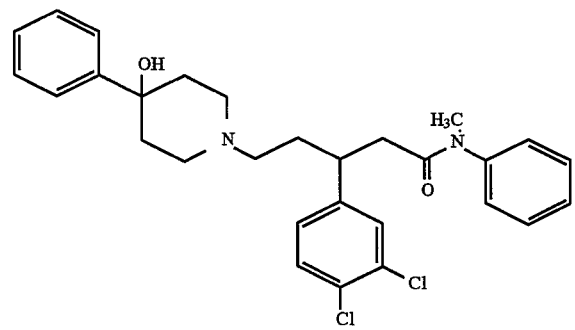

-continued
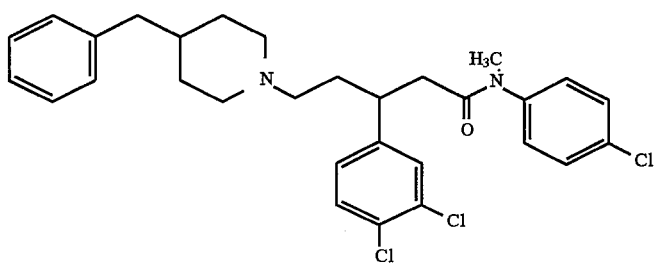
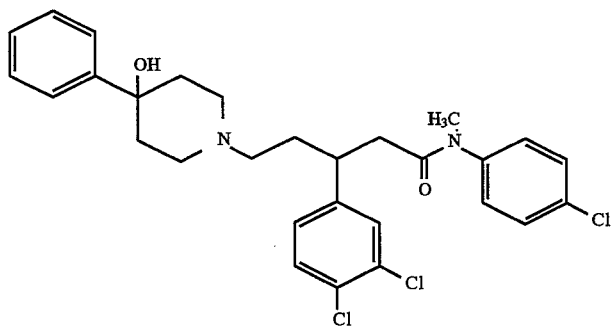
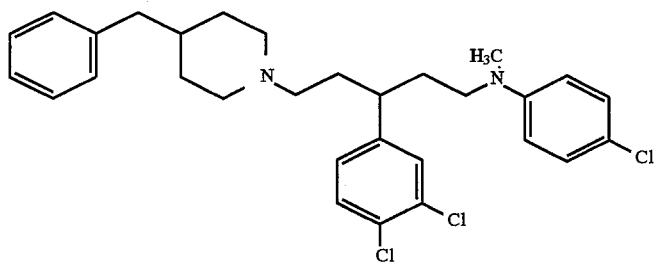
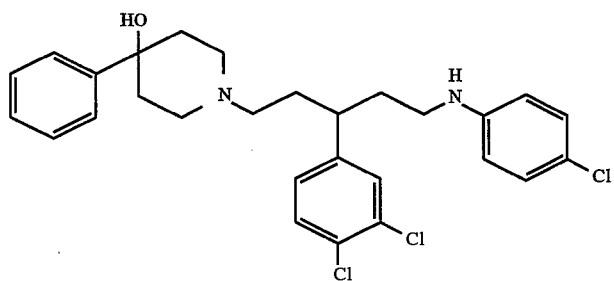
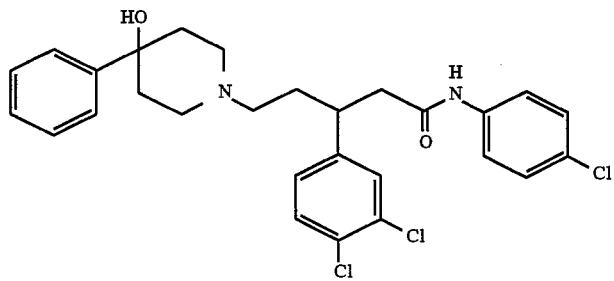

-continued
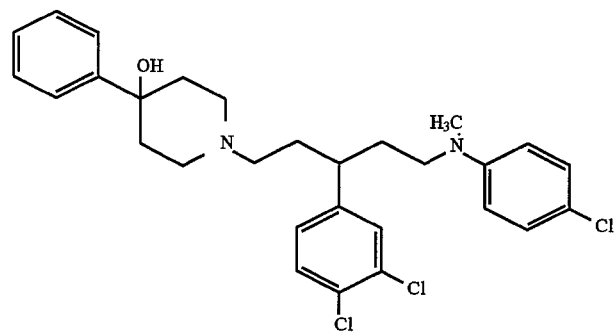
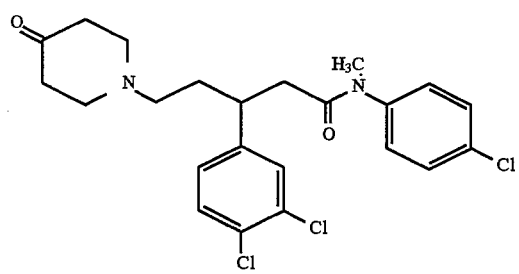
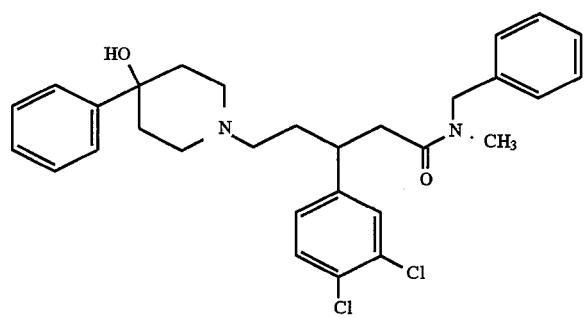
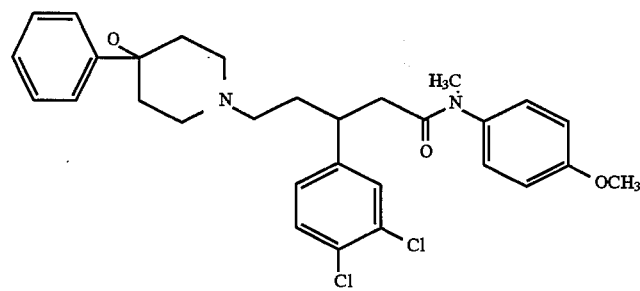
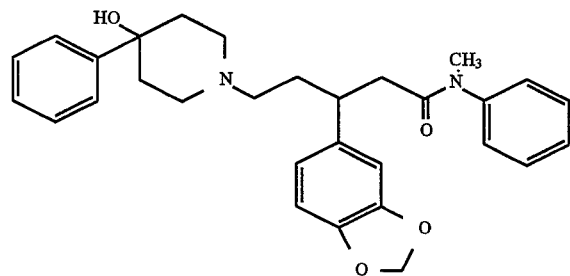

-continued
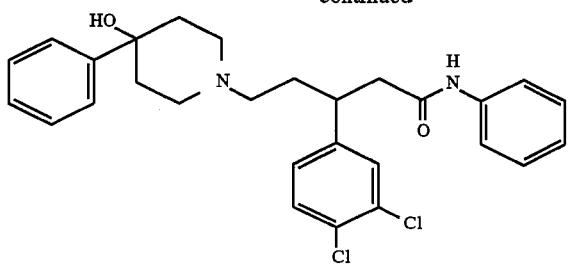
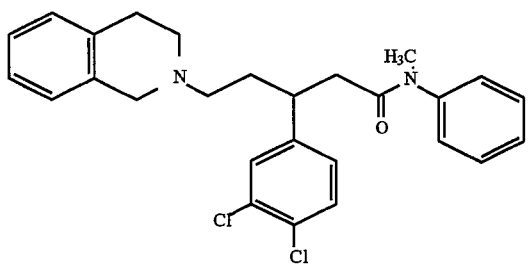
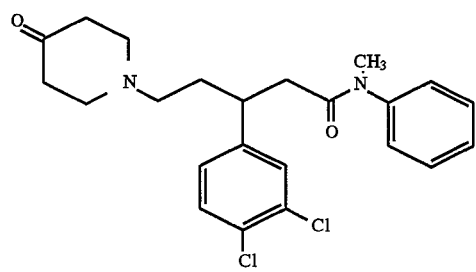
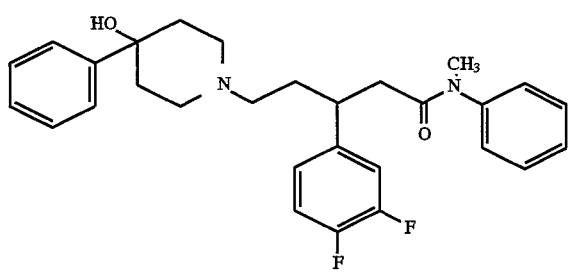
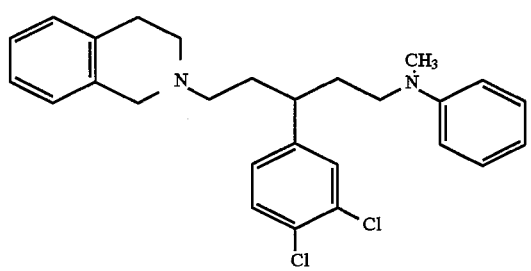
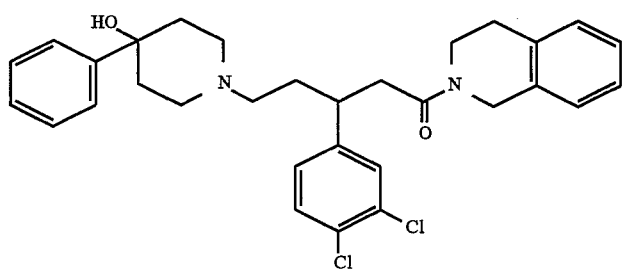

-continued
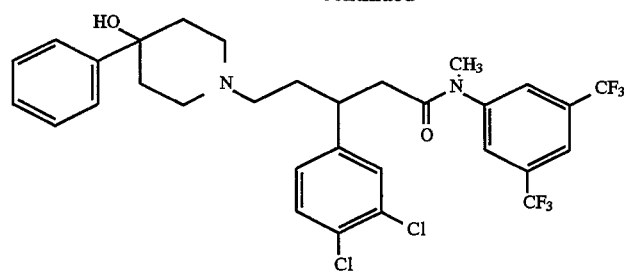
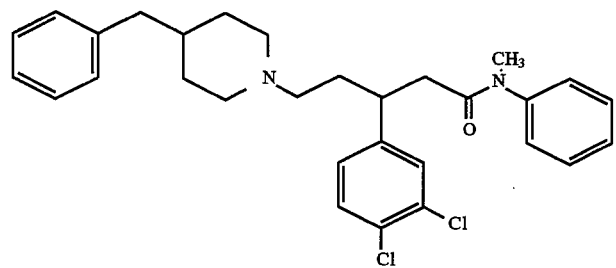
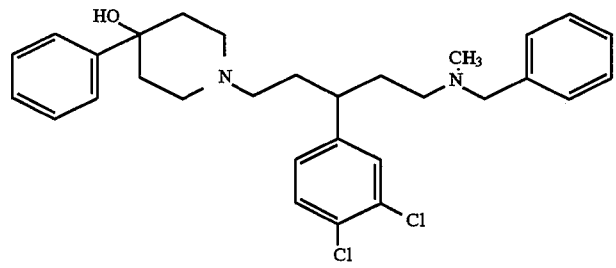
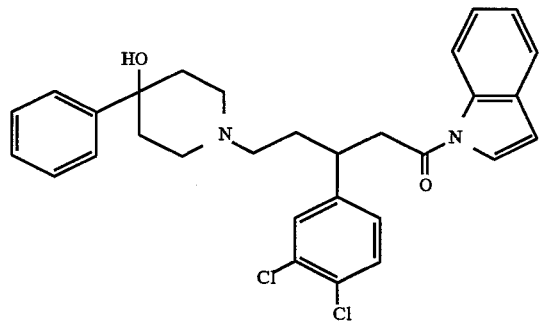
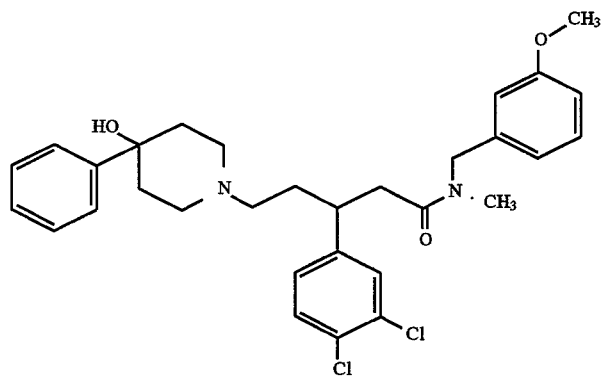

-continued
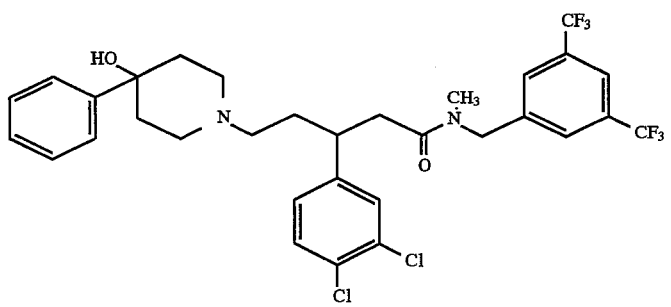
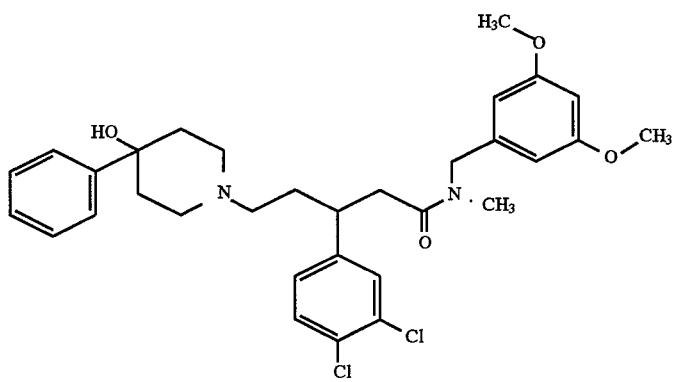
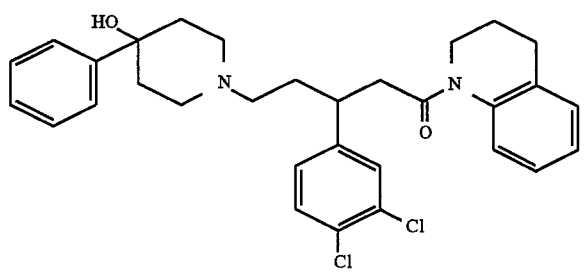
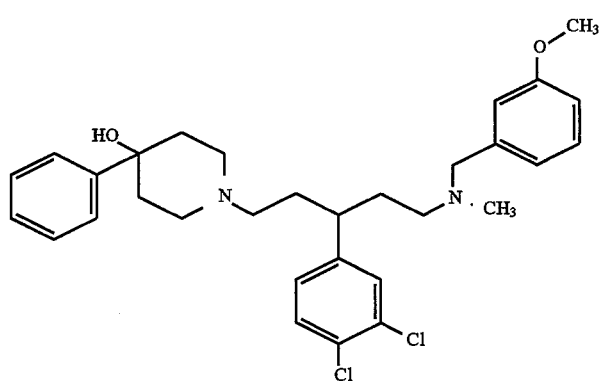
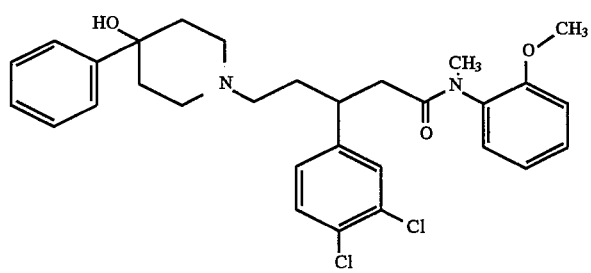

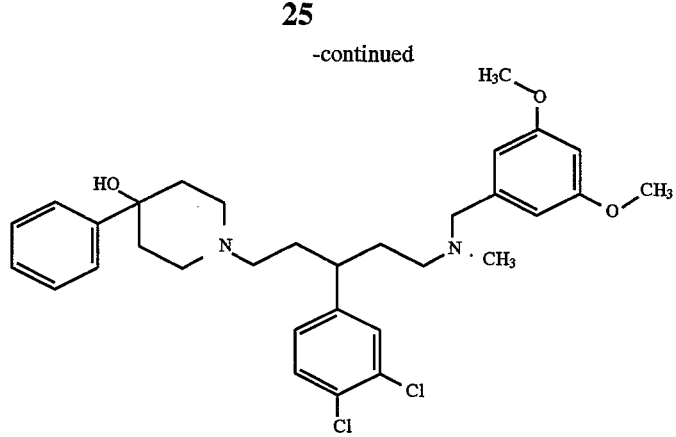
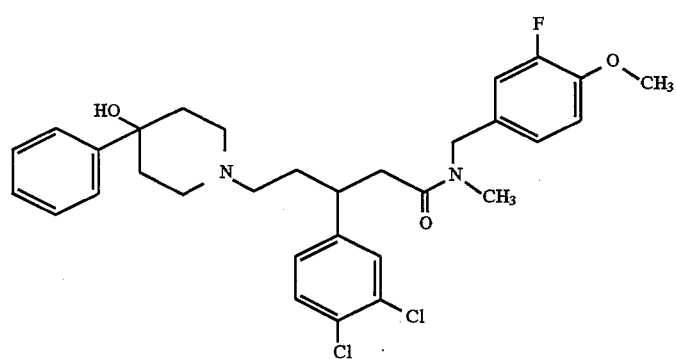
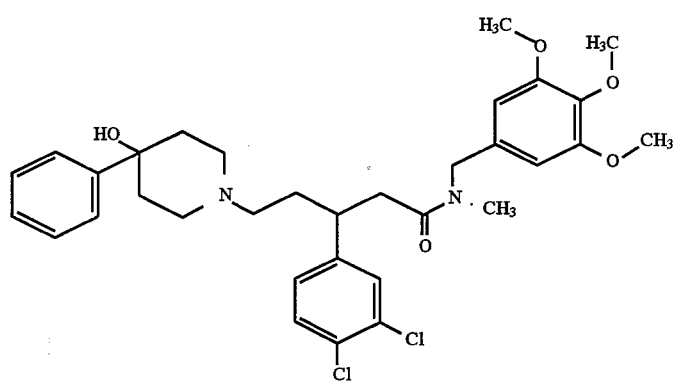
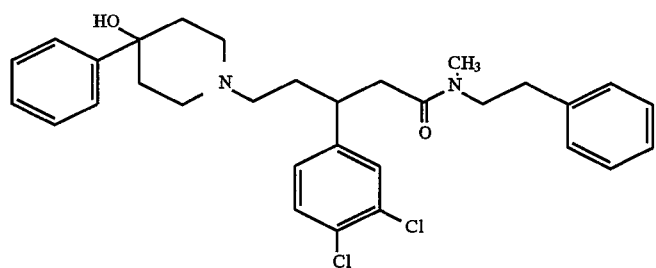
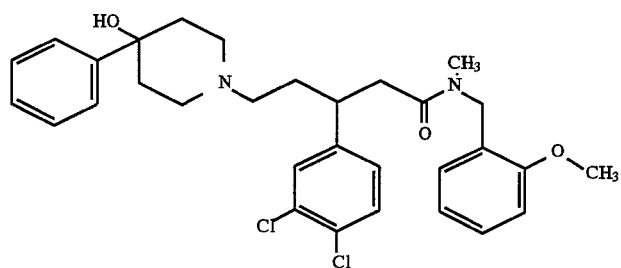

The invention also relates to a composition comprising a neurokinin antagonistic effective amount of a compound according to formula I and a pharmaceutically acceptable carrier material.

The invention also relates to a method for inducing neurokinin antagonism which comprises administering a neurokinin antagonistic effective amount of a compound according to formula I to a mammal in need thereof.

The invention also relates to a pharmaceutical composition comprising a therapeutically effective amount of a compound of formula I in combination with a pharmaceutically acceptable carrier.

The invention also relates to a method for treating chronic airway diseases such as asthma and allergies; inflammatory diseases such as inflammatory bowel disease, psoriasis, osteoarthritis, and rheumatoid arthritis; migraine; central nervous system disorders such as depression, psychosis, dementia, and Alzheimer's disease; Down's syndrome; neuropathy; multiple sclerosis; ophthalmic disorders; conjunctivitis; auto immune disorders; graft rejection; systemic lupus erythematosus; GI disorders such as Crohn's disease and ulcerative colitis; disorders of bladder function; circulatory disorders such as angina; Raynaud's disease; coughing and pain. In particular, the invention also relates to a method of treating asthma which comprises administering to a mammal in need of such treatment an anti-asthma effective amount of a compound of formula I for such purpose.

DETAILED DESCRIPTION OF THE INVENTION

As used herein the term alkyl means a straight or branched, saturated hydrocarbon chain having from 1 to 6 carbon atoms. The number of carbon atoms may be designated. For example, "$C_1$–$C_6$ alkyl" represents a straight or branched, saturated hydrocarbon having from 1 to 6 carbon atoms.

The term alkenyl means means a straight or branched, saturated alkenyl having from 2 to 6 carbon atoms. The number of carbon atoms may be designated. For example, "$C_2$–$C_6$ alkenyl" represents a straight or branched alkenyl having from 1 to 6 carbon atoms.

Asymmetric centers exist in compounds of formula I of the invention. Accordingly, compounds of formula I include stereoisomers.

All such isomeric forms and mixtures thereof are within the scope of the present invention. Unless otherwise indicated, the methods of preparation disclosed herein may result in product distributions which include all possible structural isomers, although it is understood that physiological response may vary according to stereochemical structure. The isomers may be separated by conventional means such as fractional crystallization, preparative plate or column chromatography on silica, alumina, or reversed phase supports or HPLC (high performance liquid chromatography).

Enantiomers may be separated, where appropriate, by derivatization or salt formation with an optically pure reagent, followed by separation by one of the aforementioned methods. Alternatively, enantiomers may be separated by chromatography on a chiral support.

The compounds of formula I can exist in unsolvated as well as solvated forms, including hydrated forms, e.g. the hemihydrate. In general, the solvated forms, with pharmaceutically acceptable solvents such as water, ethanol, and the like are equivalent to the unsolvated forms for the purposes of the invention.

Those compounds of formula I which contain a basic group such as —$CH_2NH_2$, form pharmaceutically acceptable salts. The preferred pharmaceutically acceptable salts are nontoxic acid addition salts formed by adding to a suitable compound of the invention about a stoichiometric amount of a mineral acid, such as HCl, HBr, $H_2SO_4$ or $H_3PO_4$ or of an organic acid such as acetic, propionic, valeric, oleic, palmitic, stearic, lauric, benzoic, lactic, paratoluenesulfonic, methane sulfonic, citric, maleic, fumaric, succinic and the like, respectively.

GENERAL METHODS OF PREPARATION

The compounds of this invention may be prepared by one of the following general methods. Unless otherwise indicated, variables in the structural formulas below are as defined above.

The compounds of the present invention may be prepared from an appropriately substituted benzaldehyde as shown in Scheme 1 or from an appropriately substituted phenylacetic acid as shown in Scheme 2.

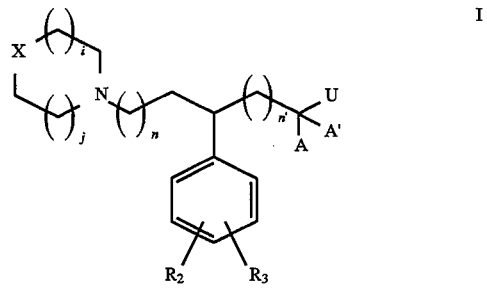

Methods for preparing the compounds of the present invention are illustrated in the following Schemes and examples. The compounds of the present invention may be prepared from an appropriately substituted benzaldehyde as shown in Scheme 1 or from an appropriately substituted phenylacetic acid as shown in Scheme 2.

Thus, as shown in Scheme 1, a benzaldehyde A is condensed with ethylacetoacetate in the presence of a base, for example an amine base such as piperidine, in a suitable solvent, for example an alcohol such as ethanol, as described in *J. Indian Chem. Soc.*, 1976, 53, 1122, to give a bisacetoacetate B. Hydrolysis of B under strongly basic conditions using sodium hydroxide in an aqueous alcoholic solvent gives diacid C. Dehydration of C using an appropriate dehydrating agent, for example dicyclohexylcarbodiimide or acetyl chloride, then gives the substituted glutaric anhydride D. Treatment of anhydride D with an aniline or an arylalkylamine E in a suitable solvent, for example a halogenated solvent such as dichloromethane, in the presence of a suitable base, for example triethylamine or N,N-dimethylaminopyridine, gives acid F. Reduction of the carboxylic acid function of F using a suitable reduction procedure, for example via the corresponding imidazolide or carbonic mixed anhydride and treatment with aqueous sodium borohydride, gives alcohol G. The alcohol G may then be converted to its corresponding halide or sulfonate H, for example by treatment with a sulfonyl halide in the presence of a base such as pyridine. Intermediate H may then be condensed with heterocyclic amine I in a suitable solvent, for example N,N-dimethylformamide, in the presence of a base, for example potassium carbonate or N,N-diisopropylethylamine, if desired to give J. In an alternative embodiment alcohol G may be oxidized, for example by the Swern procedure as described in *Tetrahedron*, 1978, 34, 1651, to give aldehyde K. Aldehyde K may then be condensed with heterocyclic amine I in a reductive amination reaction, for example using sodium cyanoborohydride in methanol in the presence of a dehydrating agent such as molecular sieves, similar to that described in *J. Amer. Chem. Soc.*, 1971, 93, 2897, to give J. The amide functionality of J may be reduced, for example using borane-dimethylsulfide in tetrahydrofuran, to give amine L.

Scheme 1.

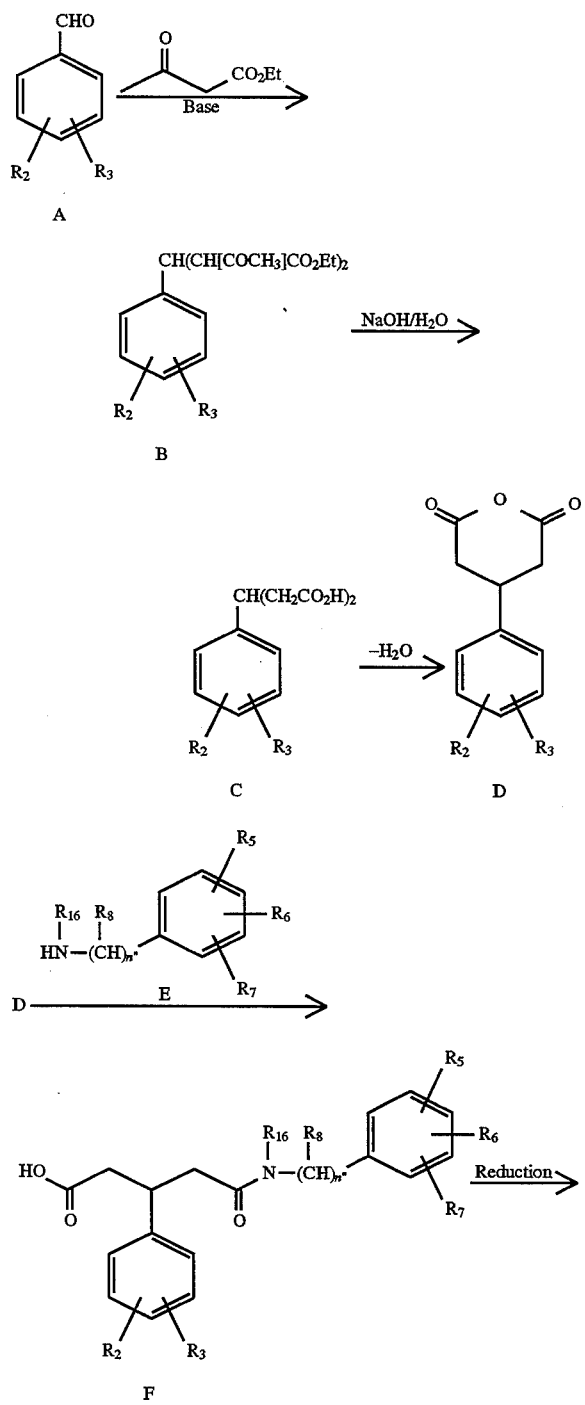

-continued
Scheme 1.

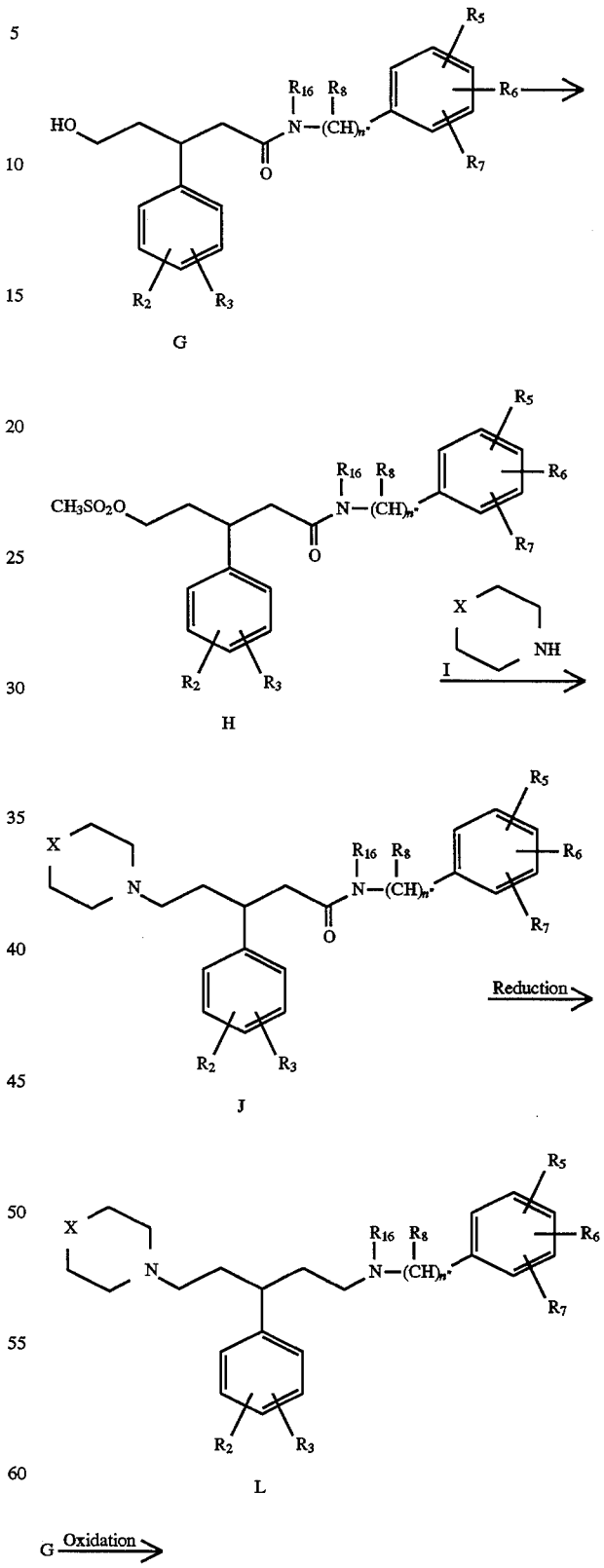

31
-continued
Scheme 1.

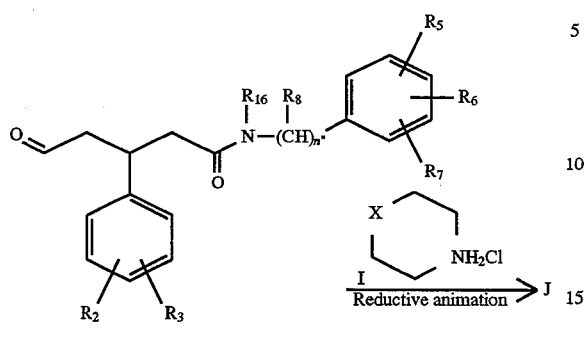

K

In an alternative synthesis, Scheme 2, a phenylacetic acid M may be converted to allyl acid N, for example as described in *Bioorganic Med. Chem. Letts.*, 1993, 3, 319. Acid N may be homologated to acid P according to the Arndt-Eistert procedure, for example as described in *Chem. Pharm. Bull.*, 1981, 29, 3249, and acid P may be condensed with an aniline or arylalkylamine E to give O (n=1). Condensation of acid P may be accomplished via the corresponding acid chloride, prepared from P by treatment with oxalyl chloride and catalytic N,N-dimethylformamide, which may be used when E is an aniline or an arylalkylamine and is the preferred method when E represents an aniline. In an alternative procedure, when E is an arylalkylamine, condensation with P may be effected via the use of a carbodiimide, for example by the use of 1-ethyl-3-(3-dimethylaminopropyl)carbodiimide in dichloromethane. The allyl group of O can be oxidatively cleaved, for example upon treatment with ozone in methanol, to give aldehyde K. Aldehyde K may then be used in reductive amination reactions with heterocyclic amines I to give compound J as illustrated in Scheme 1.

Scheme 2.

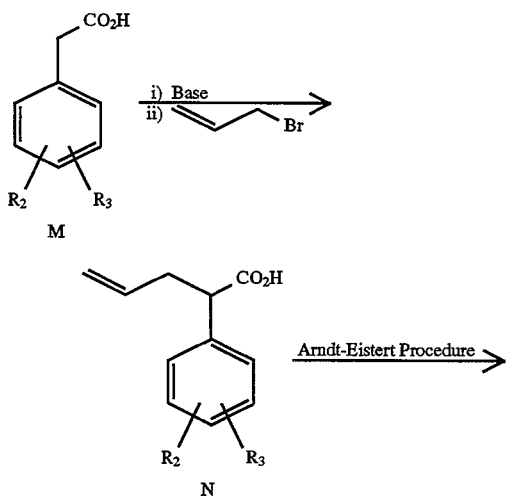

32
-continued
Scheme 2.

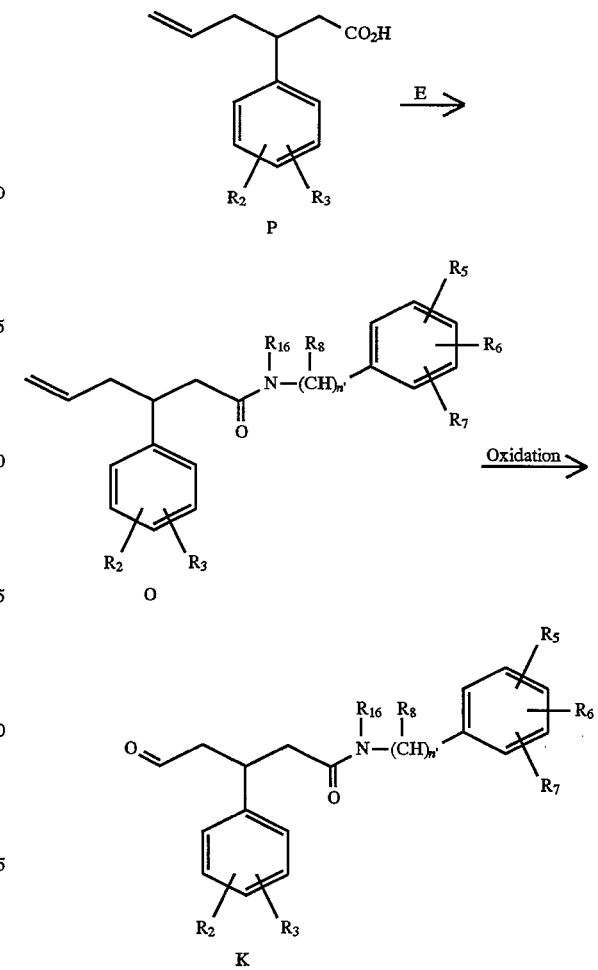

The invention disclosed herein is examplified by the following examples, which should not be construed to limit the scope of the disclosure. Alternative mechanistic pathways and analogous structures within the scope of the invention will be apparent to those skilled in the art.

EXAMPLE 1

Beta-(3,4-Dichlorophenyl)-4-hydroxy-N-methyl-N,4-diphenyl-1-piperidinepentamide

Step A

Diethyl-3,4-dichlorobenzal-bis-acetoacetate 3,4-Dichlorobenzaldehyde (100 g) in 95% ethanol (120 mL) was treated with ethylacetoacetate (146 mL) and stirred until a homogenous solution was obtained. This solution was treated with piperidine (8 mL) and left to stand for 18 hours. The crude product was recrystallized from 95% ethanol to give the title compound (230 g).

Step B 3-(3,4-Dichlorophenyl)glutaric acid

Diethyl-3,4-dichlorobenzal-bis-acetoacetate (155 g) in ethanol 2 L) was treated with 50% NaOH (2 L) and heated at reflux temperature for 4 hours. Water (1 L) was added to the reaction mixture and approx. 1.5 L of solvent removed by distillation. The remaining solution was poured onto ice (1 Kg) and sufficient HCl was added to adjust the pH to 1.

The resulting solution was extracted with EtOAc (3×1.5 L) and the combined extracts dried over MgSO$_4$, filtered and concentrated to give 100 g of the title compound.

Step C 3-(3,4-Dichlorophenyl)glutaric anhydride 3-(3,4-Dichlorophenyl)glutaric acid (100 g) was treated with acetyl chloride (300 mL) and the resulting mixture heated at reflux for 5 hours. The cooled reaction mixture was then azeotroped with toluene and concentrated under reduced pressure. The residue was slurried with diethyl ether (250 mL) and filtered to afford the title compound (86 g).

Step D 3,4-Dichloro-beta-[2-[(phenyl)methylamino]-2-oxoethyl] benzenepropanoic acid 3-(3,4-Dichlorophenyl)glutaric anhydride in CH$_2$Cl$_2$ (20 mL) at 0° C. was treated sequentially with N-methylaniline (0.518 g), triethylamine (0.489 g) and N,N-dimethylaminopyridine (trace). The mixture was stirred at 0° C. for two hours then allowed to warm to room temperature and stirred for 12 hours. The reaction mixture was washed with 1N HCl (2×20 mL) and water (20 mL). The organic layers were dried over MgSO$_4$, filtered and concentrated to afford the title compound (1.2 g).

Step E 3,4-Dichloro-beta-(2-hydroxyethyl)-N-methyl-N-phenylbenzenepropanamide 3,4-Dichloro-beta-[2-[(phenyl)methylamino]-2-oxoethyl] benzenepropanoic acid (0.98 g) in EtOAc (25 mL) was treated with carbonyldiimidazole (0.653 g) and N,N-dimethylaminopyridine (trace). The resulting solution was stirred at room temperature for 15 minutes and then heated at 50° C. for two hours. The reaction mixture was cooled to 0° C. and treated with a solution of NaBH$_4$ (0.668 g) in H$_2$O (10 mL), warmed slowly to room temperature and stirred for 12 hours. The reaction mixture was then diluted with Et$_2$O and washed with 1N HCl (20 mL), sat. NaHCO$_3$ (20 mL) and water (20 mL). The organic phase was dried over MgSO$_4$, filtered and concentrated under reduced pressure to yield the title compound (0.908 g). Mass spectrum (CI): 352.

Step F 3,4-Dichloro-beta-(2-methanesulfonyloxyethyl)-N-methyl-N-phenylbenzenepropanamide 3,4-Dichloro-beta-(2-hydroxyethyl)-N-methyl-N-phenylbenzenepropanamide (0.9 g) in CH$_2$Cl$_2$ (25 mL) was cooled to −5° to −10° C. and treated sequentially with Et$_3$N (0.332 g), and methanesulfonyl chloride (0.365 g). After two hours the reaction mixture was washed with water (3×20 mL) and the organic layer separated, dried over MgSO$_4$, filtered and concentrated under reduced pressure to give the title compound (1.1 g).

Step G

Beta-(3,4-Dichlorophenyl)-4-hydroxy-N-methyl-N,4-diphenyl-1-piperidine pentamide 3,4-Dichloro-beta-(2-methanesulfonyloxyethyl)-N-methyl-N-phenylbenzenepropanamide (1.1 g) in DMF (10 mL) was treated with 4-phenyl-4-hydroxypiperidine (1.14 g) and the mixture heated at 60° C. for 18 hours. The cooled reaction mixture was diluted with EtOAc (100 mL) and the aqueous phase removed. The aqueous layer was extracted with EtOAc (2×100 mL) and the combined organic extracts, washed with water (100 mL), dried over MgSO$_4$, filtered and concentrated under reduced pressure to give an oil. Silica gel chromatography eluting with 95:5 (CH$_2$Cl$_2$:MeOH) gave the title compound (0.4 g). M.p. 67°–72°, Mass spectrum (FAB): 513 (70%), 511 (100%).

Step H 3,4-Dichloro-beta-(2-oxoethyl)-N-methyl-N-phenylbenzenepropanamide

Oxalyl chloride (7.74 g) in CH$_2$Cl$_2$ (80 mL) was added to a −78° C. solution of DMSO (9.5 g) in CH$_2$Cl$_2$ (30 mL) over 15 mins. This mixture was stirred for 15 minutes whereupon a CH$_2$Cl$_2$ (50 mL) solution of 3,4-Dichloro-beta-(2-hydroxyethyl)-N-methyl-N-phenylbenzenepropanamide (17.15 g) was added over 20 minutes. The mixture was stirred for 30 minutes and then treated with a solution of Et$_3$N (14.76 g) in CH$_2$Cl$_2$ (20 mL) and stirred for an additional 30 minutes at −78° C., followed by 1.5 hours at room temperature. The reaction mixture was washed with water (100 mL), the organic fraction separated, dried over MgSO$_4$, filtered and concentrated under reduced pressure to yield an oil (20 g). Silica gel chromatography eluting with 5–15% EtOAc/Hex gave the title compound (15.2 g).

Step I

Beta-(3,4-Dichlorophenyl)-4-hydroxy-N-methyl-N,4-diphenyl-1-piperidine pentamide 3,4-Dichloro-beta-(2-oxoethyl)-N-methyl-N-phenylbenzenepropanamide (0.43 g), in MeOH (20 mL) was treated sequentially with molecular sieves 3A (2.0 g), 4-phenyl-4-hydroxypiperidine HCl (0.34 g) and NaBH$_3$CN (0.32 g). The resulting mixture was stirred at room temperature for 18 hours. The reaction mixture was filtered through a pad of celite (trademark) and concentrated under reduced pressure. The residue was partitioned between 10% NH$_4$OH solution and CH$_2$Cl$_2$ (25 mL) The organic layer was separated and the aqueous layer extracted with CH$_2$Cl$_2$ (2×25 mL). The combined organic layers were dried over MgSO$_4$, filtered and concentrated under reduced pressure to give a crude oil (0.7 g). Silica gel chromatography eluting with 1–2% MeOH/CH$_2$Cl$_2$ gave the title compound (0.42 g). Mass spectrum (CI): 524.

EXAMPLE 2

1-[3-(3,4-Dichlorophenyl)-5-[(methyl)phenylamino] pentyl]-4-phenyl-4-piperidinol Beta-(3,4-Dichlorophenyl)-4-hydroxy-N-methyl-N,4-diphenyl-1-piperidine pentamide (0.22 g) in THF (25 mL) was treated with BH$_3$:DMS (0.212 mL; 10M) and heated at reflux temperature for 18 hours. The cooled reaction mixture was then treated with MeOH (2.0 mL) and the solvent evaporated under reduced pressure. The residue was dissolved in EtOH (20 mL), treated with potassium carbonate (##.# g) and heated at reflux temperature for 3 hours. The reaction mixture was concentrated under reduced pressure and partitioned between CH$_2$Cl$_2$ (20 mL) and saturated NaHCO$_3$ solution (20 mL). The organic portion was separated and the aqueous rextracted with CH$_2$Cl$_2$ (2×20 mL). The combined organic was dried over MgSO$_4$, filtered and evaporated to give the title compound (0.20 g). Mass spectrum (FAB): 515.

EXAMPLE 3

Beta-(1,3-benzodioxol-5-yl)-4-hydroxy-N-methyl-N, 4-diphenyl-1-piperidinepentamide Step A Diethyl-(1,3-benzodioxol-5-yl)-bis-acetoacetate Piperonal (25 g) in 95% ethanol (30 mL) was treated with ethylacetoacetate (42.5 mL) and stirred until a homogenous solution was obtained. Piperidine (2.3 mL) was added and the resulting solution stirred 18 hours. The crude product was obtained by filteration and subsequently recrystallized from 95% ethanol to give the title compound (35 g).

Step B 3-(1,3-Benzodioxol-5-yl)glutaric acid

Diethyl-3,4-methylenedioxybenzal-bis-acetoacetate (30 g) in ethanol (300 mL) was treated with 50% NaOH (300 mL) and heated at reflux for 4 hours. Approximately 250 mL of solvent removed by distillation. The remaining solution was cooled to 0° C. and sufficient HCl was added dropwise to adjust the pH to 1. The resulting solution was extracted with EtOAc (3×500 mL) and the combined extracts dried over $MgSO_4$, filtered and concentrated under reduced pressure to give the title compound as a white solid (19 g).

Step C 3-(1,3-Benzodioxol-5-yl)glutaric anhydride 3-(1,3-benzodioxol-5-yl)glutaric acid (3.2 g) was treated with acetyl chloride (15 mL) and the resulting mixture heated at reflux for 5 hours. The cooled reaction mixture was then azeotroped with toluene (2×100 mL) and concentrated under reduced pressure. The residue was slurried with diethyl ether and filtered to afford the title compound (2.91 g).

Step D

Beta-[2-[(phenyl)methylamino]-2-oxoethyl]-1,3-benzodioxol-5-ylpropanoic acid 3-(1,3-Benzodioxol-5-yl)glutaric anhydride (2.91 g) in $CH_2Cl_2$ (100 mL) at 0° C. was treated sequentially with N-methylaniline (1.68 mL), triethylamine (2.16 mL) and N,N-dimethylaminopyridine (150 mg). The mixture was stirred at 0° C. for two hours then allowed to warm to room temperature and stirred for 12 hours. The reaction mixture was diluted with $CH_2Cl_2$ (300 mL) and washed with 1N HCl (1×150 mL) and water (1×150 mL). The organic layers were dried over $MgSO_4$, filtered and concentrated to afford the title compound (4.2 g).

Step E

Beta-(2-hydroxyethyl)-N-methyl-N-phenyl-1,3-benzodioxol-5-yl-propanamide

β-[2-[(phenyl)methylamino]-2-oxoethyl]-1,3-benzodioxol-5-yl-propanoic acid (4.2 g) in EtOAc (100 mL) was treated with carbonyldiimidazole (2.51 g) and N,N-dimethylaminopyridine (146 mg). The resulting solution was stirred at room temperature for 15 minutes and then heated at 50° C. for two hours. The reaction mixture was cooled to 0° C. and treated with a solution of $NaBH_4$ (2.34 g) in $H_2O$ (50 mL), warmed slowly to room temperature and stirred for 12 hours. The reaction mixture was diluted with EtOAc (200 mL) and washed with 1N HCl (1×150 mL), sat. $NaHCO_3$ (1×150 mL) and water (1×150 mL). The organic phase was dried over $MgSO_4$, filtered and concentrated under reduced pressure to yield the crude compound as a oil. Silica gel chromatography eluting with 0–10% MeOH/$CH_2Cl_2$ gave the title compound (2.36 g). Mass spectrum (CI): 328.

Step F

Beta-(2-oxoethyl)-N-methyl-N-phenyl-1,3-benzodioxol-5-yl-propanamide

A solution of β-(2-hydroxyethyl)-N-methyl-N-phenyl-1,3-benzodioxol-5-yl-propanamide (500 mg) in $CH_2Cl_2$ (10 mL) was treated with PDC (570 mg) and molecular sieves (4Å, 570 mg) and stirred at room temperture for 2 hours. The reaction mixture was filtered through a pad of silica gel rinsed with EtOAc (100 mL) and concentrated under reduced pressure to yield an oil. Silica gel chromatography eluting with 50–75% EtOAc/Hexanes gave the desired title compound (374 mg).

Step G

Beta-(1,3-benzodioxol-5-yl)-4-hydroxy-N-methyl-N,4-diphenyl-1-piperidinepentamide β-(2-oxoethyl)-N-methyl-N-phenyl-1,3-benzodioxol-5-yl-propanamide (370 mg), in MeOH/THF (1:1, 10 mL) was treated sequentially with molecular sieves 3A (480 mg), 4-phenyl-4-hydroxypiperidine HCl (480 mg) and $NaBH_3CN$ (72 mg). The resulting mixture was stirred at room temperature for 18 hours. The reaction mixture was with quenched with water (10 mL) and diluted with $CH_2Cl_2$ (50 mL). The organic layer was separated and the aqueous layer extracted with $CH_2Cl_2$ (3×20 mL) The combined organic layers were dried over $MgSO_4$, filtered and concentrated under reduced pressure to give the crude oil. Silica gel chromatography eluting with 1–2% MeOH/$CH_2Cl_2$ gave the title compound (310 mg). Mass spectrum (CI): 487.

EXAMPLE 4

Beta-(3,4-Difluorophenyl)-4-hydroxy-N-methyl-N,4-diphenyl-1-piperidinepentamide

Step A

Diethyl-3,4-difluorobenzal-bis-acetoacetate 3,4-Difluorobenzaldehyde (5 g) in 95% ethanol (20 mL) was treated with ethylacetoacetate (18 mL) and stirred until a homogenous solution was obtained. Piperidine (1 mL) was added and the resulting solution stirred 18 hours. The crude product was obtained by filteration and subsequently recrystallized from 95% ethanol to give the title compound (11 g).

Step B 3-(3,4-Difluorophenyl)glutaric acid

Diethyl-3,4-difluorobenzal-bis-acetoacetate (11 g) in ethanol (150 mL) was treated with 50% NaOH (150 mL) and heated at reflux for 4 hours. Approximately 100 mL of solvent was removed by distillation. The remaining solution was cooled to 0° C. and sufficient HCl was added dropwise to adjust the pH to 1. The resulting solution was extracted with EtOAc (3×300 mL) and the combined extracts dried over $MgSO_4$, filtered and concentrated under reduced pressure to give the title compound as a white solid (7.4 g).

Step C 3-(3,4-Difluorophenyl)glutaric anhydride 3-(3,4-Difluorophenyl)glutaric acid (7.4 g) was treated with acetyl chloride (50 mL) and the resulting mixture heated at reflux for 5 hours. The cooled reaction mixture was then azeotroped with toluene (3× 100 mL) and concentrated under reduced pressure. The residue was slurried with diethyl ether and filtered to afford the title compound (6.5 g).

Step D 3,4-Difluoro-β-[2-[(phenyl)methylamino]-2-oxoethyl] benzenepropanoic acid 3-(3,4-Difluorophenyl)glutaric anhydride (3.61 g) in $CH_2Cl_2$ (75 mL) at 0° C. was treated sequentially with N-methylaniline (2.16 mL), triethylamine (2.78 mL) and N,N-dimethylaminopyridine (195 mg). The mixture was stirred at 0° C. for two hours then allowed to warm to room temperature and stirred for 12 hours. The reaction mixture was diluted with $CH_2Cl_2$ (300 mL) and washed with 1N HCl (1×100 mL) and water (1×100 mL). The organic layers were dried over $MgSO_4$, filtered and concentrated to afford the title compound (4.3 g).

Step E 3,4-Difluoro-β-(2-hydroxyethyl)-N-methyl-N-phenylbenzenepropanamide 3,4-Difluoro-β-[2-[(phenyl)methylamino]-2-oxoethyl] benzenepropanoic acid (4.3 g) in EtOAc (100 mL) was treated with carbonyldiimidazole (3.24 g) and N,N-dimethylaminopyridine (195 mg). The resulting solution was stirred at room temperature for 15 minutes and then heated at 50° C. for two hours. The reaction mixture was cooled to 0° C. and treated with a solution of NaBH$_4$ (3.02 g) in H$_2$O (50 mL), warmed slowly to room temperature and stirred for 12 hours. The reaction mixture was diluted with EtOAc (200 mL) and washed with 1N HCl (1×100 mL), sat. NaHCO$_3$ (1×100 mL) and water (1×100 mL). The organic phase was dried over MgSO$_4$, filtered and concentrated under reduced pressure to yield the crude compound as a oil. Silica gel chromatography eluting with 0–10% MeOH/CH$_2$Cl$_2$ gave the title compound (3.64 g). Mass spectrum (CI): 320.

Step F 3,4-Difluoro-β-(2-oxoethyl)-N-methyl-N-phenylbenzenepropanamide

Oxalyl chloride (0.171 mL) in CH$_2$Cl$_2$ (10 mL) was added to a –78° C. solution of DMSO (0.278 mL) in CH$_2$Cl$_2$ over 15 mins. This mixture was stirred for 15 minutes. Whereupon a CH$_2$Cl$_2$ solution of 3,4-difluoro-β-(2-hydroxyethyl)-N-methyl-N-phenylbenzene propanamide (500 mg) was added over 20 minutes. The mixture was stirred for 30 minutes and then treated with a solution of Et$_3$N (0.655 mL) in CH$_2$Cl$_2$ and stirred for an additional 30 minutes at –78° C., followed by 1.5 hours at room temperature. The reaction mixture was washed with 0.1N HCl (1×50 mL) and brine (1×50 mL. The organic layer was dried over MgSO$_4$, filtered and concentrated under reduced pressure to yield an oil. Silica gel chromatography eluting with 5–15% EtOAc/Hex gave the title compound (388 mg).

Step G

β-(3,4-Difluorophenyl)-4-hydroxy-N-methyl-N,4-diphenyl-1-piperidinepentamide 3,4-Difluoro-β-(2-oxoethyl)-N-methyl-N-phenylbenzenepropanamide (520 mg), in MeOH/THF (1:1, 15 mL) was treated sequentially with molecular sieves 3A (700 mg), 4-phenyl-4-hydroxypiperidine HCl (700 mg) and NaBH$_3$CN (103 mg). The resulting mixture was stirred at room temperature for 18 hours. The reaction mixture was with quenched with water (20 mL) and diluted with CH$_2$Cl$_2$ (50 mL). The organic layer was separated and the aqueous layer extracted with CH$_2$Cl$_2$ (3×50 mL) The combined organic layers were dried over MgSO$_4$, filtered and concentrated under reduced pressure to give the crude oil. Silica gel chromatography eluting with 1–2% MeOH/CH$_2$Cl$_2$ gave the title compound (570 mg). Mass spectrum (FAB): 479.2498.

EXAMPLE 5

Beta-(3,4-Dichlorophenyl)-4-hydroxy-N,4-diphenyl-1-piperidinepentamide

Step A 3,4-Dichloro-β-[(2-phenylamino)-2-oxoethyl]-benzenepropanoic acid 3-(3,4-Dichlorophenyl)glutaric anhydride (5 g, Example 1, Step C) in CH$_2$Cl$_2$ (100 mL) at 0° C. was treated sequentially with aniline (2.19 mL), triethylamine (3.3 mL) and N,N-dimethylaminopyridine (236 mg). The mixture was stirred at 0° C. for two hours then allowed to warm to room temperature and stirred for 12 hours. The reaction mixture was diluted with CH$_2$Cl$_2$ (300 mL) and washed with 1N HCl (1×150 mL) and water (1×150 mL). The organic layers were dried over MgSO$_4$, filtered and concentrated to afford the title compound (5.4 g).

Step B 3,4-Dichloro-β-(2-hydroexyethyl)-N-phenylbenzenepropamide 3,4-Dichloro-β-[(2-phenylamino)-2-oxoethyl]-benzenepropanoic acid (4.5 g) in EtOAc (100 mL) was treated with carbonyldiimidazole (2.6 g) and N,N-dimethylaminopyridine (156 mg). The resulting solution was stirred at room temperature for 15 minutes and then heated at 50° C. for two hours. The reaction mixture was cooled to –10° C. and treated with a solution of NaBH$_4$ (2.42 g) in H$_2$O (50 mL), warmed slowly to room temperature and stirred for 12 hours. The reaction mixture was diluted with EtOAc (200 mL) and washed with 1N HCl (1×150 mL), sat. NaHCO$_3$ (1×150 mL) and water (1×150 mL). The organic phase was dried over MgSO$_4$, filtered and concentrated under reduced pressure to yield the crude compound as a oil. Silica gel chromatography eluting with 0–10% MeOH/CH$_2$Cl$_2$ gave the title compound (2 g). Mass spectrum (CI): 338.

Step C 3,4-Difluoro-β-(2-methanesulfonyloxyethyl)-N-phenylbenzenepropanamide 3,4-Dichloro-β-(2-hydroexyethyl)-N-phenylbenzenepropamide (340 mg) in CH$_2$Cl$_2$ was cooled to –5° to –10° C. and treated sequentially with Et$_3$N (0.278 mL) and methanesulfonyl chloride (0.097 mL). After one hour the reaction mixture was diluted with CH$_2$Cl$_2$ (75 mL) and washed with sat. NaHCO3 (1×50 mL) The organic layer was separated: dried over MgSO$_4$, filtered and concentrated under reduced pressure to give the title compound (480 mg).

Step D

β-(3,4-Dichlorophenyl)-4-hydroxy-N,4-diphenyl-1-piperidinepentamide 3,4-Difluoro-β-(2-methanesulfonyloxyethyl)-N-phenylbenzenepropanamide (480 mg) in DMF (5 mL) was treated with 4-phenyl-4-hydroxypiperidine (177 mg) and the mixture stirred at room temperature for 18 hours. The reaction mixture was diluted the EtOAc (50 mL) and the aqueous phase removed. The aqueous layer was extracted with EtOAc and the combined organic extracts, washed with water, dried over MgSO$_4$, filtered and concentrated under reduced pressure to give an oil. Silica gel chromatography eluting with 95:5 (CH$_2$Cl$_2$:MeOH) gave the title compound (246 mg). Mass spectrum (CI): 497.

EXAMPLE 6

N-(4-Chlorophenyl)-beta-(3,4-Dichlorophenyl)-4-hydroxy-4-phenyl-1-piperidinepentamide Step A 3,4-Dichloro-beta-[2-[(4-chlorophenyl)amino]-2-oxoethyl]benzenepropanoic acid 3-(3,4-Dichlorophenyl)glutaric anhydride in CH$_2$Cl$_2$ (75 mL) at 0° C. was treated sequentially with 4-chloroaniline (2.25 g), triethylamine (1.79 g) and N,N-dimethylaminopyridine (trace). The mixture was stirred at 0° C. for two hours then allowed to warm to room temperature and stirred for 12 hours. The reaction mixture was washed with 1N HCl (3×50 mL) and water (50 mL). The organic layers were dried over MgSO$_4$, filtered and concentrated to afford the title compound (4.9 g).

Step B

3,4-Dichloro-beta-(2-hydroxyethyl)-N-(4-chlorophenyl)benzenepropanamide 3,4-Dichloro-beta-[2-[(4-chlorophenyl)amino]-2-oxoethyl]benzenepropanoic acid (4.0 g) in EtOAc (75 mL) was treated with carbonyldiimidazole (2.52 g) and N,N-dimethylaminopyridine (trace). The resulting solution was stirred at room temperature for 15 minutes and then heated at 50° C. for two hours. The reaction mixture was cooled to 0° C. and treated with a solution of NaBH₄ (2.59 g) in H₂O (40 mL), warmed slowly to room temperature and stirred for 12 hours. The reaction mixture was then diluted with Et₂O and washed with 1N HCl (100 mL), sat. NaHCO₃ (100 mL) and water (100 mL). The organic phase was dried over MgSO₄, filtered and concentrated under reduced pressure to yield the title compound (3.81 g).

Step C

3,4-Dichloro-beta-(2-methanesulfonyloxyethyl)-N-(4-chlorophenyl)benzenepropanamide 3,4-Dichloro-beta-(2-hydroxyethyl)-N-(4-chlorophenyl)benzenepropanamide (3.5 g) in CH₂Cl₂ (60 mL) was cooled to −5° to −10° C. and treated sequentially with Et₃N (1.19 g), and methanesulfonyl chloride (1.35 g). After two hours the reaction mixture was washed with water (3×50 mL) and the organic layer separated, dried over MgSO₄, filtered and concentrated under reduced pressure to give the title compound (3.8 g).

Step D

N-(4-Chlorophenyl)-beta-(3,4-Dichlorophenyl)-4-hydroxy-4-phenyl-1-piperidine-pentamide 3,4-Dichloro-beta-(2-methanesulfonyloxyethyl)-N-phenylbenzenepropanamide (3.8 g) in DMF (50 mL) was treated with 4-phenyl-4-hydroxypiperidine (3.74 g) and the mixture heated at 60° C. for 18 hours. The cooled reaction mixture was diluted the EtOAc (100 mL) and water (100 mL) and the aqueous phase removed. The aqueous layer was extracted with EtOAc (2×100 mL) and the combined organic extracts, washed with water (100 mL), dried over MgSO₄, filtered and concentrated under reduced pressure to give an oil. Silica gel chromatography eluting with 5% MeOH:CH₂Cl₂ gave the title compound (1.2 g). Mass spectrum (FAB): 386.

EXAMPLE 7

1-[5-(4-Chlorophenyl)amino]-3-(3,4-dichlorophenyl)pentyl]-4-phenyl-4-piperidinol N-(4-Chlorophenyl)-beta-(3,4-Dichlorophenyl)-4-hydroxy-4-phenyl-1-piperidine-pentamide (0.5 g) in THF (35 mL) was treated with BH₃:DMS (0.335 mL; 10 M) and heated at reflux temperature for 18 hours. The cooled reaction mixture was then treated with MeOH (2.0 mL) and the solvent evaporated under reduced pressure. The residue was dissolved in EtOH (20 mL), treated with potassium carbonate and heated at reflux temperature for 3 hours. The reaction mixture was concentrated under reduced pressure and partitioned between CH₂Cl₂ (20 mL) and saturated NaHCO₃ solution (20 mL). The organic portion was separated and the aqueous rextracted with CH₂Cl₂ (2×20 mL). The combined organic was dried over MgSO₄, filtered and evaporated to give an oil. Chromatography over silica gel eluting with 5% MeOH:CH₂Cl₂ gave the title compound (0.26 g). Mass spectrum (FAB): 517.

EXAMPLE 8

4-Hydroxy-N-methyl-N, Beta,4-triphenyl-1-piperidinepentanamide

Step A

3-Phenylglutaric anhydride

3-Phenylglutaric acid (100 g) in CH₂Cl₂ (800 mL) was treated with dicyclohexylcarbodiimide (104 g) in CH₂Cl₂ (400 mL) over 30 minutes. The resulting mixture was stirred at ambient temperature for 48 hours. The reaction mixture was then diluted with hexane (800 mL) and filtered. The filtrate was concentrated under reduced pressure and the residue crystallized from ethyl acetate/hexane to afford the title compound (53 g).

Step B

Beta-[2-[(phenyl)methylamino]-2-oxoethyl]benzenepropanoic acid

3-Phenylglutaric anhydride (8.0 g) in CH₂Cl₂ (100 mL) at 0° C. was treated sequentially with N-methylaniline (5.63 g), triethylamine (5.32 g) and N,N-dimethylaminopyridine (1.0 g). The mixture was stirred at 0° C. for two hours then allowed to warm to room temperature and stirred for 12 hours. The reaction mixture was washed with 1N HCl (2×50 mL) and water (100 mL). The organic layers were dried over MgSO₄, filtered and concentrated to afford the title compound (11.5 g).

Step C

Beta-(2-hydroxyethyl)-N-methyl-N-phenylbenzenepropanamide

Beta-[2-[(phenyl)methylamino]-2-oxoethyl]benzenepropanoic acid (11.5 g) in EtOAc (225 mL) was treated with carbonyldiimidazole (11.68 g) and N,N-dimethylaminopyridine (1.0 g). The resulting solution was stirred at room temperature for 15 minutes and then heated at 50° C. for two hours. The reaction mixture was cooled to 0° C. and treated with a solution of NaBH₄ (9.74 g) in H₂O (150 mL), warmed slowly to room temperature and stirred for 12 hours. The reaction mixture was then diluted with Et₂O and washed with 1N HCl (100 mL), sat. NaHCO₃ (100 mL) and water (100 mL). The organic phase was dried over MgSO₄, filtered and concentrated under reduced pressure to yield the title compound (10.4 g).

Step D

Beta-(2-methanesulfonyloxyethyl)-N-methyl-N-phenylbenzenepropanamide

Beta-(2-hydroxyethyl)-N-methyl-N-phenylbenzenepropanamide (5.0 g) in CH₂Cl₂ (100 mL) was cooled to −5° to −10° C. and treated sequentially with Et₃N (2.23 g), and methanesulfonyl chloride (2.53 g). After two hours the reaction mixture was washed with water(3×50 mL) and the organic layer separated, dried over MgSO₄, filtered and concentrated under reduced pressure to give the title compound (6.4 g).

Step E

4-Hydroxy-N-methyl-N, Beta,4-triphenyl-1-piperidinepentanamide

Beta-(2-methanesulfonyloxyethyl)-N-methyl-N-phenylbenzenepropanamide (2.0 g) in DMF (10 mL) was treated with 4-phenyl-4-hydroxypiperidine (1.44 g) and the mixture heated at 60° C. for 18 hours. The cooled reaction mixture was diluted the EtOAc (100 mL) and water (100 mL) and the aqueous phase removed. The aqueous layer was extracted with EtOAc (2×100 mL) and the combined organic extracts, washed with water (100 mL), dried over MgSO₄, filtered and concentrated under reduced pressure to give an oil. Silica gel chromatography gave the title compound (0.8 g). Mass spectrum (FAB): 443.

EXAMPLE 9

1-[5-[(Phenyl)methylamino]-3-phenylpentyl]-4-phenyl-4-piperidinol

4-Hydroxy-N-methyl-N, Beta,4-triphenyl-1-piperidinepentanamide (0.3 g) in THF (25 mL) was treated with BH₃:DMS (0.335 mL; 10M) and heated at reflux temperature for 18 hours. The cooled reaction mixture was then treated with MeOH (2.0 mL) and the solvent evaporated under reduced pressure. The residue was dissolved in EtOH (20 mL), treated with potassium carbonate and heated at reflux temperature for 3 hours. The reaction mixture was concentrated under reduced pressure and partitioned between CH₂Cl₂ (20 mL) and saturated NaHCO₃ solution (20 mL). The organic portion was separated and the aqueous rextracted with CH₂Cl₂ (2×20 mL). The combined organic was dried over MgSO₄, filtered and evaporated to give the title compound (0.28 g). Mass spectrum (CI): 429.

EXAMPLE 10

N-(4-Chlorophenyl)-4-hydroxy-N-methyl-Beta,4-diphenyl-1-piperidinepentanamide

Step A

Beta-[2-[(4-chlorophenyl)methylamino]-2-oxoethyl] benzenepropanoic acid

3-Phenylglutaric anhydride (2.0 g) in CH₂Cl₂ (25 mL) at 0° C. was treated sequentially with 4-chloro-N-methylaniline (1.86 g), triethylamine (1.33 g) and N,N-dimethylaminopyridine (trace). The mixture was stirred at 0° C. for two hours then allowed to warm to room temperature and stirred for 12 hours. The reaction mixture was washed with 1N HCl (2×50 mL) and water (100 mL). The organic layers were dried over MgSO₄, filtered and concentrated to afford the title compound (2.7 g).

Step B

N-(4-Chlorophenyl)-beta-(2-hydroxyethyl)-N-methyl-benzenepropanamide

Beta-[2-[(4-chlorophenyl)methylamino]-2-oxoethyl] benzenepropanoic acid (1.3 g) in EtOAc (25 mL) was treated with carbonyldiimidazole (0.957 g) and N,N-dimethylaminopyridine (trace). The resulting solution was stirred at room temperature for 15 minutes and then heated at 50° C. for two hours. The reaction mixture was cooled to 0° C. and treated with a solution of NaBH₄ (0.983 g) in H₂O (15 mL), warmed slowly to room temperature and stirred for 12 hours. The reaction mixture was then diluted with Et₂O and washed with 1N HCl (20 mL), sat. NaHCO₃ (20 mL) and water (20 mL). The organic phase was dried over MgSO₄, filtered and concentrated under reduced pressure to yield the title compound (1.25 g).

Step C

N-(4-Chlorophenyl)-beta-(2-methanesulfonyloxyethyl)-N-methyl-benzenepropanamide

N-(4-Chlorophenyl)-beta-(2-hydroxyethyl)-N-methyl-benzenepropanamide (1.25 g) in CH₂Cl₂ (25 mL) was cooled to −5° to −10° C. and treated sequentially with Et₃N (0.497 g), and methanesulfonyl chloride (0.563 g). After two hours the reaction mixture was washed with water (3×25 mL), sat. NaHCO₃ (20 mL) and the organic layer separated, dried over MgSO₄, filtered and concentrated under reduced pressure to give the title compound (1.44 g).

Step D

N-(4-Chlorophenyl)-4-hydroxy-N-methyl-Beta,4-diphenyl-1-piperidinepentanamide

N-(4-Chlorophenyl)-beta-(2-methanesulfonyloxyethyl)-N-methyl-benzenepropanamide (1.44 g) in DMF (10 mL) was treated with 4-phenyl-4-hydroxypiperidine (1.61 g) and the mixture heated at 80° C. for 2 hours. The cooled reaction mixture was diluted the EtOAc (50 mL) and water (50 mL) and the aqueous phase removed. The aqueous layer was extracted with EtOAc (2×50 mL) and the combined organic extracts, washed with water (50 mL), dried over MgSO₄, filtered and concentrated under reduced pressure to give an oil. Silica gel chromatography eluting with 10% MeOH:CH₂Cl₂ gave the title compound (0.7 g). Mass spectrum (FAB): 477.

EXAMPLE 11

1-[5-[(4-Chlorophenyl)methylamino]-3-phenylpentyl]-4-phenyl-4-piperidinol

N-(4-Chlorophenyl)-4-hydroxy-N-methyl-Beta,4-diphenyl-1-piperidinepentanamide (0.3 g) in THF (25 mL) was treated with BH₃:DMS (0.311 mL; 10M) and heated at reflux temperature for 18 hours. The cooled reaction mixture was then treated with MeOH (2.0 mL) and the solvent evaporated under reduced pressure. The residue was dissolved in EtOH (20 mL), treated with potassium carbonate and heated at reflux temperature for 3 hours. The reaction mixture was concentrated under reduced pressure and partitioned between CH₂Cl₂ (20 mL) and saturated NaHCO₃ solution (20 mL). The organic portion was separated and the aqueous rextracted with CH₂Cl₂ (2×20 mL). The combined organic was dried over MgSO₄, filtered and evaporated to give an oil. Silica gel chromatography eluting with 5% NH₃/MeOH:CH₂Cl₂ gave the title compound (0.14 g). Mass spectrum (FAB): 463.3.

EXAMPLE 12

4-(Acetylamino)-N-methyl-N, Beta,4-triphenyl-1-piperidinepentanamide

Beta-(2-methanesulfonyloxyethyl)-N-methyl-N-phenylbenzenepropanamide (1.95 g) in DMF (25 mL) was treated with 4-acetylamino-4-phenylpiperidine hydrochlorode (3.44 g) and triethylamine (2.05 g) and the mixture heated at 60° C. for 18 hours. The cooled reaction mixture was diluted the EtOAc (100 mL) and water (100 mL) and the aqueous phase removed. The aqueous layer was extracted with EtOAc (2×100 mL) and the combined organic extracts, washed with water (100 mL), dried over MgSO₄, filtered and concentrated under reduced pressure to give an oil. Silica gel chromatography gave the title compound (0.3 g). Mass spectrum (FAB): 484.4.

EXAMPLE 13

4-(Acetylamino)-N-(4-chlorophenyl)-N-methyl-Beta,4-diphenyl-1-piperidinepentanamide N-(4-Chlorophenyl)-beta-(2-methanesulfonyloxyethyl)-N-methyl-benzenepropanamide (2.0 g) in DMF (10 mL) was treated with 4-acetylamino-4-phenylpiperidine hydrochlorode (3.21 g) and ethyl-N,N-diisopropylamine (2.48 g) and the mixture heated at 80° C. for 2 hours. The cooled reaction mixture was diluted the EtOAc (50 mL) and water (50 mL) and the aqueous phase removed. The aqueous layer was extracted with EtOAc (2×50 mL) and the combined organic extracts, washed with water (50 mL), dried over MgSO$_4$, filtered and concentrated under reduced pressure to give an oil. Silica gel chromatography eluting with 10% MeOH:CHaCl$_2$ gave the title compound (0.29 g). Mass spectrum (FAB): 518.3.

EXAMPLE 14

N-Methyl-N, Beta-diphenyl-4-(phenylmethyl)-1-piperidinepentanamide

Beta-(2-methanesulfonyloxyethyl)-N-methyl-N-phenylbenzenepropanamide (1.3 g) in DMF (10 mL) was treated with 4-phenylmethylpiperidine (1.57 g) and the mixture heated at 60° C. for 18 hours. The cooled reaction mixture was diluted the EtOAc (100 mL) and water (100 mL) and the aqueous phase removed. The aqueous layer was extracted with EtOAc (2×100 mL) and the combined organic extracts, washed with water (100 mL), dried over MgSO$_4$, filtered and concentrated under reduced pressure to give an oil. Silica gel chromatography gave the title compound (0.6 g). Mass spectrum (FAB): 441.1.

EXAMPLE 15

N-(4-Chlorophenyl)-N-methyl-Beta-phenyl-4-(phenylmethyl)-1-piperidinepentamide N-(4-Chlorophenyl)-beta-(2-methanesulfonyloxyethyl)-N-methyl-benzenepropanamide (1.35 g) in DMF (10 mL) was treated with 4-benzylpiperidine (1.49 g) and the mixture heated at 80° C. for 2 hours. The cooled reaction mixture was diluted the EtOAc (50 mL) and water (50 mL) and the aqueous phase removed. The aqueous layer was extracted with EtOAc (2×50 mL) and the combined organic extracts, washed with water (50 mL), dried over MgSO$_4$, filtered and concentrated under reduced pressure to give an oil. Silica gel chromatography eluting with 5% MeOH:CH$_2$Cl$_2$ gave the title compound (0.45 g). Mass spectrum (FAB): 475.2.

EXAMPLE 16

N-Methyl-N, Beta-diphenyl-4-(phenylmethyl)-1-piperazinepentamide

Beta-(2-methanesulfonyloxyethyl)-N-methyl-N-phenylbenzenepropanamide (1.95 g) in DMF (25 mL) was treated with N-phenylmethylpiperazine (2.38 g) and triethylamine (2.05 g) and the mixture heated at 60° C. for 18 hours. The cooled reaction mixture was diluted the EtOAc (100 mL) and water (100 mL) and the aqueous phase removed. The aqueous layer was extracted with EtOAc (2×100 mL) and the combined organic extracts, washed with water (100 mL), dried over MgSO$_4$, filtered and concentrated under reduced pressure to give an oil. Silica gel chromatography gave the title compound (0.45 g). Mass spectrum (FAB): 442.1.

EXAMPLE 17

N-(4-Chlorophenyl)-N-methyl-Beta-phenyl-4-(phenylmethyl)-1-piperazinepentamide N-(4-Chlorophenyl)-beta-(2-methanesulfonyloxyethyl)-N-methyl-benzenepropanamide (0.93 g) in DMF (10 mL) was treated with N-phenylmethylpiperazine (1.03 g) and the mixture heated at 80° C. for 2 hours. The cooled reaction mixture was diluted the EtOAc (50 mL) and water (50 mL) and the aqueous phase removed. The aqueous layer was extracted with EtOAc (2×50 mL) and the combined organic extracts, washed with water (50 mL), dried over MgSO$_4$, filtered and concentrated under reduced pressure to give an oil. Silica gel chromatography eluting with 10% MeOH:CH$_2$Cl$_2$ gave the title compound (0.5 g). Mass spectrum (FAB): 476.3.

EXAMPLE 18

Beta-(3,4-Dichlorophenyl)-1,2,3,4-tetrahydro-N-methyl-N-phenyl-2-isoquinolinepentamide 3,4-Dichloro-beta-(2-oxoethyl)-N-methyl-N-phenylbenzenepropanamide (0.53 g), in MeOH (35 mL) was treated sequentially with molecular sieves 3A (5.5 g), isoquinoline HCl (0.33 g) and NaBH$_3$CN (0.4 g). The resulting mixture was stirred at room temperature for 20 hours. The reaction mixture was filtered through a pad of celite (trademark) and concentrated under reduced pressure. The residue was partitioned between 10% NH$_4$OH solution and CH$_2$Cl$_2$ (25 mL) The organic layer was separated and the aqueous layer extracted with CH$_2$Cl$_2$ (2×25 mL). The combined organic layers were dried over MgSO$_4$, filtered and concentrated under reduced pressure to give a crude oil (0.7 g). Silica gel chromatography eluting with 2% MeOH/CH$_2$Cl$_2$ gave the title compound (0.27 g). Mass spectrum (FAB): 467.

EXAMPLE 19

3-(3,4-Dichlorophenyl)-1,2,3,4-tetrahydro-N-methyl-N-phenyl-2-isoquinolinepentanamine Beta-(3,4-Dichlorophenyl)-1,2,3,4-tetrahydro-N-methyl-N-phenyl-2-isoquinolinepentamide (0.22 g) in THF (20 mL) was treated with BH$_3$:DMS (0.25 mL; 10M) and heated at 50° for 20 hours. The cooled reaction mixture was then treated with MeOH (5.0 mL) and the solvent evaporated under reduced pressure. The residue was dissolved in EtOH (20 mL), treated with potassium carbonate (0.45 g) and heated at reflux temperature for 4 hours. The reaction mixture was concentrated under reduced pressure and partitioned between CH$_2$Cl$_2$ (20 mL) and H$_2$O (30 mL). The organic portion was separated and the aqueous rextracted with CH$_2$Cl$_2$ (2×20 mL). The combined organic was dried over MgSO$_4$, filtered and evaporated to give an oil (0.21 g). Silica gel chromatography eluting with 20% EtOAc/CH$_2$Cl$_2$ gave the title compound (0.10 g). Mass spectrum (FAB): 453.

EXAMPLE 20

Beta-(3,4-Dichlorophenyl)-3,4-dihydro-6-methoxy-N-methyl-4-oxo-N-phenyl-spiro[2H-1-benzopyran-2,4',-piperidine]-1'pentamide 3,4-Dichloro-beta-(2-oxoethyl)-N-methyl-N-phenylbenzenepropanamide (0.44 g), in MeOH (30 mL) was treated sequentially with molecular sieves 3A (2.0 g), 3,4-dihydro-6-methoxy-4-oxo-spiro[2H-1-benzopyran-2,4'-piperidine] HCl (0.41 g) and NaBH$_3$CN (0.33 g). The resulting mixture was stirred at room temperature for 19 hours. The reaction mixture was filtered through a pad of celite (trademark) and concentrated under reduced pressure. The residue was partitioned between 10% NH$_4$OH solution and CH$_2$Cl$_2$ (25 mL) The organic layer was separated and the aqueous layer extracted with CH$_2$Cl$_2$ (2×25 mL). The combined organic layers were dried over MgSO$_4$, filtered and concentrated under reduced pressure to give a crude solid (0.75 g). Silica gel chromatography eluting with 4%

MeOH/CH₂Cl₂ gave the title compound (0.45 g). Mass spectrum (FAB): 581.

EXAMPLE 21

1'-[3-(3,4-Dichlorophenyl)-5-(methylphenylamino) pentyl]-3,4-dihydro-6-methoxy-spiro[2H-1-benzopyran-2,4',-piperid]-4-ol Beta-(3,4-Dichlorophenyl)-3,4-dihydro-6-methoxy-N-methyl-4-oxo-N-phenyl-spiro[2H-1-benzopyran-2,4',-piperidine]-1'pentamide (0.33 g) in THF (30 mL) was treated with BH₃:DMS (0.3 mL; 10M) and heated at 50° for 19 hours. The cooled reaction mixture was then treated with MeOH (5.0 mL) and the solvent evaporated under reduced pressure. The residue was dissolved in EtOH (25 mL), treated with potassium carbonate (0.5 g) and heated at reflux temperature for 4.5 hours. The reaction mixture was concentrated under reduced pressure and partitioned between CH₂Cl₂ (20 mL) and H₂O (30 mL). The organic portion was separated and the aqueous rextracted with CH₂Cl₂ (2×20 mL). The combined organic was dried over MgSO₄, filtered and evaporated to give an oil. Silica gel chromatography eluting with 5% MeOH/CH₂Cl₂ gave the title compound (0.13 g). Mass spectrum (FAB): 569.

EXAMPLE 22

Beta-(3,4-Dichlorophenyl)-N-methyl-4-oxo-N-phenyl-1-piperidinepentamide 3,4-Dichloro-β-(2-oxoethyl)-N-methyl-N-phenylbenzenepropamide (4.53 g, Example 1 Step H), in MeOH/THF (1:1, 100 mL) was treated sequentially with molecular sieves 3A, (4.0 g), piperidone·H₂O·HCl (4 g) and NaBH₃CN (813 mg). The resulting mixture was stirred at room temperature for 18 hours. The reaction mixture was with quenched with water (50 mL) and diluted with CH₂Cl₂ (200 mL). The organic layer was separated and the aqueous layer extracted with CH₂Cl₂ (3×100 mL) The combined organic layers were dried over MgSO₄, filtered and concentrated under reduced pressure to give the crude oil. Silica gel chromatography eluting with 1–10% MeOH/CH₂Cl₂ gave the title compound (2.64 g). Mass spectrum (FAB): 433.1457.

EXAMPLE 23

Beta-(3,4-Dichlorophenyl)-N-methyl-N-phenyl-4-(phenylmethyl)-1-piperidinepentamide 3,4-Dichloro-beta-(2-oxoethyl)-N-methyl-N-phenylbenzenepropanamide (0.45 g), in MeOH (20 mL) was treated sequentially with molecular sieves 3A (2.0 g), 3,4-dihydro-6-methoxy-4-oxo-spiro[2H-1-benzopyran-2,4'-piperidine] HCl (0.41 g) and NaBH₃CN (0.34 g). The resulting mixture was stirred at room temperature for 18 hours. The reaction mixture was filtered through a pad of celite (trademark) and concentrated under reduced pressure. The residue was partitioned between 10% NH₄OH solution and CH₂Cl₂ (25 mL) The organic layer was separated and the aqueous layer extracted with CH₂Cl₂ (2×25 mL). The combined organic layers were dried over MgSO₄, filtered and concentrated under reduced pressure to give a crude oil (0.6 g). Silica gel chromatography eluting with 5% MeOH/ CH₂Cl₂ gave the title compound (0.34 g). Mass spectrum (FAB): 509.

EXAMPLE 24

N-(4-Chlorophenyl)-beta-(3,4-Dichlorophenyl)-4-hydroxy-N-methyl-4-phenyl-1-piperidinepentanamide Step A 3,4-Dichloro-beta-[2-[(4-chlorophenyl)methylamino]-2-oxoethyl]benzenepropanoic acid 3-(3,4-Dichlorophenyl)glutaric anhydride (10.0 g) in CH₂Cl₂ (150 mL) at 0° C. was treated sequentially with 4-chloro-N-methylaniline (6.8 g), triethylamine (4.87 g) and N,N-dimethylaminopyridine (0.5 g). The mixture was stirred at 0° C. for two hours then allowed to warm to room temperature and stirred for 12 hours. The reaction mixture was washed with 1N HCl (3×100 mL) and water (100 mL). The organic layers were dried over MgSO₄, filtered and concentrated to afford the title compound (14.9 g).

Step B 3,4-Dichloro-beta-(2-hydroxyethyl)-N-(4-chlorophenyl)-N-methylbenzenepropanamide 3,4-Dichloro-beta-[2-[(4-chlorophenyl)methylamino]-2-oxoethyl]benzenepropanoic acid (14.9 g) in EtOAc (270 mL) was treated with carbonyldiimidazole (9.1 g) and N,N-dimethylaminopyridine (trace). The resulting solution was stirred at room temperature for 15 minutes and then heated at 50° C. for two hours. The reaction mixture was cooled to 0° C. and treated with a solution of NaBH₄ (9.32 g) in H₂O (140 mL), warmed slowly to room temperature and stirred for 12 hours. The reaction mixture was then diluted with Et₂O and washed with 1N HCl (3×100 mL), sat. NaHCO₃ (250 mL) and water (250 mL). The organic phase was dried over MgSO₄, filtered and concentrated under reduced pressure to yield the title compound (12.64 g).

Step C 3,4-Dichloro-beta-(2-methanesulfonyloxyethyl)-N-(4-chlorophenyl)-N-methylbenzenepropanamide 3,4-Dichloro-beta-(2-hydroxyethyl)-N-(4-chlorophenyl)-N-methylbenzenepropanamide (2.1 g) in CH₂Cl₂ (40 mL) was cooled to −5° to −10° C. and treated sequentially with Et₃N (0.69 g), and methanesulfonyl chloride (0.78 g). After two hours the reaction mixture was washed with water(3×50 mL) and the organic layer separated, dried over MgSO₄, filtered and concentrated under reduced pressure to give the title compound (2.3 g).

Step D

N-(4-Chlorophenyl)-beta-(3,4-Dichlorophenyl)-4-hydroxy-N-methyl-4-phenyl-1-piperidinepentanamide 3,4-Dichloro-beta-(2-methanesulfonyloxyethyl)-N-methyl-N-phenylbenzenepropanamide (1.6 g) in DMF (10 mL) was treated with 4-phenyl-4-hydroxypiperidine (0.61 g) and K₂CO₃ (0.476 g). The mixture was stirred at ambient temperature then diluted with EtOAc (100 mL) and washed with H₂O (2×100 mL). The organic extracts were dried over MgSO₄, filtered and concentrated under reduced pressure to give an oil. Silica get chromatography eluting with 95:5 (CH₂Cl₂:MeOH) gave the title compound (0.56 g). Mass spectrum (FAB): 545.3.

EXAMPLE 25

1-[5-(4-Chlorophenyl)(methyl)amino]-3-[3,4-dichlorophenyl]-pentyl]-4-phenyl-4-piperidinol N-(4-Chlorophenyl)-beta-(3,4-Dichlorophenyl)-4-hydroxy-N-methyl-4-phenyl-1-piperidinepentanamide (0.35 g) in THF (30 mL) was treated with BH$_3$:DMS (0.31 mL; 10M) and heated at reflux temperature for 18 hours. The cooled reaction mixture was then treated with MeOH (2.0 mL) and the solvent evaporated under reduced pressure. The residue was dissolved in EtOH (20 mL), treated with potassium carbonate and heated at reflux temperature for 3 hours. The reaction mixture was concentrated under reduced pressure and partitioned between CH$_2$Cl$_2$ (20 mL) and saturated NaHCO$_3$ solution (20 mL). The organic portion was separated and the aqueous rextracted with CH$_2$Cl$_2$ (2×20 mL). The combined organic was dried over MgSO$_4$, filtered and evaporated to give an oil. Silica gel chromatography eluting with 5% MeOH:CH$_2$Cl$_2$ gave the title compound (0.13 g). Mass spectrum (FAB): 531.1.

EXAMPLE 26

N-(4-Chlorophenyl)-beta-(3,4-Dichlorophenyl)-N-methyl-4-oxo-1-piperidinepentanamide Step A 3,4-Dichloro-beta-(2-bromoethyl)-N-methyl-N-(4-chlorophenyl)benzene propanamide 3,4-Dichloro-beta-(2-methanesulfonyloxyethyl)-N-methyl-N-(4-chlorophenyl)benzene propanamide (6.3 g) in THF (50 mL) was treated with lithium carbonate (2.0 g) and lithium bromide (2.34 g). The mixture was heated at reflux temperature for 2 hours. The cooled reaction mixture was diluted the CH$_2$Cl$_2$ (100 mL) and washed with H$_2$O (2×100 mL). The organic extracts were dried over MgSO$_4$, filtered and concentrated under reduced pressure to give the title compound as a yellow oil, (5.6 g).

Step B

N-(4-Chlorophenyl)-beta-(3,4-Dichlorophenyl)-N-methyl-4-oxo-1-piperidine pentanamide 3,4-Dichloro-beta-(2-bromoethyl)-N-methyl-N-(4-chlorophenyl)benzene propanamide (4.6 g) in DMF (60 mL) was treated with 4-piperidone monohydrate hydrochloride (3.94 g) and K$_2$CO$_3$ (5.3 g). The mixture was stirred vigorously at ambient temperature for 120 hours. The reaction mixture was poured into H$_2$O (100 mL) and extracted with EtOAc (2×100 mL). The organic extracts were dried over MgSO$_4$, filtered and concentrated under reduced pressure to give an oil. Silica gel chromatography eluting with 95:5 (CH$_2$Cl$_2$:MeOH) gave the title compound (2.25 g). Mass spectrum (FAB): 467.1.

EXAMPLE 27

N-(4-Chlorophenyl)-beta-(3,4-Dichlorophenyl)-N-methyl-4-(phenylmethyl)-1-piperidinepentanamide Step A 3,4-Dichloro-beta-[2-[(4-chlorophenyl)methylamino]-2-oxoethyl]benzenepropanoic acid 3-(3,4-Dichlorophenyl)glutaric anhydride (5.0 g) in CH$_2$Cl$_2$ (100 mL) at 0° C. was treated sequentially with 4-chloro-N-methylaniline (2.92 mL)), triethylamine (3.36 mL) and N,N-dimethylaminopyridine (0.24 g). The mixture was stirred at 0° C. for two hours then allowed to warm to room temperature and stirred for 12 hours. The reaction mixture was washed with 1N HCl (2×100 mL) and water (2×100 mL). The organic layers were dried over MgSO$_4$, filtered and concentrated to afford the title compound (6.63 g).

Step B 3,4-Dichloro-beta-(2-hydroxyethyl)-N-methyl-N-(4-chlorophenyl)-benzenepropanamide 3,4-Dichloro-beta-[2-[(4-chlorophenyl)methylamino]-2-oxoethyl]benzenepropanoic acid (4.0 g) in EtOAc (75 mL) was treated with carbonyldiimidazole (2.43 g) and N,N-dimethylaminopyridine (0.122 g). The resulting solution was stirred at room temperature for 15 minutes and then heated at 50° C. for one hour. The reaction mixture was cooled to 0° C. and treated with a solution of NaBH$_4$ (2.45 g) in H$_2$O (50 mL), warmed slowly to room temperature and stirred for 12 hours. The reaction mixture was then diluted with EtOAc (100 mL) and washed with H$_2$O (100 mL), 1N HCl (100 mL), and sat. NaHCO$_3$ (100 mL). The organic phase was dried over MgSO$_4$, filtered and concentrated under reduced pressure to yield the title compound (3.69 g).

Step C 3,4-Dichloro-beta-(2-methanesulfonyloxyethyl)-N-methyl-N-(4-chlorophenyl)benzene propanamide 3,4-Dichloro-beta-(2-hydroxyethyl)-N-methyl-N-(4-chlorophenyl)-benzenepropanamide (3.6 g) in CH$_2$Cl$_2$ (100 mL) was cooled to −5° to −10° C. and treated sequentially with Et$_3$N (1.62 mL), and methanesulfonyl chloride (0.9 mL). After two hours the reaction mixture was washed with water (100 mL), brine (100 mL) and the organic layer separated, dried over MgSO$_4$, filtered and concentrated under reduced pressure to give the title compound (4.3 g).

Step D

N-(4-Chlorophenyl)-beta-(3,4-Dichlorophenyl)-N-methyl-4-(phenylmethyl)-1-piperidinepentanamide 3,4-Dichloro-beta-(2-methanesulfonyloxyethyl)-N-methyl-N-(4-chlorophenyl)benzene propanamide (1.6 g) in DMF (10 mL) was treated with 4-phenyl-4-hydroxypiperidine (1.14 g) and K$_2$CO$_3$ (0.476 g). The mixture was heated at 60° C. for 18 hours. The cooled reaction mixture was diluted the EtOAc (100 mL) and washed with H$_2$O (2×100 mL). The organic extracts were dried over MgSO$_4$, filtered and concentrated under reduced pressure to give an oil. Silica gel chromatography eluting with 95:5 (CH$_2$Cl$_2$:MeOH) gave the title compound (0.56 g). M.p. 67°–72°, Mass spectrum (CI): 543.

EXAMPLE 28

N-(4-Chlorophenyl)-gamma-(3,4-Dichlorophenyl)-N-methyl-4-(phenylmethyl)-1-piperidinepentanamine N-(4-Chlorophenyl)-beta-(3,4-Dichlorophenyl)-N-methyl-4-(phenylmethyl)-1-piperidinepentanamide (0.38 g) in THF (30 mL) was treated with BH$_3$:DMS (0.4 mL; 10M) and heated at reflux temperature for 18 hours. The cooled reaction mixture was then treated with MeOH (2.0 mL) and the solvent evaporated under reduced pressure. The residue was dissolved in EtOH (20 mL), treated with potassium carbonate and heated at reflux temperature for 3 hours. The reaction mixture was concentrated under reduced pressure and partitioned between CH$_2$Cl$_2$ (20 mL) and saturated NaHCO$_3$ solution (20 mL). The organic portion was separated and the aqueous rextracted with CH$_2$Cl$_2$ (2×20 mL). The combined organic was dried over MgSO$_4$, filtered and evaporated to give an oil. Silica gel chromatography eluting with 5% MeOH:CH$_2$Cl$_2$ gave the title compound (0.18 g). Mass spectrum (CI): 529.

EXAMPLE 29

Beta-(3,4-Dichlorophenyl)-4-hydroxy-N-methyl-N-(4-methoxyphenyl)-4-phenyl-1-piperidinepentanamide Step A 3,4-Dichloro-beta-[2-[(4-methoxyphenyl)methylamino]-2-oxoethyl]benzenepropanoic acid 3-(3,4-Dichlorophenyl)glutaric anhydride (5.0 g) in $CH_2Cl_2$ (100 mL) at 0° C. was treated sequentially with 4-methoxy-N-methylaniline (3.3 g)), triethylamine (3.36 mL) and N,N-dimethylaminopyridine (0.24 g). The mixture was stirred at 0° C. for two hours then allowed to warm to room temperature and stirred for 12 hours. The reaction mixture was washed with 1N HCl (100 mL) and water (2×100 mL). The organic layers were dried over $MgSO_4$, filtered and concentrated to afford the title compound (7.3 g).

Step B 3,4-Dichloro-beta-(2-hydroxyethyl)-N-methyl-N-(4-methoxyphenyl)-benzenepropanamide 3,4-Dichloro-beta-[2-[(4-methoxyphenyl)methylamino]-2-oxoethyl]benzenepropanoic acid (7.2 g) in EtOAc (125 mL) was treated with carbonyldiimidazole (4.4 g) and N,N-dimethylaminopyridine (0.22 g). The resulting solution was stirred at room temperature for 15 minutes and then heated at 50° C. for one hour. The reaction mixture was cooled to 0° C. and treated with a solution of $NaBH_4$ (4.46 g) in $H_2O$ (75 mL), warmed slowly to room temperature and stirred for 12 hours. The reaction mixture was then diluted with EtOAc (100 mL) and washed with $H_2O$ (100 mL), 1N HCl (100 mL), and $H_2O$ (100 mL). The organic phase was dried over $MgSO_4$, filtered and concentrated under reduced pressure to give an oil. Silica gel chromatography eluting with 60–100% EtOAc/hexane gave the title compound (5.43 g).

Step C 3,4-Dichloro-beta-(2-methanesulfonyloxyethyl)-N-methyl-N-(4-methoxyphenyl)benzene propanamide 3,4-Dichloro-beta-(2-hydroxyethyl)-N-methyl-N-(4-methoxyphenyl)-benzene propanamide (2.0 g) in $CH_2Cl_2$ (50 mL) was cooled to −5° to −10° C. and treated sequentially with $Et_3N$ (0.911 mL), and methanesulfonyl chloride (0.64 mL). After two hours the reaction mixture was washed with water (100 mL), brine (100 mL) and the organic layer separated, dried over $MgSO_4$, filtered and concentrated under reduced pressure to give the title compound (2.56 g).

Step D

Beta-(3,4-Dichlorophenyl)-4-hydroxy-N-methyl-N-(4-methoxyphenyl)-4-phenyl-1-piperidinepentanamide 3,4-Dichloro-beta-(2-methanesulfonyloxyethyl)-N-methyl-N-(4-methoxyphenyl)benzene propanamide (4.2 g) in DMF (20 mL) was treated with 4-phenyl-4-hydroxypiperidine (1.53 g) and $K_2CO_3$ (1.19 g). The mixture was heated at 60° C. for 18 hours. The cooled reaction mixture was diluted the EtOAc (200 mL) and washed with $H_2O$ (3×150 mL). The organic extracts were dried over $MgSO_4$, filtered and concentrated under reduced pressure to give an oil. Silica gel chromatography eluting with 90:10 ($CH_2Cl_2$:MeOH) gave the title compound (0.58 g). Mass spectrum (CI): 541.

EXAMPLE 30

N-[3,5-bis-(Trifluoromethyl)phenyl]-β-(3,4-dichlorophenyl)-4-hydroxy-N-methyl-4-phenyl-1-piperidinepentamide Step A 3,4-Dichloro-β-[2-[(3,5-bis-trifluoromethylphenyl)amino)]-2-oxoethyl]-benzenepropanoic acid 3-(3,4-Dichlorophenyl)glutaric anhydride (10 g, Example 1, Step C) in $CH_2Cl_2$ (300 mL) at 0° C. was treated sequentially with 3,5-bis-(trifluoromethyl)aniline (7.5 mL), triethylamine (6.7 mL) and N,N-dimethylaminopyridine (470 mg). The mixture was stirred at 0° C. for two hours then allowed to warm to room temperature and stirred for 12 hours. The reaction mixture was diluted with $CH_2Cl_2$ (500 mL) and washed with 1N HCl (1×200 mL) and water (1×200 mL). The organic layers were dried over $MgSO_4$, filtered and concentrated to afford the title compound (18 g).

Step B 3,4-Dichloro-β-[2-[(3,5-bis-trifluoromethylphenyl)methylamino)]-2-oxoethyl]-benzenepropanoic acid Sodium hydride (2.16 g, 95%) was suspended in THF (100 mL) and cooled to 0° C. 3,4-Dichloro-β-[2-[(3,5-bis-trifluoromethylphenyl)methylamino)]-2-oxoethyl]-benzenepropanoic acid (18 g), in THF (100 mL) was added dropwise. After addition the mixture was warmed to room temperature and stirred for 12 hours. The mixture was then heated at reflux for 1 hour. The mixture was cooled to room temperature and methyl iodide (2.6 mL) was added dropwise. The resulting mixture was heated at reflux for 24 hours. Cooled to 0° C. and quenched carefully with $H_2O$ (100 mL). Extracted with EtOAc (3×200 mL). The combine organic layers were dried over $MgSO_4$, filtered and concentrated under reduced pressure to give crude product. Silica gel chromatography eluting with 0–50% MeOH/$CH_2Cl_2$ gave the title compound (8.5 g).

Step C

N-(3,5-bis-trifluoromethylphenyl)-3,4-dichloro-β-(2-hydroxyethyl)-N-methyl-benzenepropanamide 3,4-Dichloro-β-[2-[(3,5-bis-trifluoromethylphenyl)methylamino)]-2-oxoethyl]-benzenepropanoic acid (7.8 g) in EtOAc (100 mL) was treated with carbonyldiimidazole (3.16 g) and N,N-dimethylaminopyridine (190 mg). The resulting solution was stirred at room temperature for 15 minutes and then heated at 50° C. for two hours. The reaction mixture was cooled to 0° C. and treated with a solution of $NaBH_4$ (2.95 g) in $H_2O$ (50 mL), warmed slowly to room temperature and stirred for 12 hours. The reaction mixture was diluted with EtOAc (300 mL) and washed with 1N HCl (1×200 mL), sat. $NaHCO_3$ (1×200 mL) and water (1×200 mL). The organic phase was dried over $MgSO_4$, filtered and concentrated under reduced pressure to yield the crude compound as a oil. Silica gel chromatography eluting with 0–10% MeOH/$CH_2Cl_2$ gave the title compound (6 g). Mass spectrum (CI): 488.

Step D

N-(3, 5-bis-trifluoromethylphenyl)-3,4-dichloro-β-(2-oxoethyl)-N-methyl-benzenepropamide A mixture of N-(3,5-bis-trifluoromethylphenyl)-3,4-dichloro-β-(2-hydroxyethyl)-N-methyl-benzenepropanamide (1.3 g) and molecular sieves (4A, 624 mg) in $CH_2Cl_2$ (20 mL) and was treated with TPAP (47 mg) and 4-methylmorpholine-N-oxide (624 mg) and stirred at room temperture for 2 hours. The reaction mixture was filtered through a pad of silica gel rinsed with EtOAc (100 mL) and concentrated under reduced pressure to yield an oil. Silica gel chromatography eluting with 50–75% EtOAc/ Hexanes gave the desired title compound (810 mg).

Step E

N-[3,5-bis-(Trifluoromethyl)phenyl]-β-(3,4-dichlorophenyl)-4-hydroxy-N-methyl-4-phenyl-1-piperidinepentamide N-(3,5-bis-trifluoromethylphenyl)-3,4-dichloro-β-(2-oxoethyl)-N-methyl-benzenepropamide (810 mg), in MeOH/THF (1:1, 20 mL) was treated sequentially with molecular sieves 3A (534 mg), 4-phenyl-4-hydroxypiperidine HCl (534 mg) and NaBH₃CN (104 mg). The resulting mixture was stirred at room temperature for 18 hours. The reaction mixture was with quenched with water (20 mL) and diluted with CH₂Cl₂ (50 mL). The organic layer was separated and the aqueous layer extracted with CH₂Cl₂ (3×50 mL) The combined organic layers were dried over MgSO₄, filtered and concentrated under reduced pressure to give the crude oil. Silica gel chromatography eluting with 1–2% MeOH/CH₂Cl₂ gave the title compound (700 mg). Mass spectrum (FAB): 647.1663.

EXAMPLE 31

Beta-(3,4-dichlorophenyl)-4-hydroxy-N-(2-methoxyphenyl)-N-methyl-4-phenyl-1-piperidinepentamide Step A 3,4-Dichloro-β-[2-[(2-methoxyphenyl)amino]-2-oxoethyl]-benzenepropanoic acid 3-(3,4-Dichlorophenyl)glutaric anhydride (10 g, Example 1, Step C) in CH₂Cl₂ (150 mL) at 0° C. was treated sequentially with o-anisidine (6 mL), triethylamine (6.7 mL) and N,N-dimethylaminopyridine (440 mg). The mixture was stirred at 0° C. for two hours then allowed to warm to room temperature and stirred for 12 hours. The reaction mixture was diluted with CH₂Cl₂ (500 mL) and washed with 1N HCl (1×200 mL) and water (1×200 mL). The organic layers were dried over MgSO₄, filtered and concentrated to afford the title compound (14 g).

Step B 3,4-Dichloro-β-[2-[(2-methoxyphenyl)methylamino)]-2-oxoethyl]-benzenepropanoic acid Sodium hydride (1.94 g, 95%) was suspended in THF (100 mL) and cooled to 0° C. 3,4-Dichloro-β-[2-[(2-methoxyphenyl)amino]-2-oxoethyl]-benzenepropanoic acid (14 g), in THF (150 mL) was added dropwise. After addition the mixture was warmed to room temperature and stirred for 12 hours. The mixture was then heated at reflux for 1 hour. The mixture was cooled to room temperature and methyl iodide (2.40 mL) was added dropwise. The resulting mixture was heated at reflux for 24 hours. Cooled to 0° C. and quenched carefully with H₂O (100 mL). Extracted with EtOAc (3×200 mL). The combine organic layers were dried over MgSO₄, filtered and concentrated under reduced pressure to give crude product. Silica gel chromatography eluting with 0–50% MeOH/CH₂Cl₂ gave the title compound (10 g).

Step C 3,4-dichloro-β-(2-hydroxyethyl)-N-(2-methoxyphenyl)-N-methylbenzenepropanamide 3,4-Dichloro-β-[2-[(2-methoxyphenyl)methylamino)]-2-oxoethyl]-benzenepropanoic acid (7.8 g) in EtOAc (100 mL) was treated with carbonyldiimidazole (3.16 g) and N,N-dimethylaminopyridine (190 mg). The resulting solution was stirred at room temperature for 15 minutes and then heated at 50° C. for two hours. The reaction mixture was cooled to 0° C. and treated with a solution of NaBH₄ (2.95 g) in H₂O (50 mL), warmed slowly to room temperature and stirred for 12 hours. The reaction mixture was diluted with EtOAc (300 mL) and washed with 1N HCl (1×200 mL), sat. NaHCO₃ (1×200 mL) and water (1×200 mL). The organic phase was dried over MgSO₄, filtered and concentrated under reduced pressure to yield the crude compound as a oil. Silica gel chromatography eluting with 0–10% MeOH/CH₂Cl₂ gave the title compound (8 g). Mass spectrum (CI): 382.

Step D 3,4-dichloro-β-N-(2-methoxyphenyl)-N-methyl-(2-oxoethyl)-benzenepropamide A solution of oxalyl chloride (1.14 mL) in CH₂Cl₂ (50 mL) was cooled to −78° C. whereupon DMSO (1.85 mL) was added dropwise over 15 mins. This mixture was stirred for 15 minutes. Whereupon a CH₂Cl₂ (10 mL) solution of 3,4-Dichloro-β-(2-hydroxyethyl)-N-(2-methoxyphenyl)-N-methylbenzenepropanamide (1.0 g) was added over 20 minutes. The mixture was stirred for 30 minutes and then treated with Et₃N (7.3 mL) and stirred for an additional 30 minutes at −78° C., followed by 1.5 hours at room temperature. The reaction mixture was quenched with water and diluted with CH₂Cl₂ (100 mL). The organic fraction was separated, washed sequentially with 1N HCl (1×50 mL), sat. NaHCO3 (1×50 mL) and brine (1×50 mL), dried over MgSO₄, filtered and concentrated under reduced pressure to yield an oil. Silica gel chromatography eluting with 5–15% EtOAc/Hex gave the title compound (950 mg).

Step E

Beta-(3,4-dichlorophenyl)-4-hydroxy-N-(2-methoxyphenyl)-N-methyl-4-phenyl-1-piperidine pentamide 3,4-dichloro-β-N-(2-methoxyphenyl)-N-methyl-(2-oxoethyl)-benzenepropamide (950 mg), in MeOH/THF (1:1, 20 mL) was treated sequentially with molecular sieves 3A (800 mg), 4-phenyl-4-hydroxypiperidine HCl (800 mg) and NaBH₃CN (156 mg). The resulting mixture was stirred at room temperature for 18 hours. The reaction mixture was with quenched with water (20 mL) and diluted with CH₂Cl₂ (50 mL). The organic layer was separated and the aqueous layer extracted with CH₂Cl₂ (3×50 mL) The combined organic layers were dried over MgSO₄, filtered and concentrated under reduced pressure to give the crude oil. Silica gel chromatography eluting with 1–2% MeOH/CH₂Cl₂ gave the title compound (720 mg). Mass spectrum (CI): 541.

EXAMPLE 32

1-[3-(3,4-dichlorophenyl)-5-(4-hydroxy-4-phenyl-1-piperidinyl)-1-oxopentyl]-1,2,3,4-tetrahydroquinoline Step A Beta-(3,4-Dichlorophenyl)-1,2,3,4-tetrahydro-delta-oxo-quinolinepentanoic acid.

3-(3,4-Dichlorophenyl)glutaric anhydride (10 g, Example 1, Step C) in CH₂Cl₂ (300 mL) at 0° C. was treated sequentially with 1,2,3,4-tetrahydroquinoline (5.6 mL), triethylamine (6.3 mL) and N,N-dimethylaminopyridine (472 mg). The mixture was stirred at 0° C. for two hours then allowed to warm to room temperature and stirred for 12 hours. The reaction mixture was diluted with CH₂Cl₂ (500 mL) and washed with 1N HCl (1×200 mL) and water (1×200 mL). The organic layers were dried over MgSO$_4$, filtered and concentrated to afford the title compound (14.3 g).

Step B

1-[3-(3,4-dichlorophenyl)-5-hydroxy-1-oxopentyl]-1,2,3,4-tetrahydroquinoline

Beta-(3,4-Dichlorophenyl)-1,2,3,4-tetrahydro-delta-oxo-quinolinepentanoic acid (14.3 g) in EtOAc (300 mL) was treated with carbonyldiimidazole (7.42 g) and N,N-dimethylaminopyridine (450 mg). The resulting solution was stirred at room temperature for 15 minutes and then heated at 50° C. for two hours. The reaction mixture was cooled to 0° C. and treated with a solution of NaBH$_4$ (5.5 g) in H$_2$O (100 mL), warmed slowly to room temperature and stirred for 12 hours. The reaction mixture was diluted with EtOAc (500 mL) and washed with 1N HCl (1×200 mL), sat. NaHCO$_3$ (1×200 mL) and water (1×200 mL). The organic phase was dried over MgSO$_4$, filtered and concentrated under reduced pressure to yield the crude compound as a oil. Silica gel chromatography eluting with 0–10% MeOH/CH$_2$Cl$_2$ gave the title compound (11.5 g). Mass spectrum (CI): 378.

Step C

1-[3-(3,4-dichlorophenyl)-1,5-dioxopentyl]-1,2,3,4-tetrahydroquinoline

A solution of oxalyl chloride (1.15 mL) in CH$_2$Cl$_2$ (30 mL) was cooled to −78° C. whereupon DMSO (1.87 mL) was added dropwise over 15 mins. This mixture was stirred for 15 minutes. Whereupon a CH$_2$Cl$_2$ (30 mL) solution of 1-[3-(3,4-dichlorophenyl)-5-hydroxy-1-oxopentyl]-1,2,3,4-tetrahydroquinoline (1.0 g) was added over 20 minutes. The mixture was stirred for 30 minutes and then treated with Et$_3$N (7.4 mL) and stirred for an additional 30 minutes at −78° C., followed by 1.5 hours at room temperature. The reaction mixture was quenched with water and diluted with CH$_2$Cl$_2$ (100 mL). The organic fraction was separated, washed sequentially with 1N HCl (1×50 mL), sat. NaHCO3 (1×50 mL) and brine (1×50 mL), dried over MgSO$_4$, filtered and concentrated under reduced pressure to yield an oil. Silica gel chromatography eluting with 5–15% EtOAc/Hex gave the title compound (900 mg).

Step E

1-[3-(3,4-dichlorophenyl)-5-(4-hydroxy-4-phenyl-1-piperidinyl)-1-oxopentyl]-1,2,3,4-tetrahydroquinoline 1-[3-(3,4-dichlorophenyl)-1,5-dioxopentyl]-1,2,3,4-tetrahydroquinoline (900 mg), in MeOH/THF (1:1, 20 mL) was treated sequentially with molecular sieves 3A (767 mg), 4-phenyl-4-hydroxypiperidine HCl (767 mg) and NaBH$_3$CN (150 mg). The resulting mixture was stirred at room temperature for 18 hours. The reaction mixture was with quenched with water (20 mL) and diluted with CH$_2$Cl$_2$ (50 mL). The organic layer was separated and the aqueous layer extracted with CH$_2$Cl$_2$ (3×50 mL) The combined organic layers were dried over MgSO$_4$, filtered and concentrated under reduced pressure to give the crude oil. Silica gel chromatography eluting with 1–2% MeOH/CH$_2$Cl$_2$ gave the title compound (750 mg). Mass spectrum (FAB): 537.2081.

EXAMPLE 33

Beta-(3,4-Dichlorophenyl)-4-hydroxy-N-methyl-4-phenyl-N-(phenylmethyl)-1-piperidinepentamide Step A 3,4-Dichloro-beta-[2-[(phenylmethyl)methylamino]-2-oxoethyl]benzenepropanoic acid 3-(3,4-Dichlorophenyl)glutaric anhydride (5.0 g) in CH$_2$Cl$_2$ (100 mL) at 0° C. was treated sequentially with N-methyl-N-(phenylmethyl)amine (3.0 mL), triethylamine (3.36 mL) and N,N-dimethylaminopyridine (0.26)). The mixture was stirred at 0° C. for two hours then allowed to warm to room temperature and stirred for 12 hours. The reaction mixture was washed with 1N HCl (100 mL) and water (2×100 mL). The organic layers were dried over MgSO$_4$, filtered and concentrated to afford the title compound (6.9 g).

Step B 3,4-Dichloro-beta-(2-hydroxyethyl)-N-methyl-N-(phenylmethyl)benzenepropanamide 3,4-Dichloro-beta-[2-[(phenylmethyl)methylamino]-2-oxoethyl]benzenepropanoic acid (6.9 g) in EtOAc (150 mL) was treated with carbonyldiimidazole (4.4 g) and N,N-dimethylaminopyridine (0.22 g). The resulting solution was stirred at room temperature for 15 minutes and then heated at 50° C. for 1 hour. The reaction mixture was cooled to 0° C. and treated with a solution of NaBH$_4$ (4.46 g) in H$_2$O (75 mL), warmed slowly to room temperature and stirred for 12 hours. The reaction mixture was then diluted with EtOAc (250 mL) and washed with 1N HCl (250 mL), H$_2$O (250 mL) and dried over MgSO$_4$, filtered and concentrated under reduced pressure to yield the title compound (6.29 g).

Step C 3,4-Dichloro-beta-(2-oxoethyl)-N-methyl-N-(phenylmethyl)benzenepropanamide Oxalyl chloride (1.11 mL) in CH$_2$Cl$_2$ (10 mL) was added to a −78° C. solution of DMSO (1.8 mL) in CH$_2$Cl$_2$ (75 mL) over 15 minutes. This mixture was stirred for 15 minutes whereupon a CH$_2$Cl$_2$ (20 mL) solution of 3,4-Dichloro-beta-(2-hydroxyethyl)-N-methyl-N-$^a$phenylmethyl)benzenepropanamide (3.72 g) was added dropwise. The mixture was stirred for 30 minutes and then treated with a solution of Et$_3$N (4.24 mL) in CH$_2$Cl$_2$ (10 mL) and stirred for an additional 30 minutes at −78° C., then allowed to warm to ambient temperature overnight. The reaction mixture was washed with water (100 mL), the organic fraction separated, dried over MgSO$_4$, filtered and concentrated under reduced pressure to yield an oil (4.3 g). Silica gel chromatography eluting with 1:1/EtOAc:Hex gave the title compound (3.09 g).

Step D

Beta-(3,4-Dichlorophenyl)-4-hydroxy-N-methyl-4-phenyl-N-(phenylmethyl)-1-piperidine pentamide 3,4-Dichloro-beta-(2-oxoethyl)-N-methyl-N-(phenylmethyl)benzenepropanamide (1.21 g), in MeOH (10 mL) was treated sequentially with molecular sieves 3A (0.5 g), 4-phenyl-4-hydroxypiperidine HCl (0.92 g) and NaBH$_3$CN (0.88 g). The resulting mixture was stirred at room temperature for 18 hours. The reaction mixture was treated with satd. NaHCO$_3$ solution (10 mL) and concentrated under reduced pressure. The residue was partitioned between H$_2$O (50 mL) and CH$_2$Cl$_2$ (100 mL) The organic layer was separated and dried over Na$_2$SO$_4$, filtered and concentrated under reduced pressure to give the title compound (0.77 g). Mass spectrum (CI): 525.

EXAMPLE 34

1-[3-(3,4-Dichlorophenyl)-5-[methyl(phenylmethyl)amino]pentyl]-4-phenyl-4-piperidinol Beta-(3,4-Dichlorophenyl)-4-hydroxy-N-methyl-4-phenyl-N-(phenylmethyl)-1-piperidine pentamide (0.474 g) in THF (50 mL) was treated with BH$_3$:DMS (0.451 mL; 10M) and heated at reflux temperature for 18 hours. The cooled reaction mixture was then treated with MeOH (2.0 mL) and the solvent evaporated under reduced pressure. The residue was dissolved in EtOH (25 mL), treated with potassium carbonate (0.25 g) and heated at reflux temperature for 3 hours. The reaction mixture was concentrated under reduced pressure and partitioned between $CH_2Cl_2$ (100 mL) and saturated $NaHCO_3$ solution (100 mL). The organic portion was separated and the aqueous rextracted with $CH_2Cl_2$ (2×50 mL). The combined organic was dried over $MgSO_4$, filtered and evaporated to give an oily solid. Silica gel chromatography eluting with 10% MeOH:$CH_2Cl_2$ gave the title compound (0.40 g). Mass spectrum (FAB): 511.4.

EXAMPLE 35

2-[3-(3,4-Dichlorophenyl)-5-(4-hydroxy-4-phenyl-1-piperidinyl)-1-oxopentyl]-1,2,3,4-tetrahydroisoquinoline Step A Beta-(3,4-Dichlorophenyl)-1,2,3,4-tetrahydro-delta-oxo-isoquinolinepentanoic acid.

3-(3,4-Dichlorophenyl)glutaric anhydride (10 g, Example 1, Step C) in $CH_2Cl_2$ (300 mL) at 0° C. was treated sequentially with 1,2,3,4-tetrahydroisoquinoline (6.0 mL), triethylamine (6.7 mL) and N,N-dimethylaminopyridine (472 mg). The mixture was stirred at 0° C. for two hours then allowed to warm to room temperature and stirred for 12 hours. The reaction mixture was diluted with $CH_2Cl_2$ (500 mL) and washed with 1N HCl (1×200 mL) and water (1×200 mL). The organic layers were dried over $MgSO_4$, filtered and concentrated to afford the title compound (14 g).

Step B

2-[3-(3,4-dichlorophenyl)-5-hydroxy-1-oxopentyl]-1,2,3,4-tetrahydroisoquinoline

Beta-(3,4-Dichlorophenyl)-1,2,3,4-tetrahydro-delta-oxo-isoquinolinepentanoic acid, (14 g) in EtOAc (300 mL) was treated with carbonyldiimidazole (7.25 g) and N,N-dimethylaminopyridine (440 mg). The resulting solution was stirred at room temperature for 15 minutes and then heated at 50° C. for two hours. The reaction mixture was cooled to 0° C. and treated with a solution of $NaBH_4$ (6.7 g) in $H_2O$ (150 mL), warmed slowly to room temperature and stirred for 12 hours. The reaction mixture was diluted with EtOAc (500 mL) and washed with 1N HCl (1×200 mL), sat. $NaHCO_3$ (1×200 mL) and water (1×200 mL). The organic phase was dried over $MgSO_4$, filtered and concentrated under reduced pressure to yield the crude compound as a oil. Silica gel chromatography eluting with 0–10% MeOH/$CH_2Cl_2$ gave the title compound (12.4 g). Mass spectrum (CI): 378.

Step C

2-[3-(3,4-dichlorophenyl)-1,5-dioxopentyl]-1,2,3,4-tetrahydroisoquinoline

A solution of oxalyl chloride (0.460 mL) in $CH_2Cl_2$ (20 mL) was cooled to -78° C. whereupon DMSO (0.749 mL) was added dropwise over 15 mins. This mixture was stirred for 15 minutes. Whereupon a $CH_2Cl_2$ (10 mL) solution of 2-[3-(3,4-dichlorophenyl)-5-hydroxy-1-oxopentyl]-1,2,3,4-tetrahydroisoquinoline (1.0 g) was added over 20 minutes. The mixture was stirred for 30 minutes and then treated with $Et_3N$ (3 mL) and stirred for an additional 30 minutes at -78° C., followed by 1.5 hours at room temperature. The reaction mixture was quenched with water and diluted with $CH_2Cl_2$ (100 mL). The organic fraction was separated, washed sequentially with 1N HCl (1×50 mL), sat. NaHCO3 (1×50 mL) and brine (1×50 mL), dried over $MgSO_4$, filtered and concentrated under reduced pressure to yield an oil. Silica gel chromatography eluting with 5–15% EtOAc/Hex gave the title compound (800 mg).

Step E

2-[3-(3,4-dichlorophenyl)-5-(4-hydroxy-4-phenyl-1-piperidinyl)-1-oxopentyl]-1,2,3,4-tetrahydroisoquinoline 2-[3-(3,4-dichlorophenyl)-1,5-dioxopentyl]-1,2,3,4-tetrahydroisoquinoline (800 mg), in MeOH/THF (1:1, 20 mL) was treated sequentially with molecular sieves 3A (900 mg), 4-phenyl-4-hydroxypiperidine HCl (900 mg) and $NaBH_3CN$ (130 mg). The resulting mixture was stirred at room temperature for 18 hours. The reaction mixture was with quenched with water (20 mL) and diluted with $CH_2Cl_2$ (50 mL). The organic layer was separated and the aqueous layer extracted with $CH_2Cl_2$ (3×50 mL) The combined organic layers were dried over $MgSO_4$, filtered and concentrated under reduced pressure to give the crude oil. Silica gel chromatography eluting with 1–2% MeOH/$CH_2Cl_2$ gave the title compound (810 mg). Mass spectrum (FAB): 537.2075.

EXAMPLE 36

Beta-(3,4-Dichlorophenyl)-4-hydroxy-N-[(3-methoxyphenyl)methyl]-N-methyl-4-phenyl-1-piperidinepentamide Step A 3,4-Dichloro-beta-[2-[[(3-methoxyphenyl)methyl]methylamino]-2-oxoethyl]benzenepropanoic acid 3-(3,4-Dichlorophenyl)glutaric anhydride (6.7 g) in $CH_2Cl_2$ (100 mL) at 0° C. was treated sequentially with N-methyl-N-[3-methoxyphenyl)methyl]amine (4.7 g), triethylamine (3.27 g) and N,N-dimethylaminopyridine (0.32) ). The mixture was stirred at 0° C. for two hours then allowed to warm to room temperature and stirred for 20 hours. The reaction mixture was washed with 1N HCl (75 mL) and water (2×75 mL). The organic layers were dried over $MgSO_4$, filtered and concentrated to afford the title compound (10.5 g).

Step B 3,4-Dichloro-beta-(2-hydroxyethyl)-N-methyl-N-[(3-methoxyphenyl)methyl]benzenepropanamide 33,4-Dichloro-beta-[2-[[(3-methoxyphenyl)methyl]methylamino]-2-oxoethyl]benzenepropanoic acid (10.5 g) in EtOAc (150 mL) was treated with carbonyldiimidazole (6.22 g) and N,N-dimethylaminopyridine (0.3 g). The resulting solution was stirred at room temperature for 15 minutes and then heated at 50° C. for 1 hour. The reaction mixture was cooled to 0° C. and treated with a solution of $NaBH_4$ (6.3 g) in $H_2O$ (75 mL), warmed slowly to room temperature and stirred for 12 hours. The reaction mixture was then diluted with EtOAc (250 mL) and washed with 1N HCl (250 mL), $H_2O$ (250 mL) and dried over $MgSO_4$, filtered and concentrated under reduced pressure to yield a crude oil (13 g). Silica gel chromatography eluting with 5% MeOH/$CH_2Cl_2$ gave the title compound (9.35 g).

Step C 3,4-Dichloro-beta-(2-oxoethyl)-N-methyl-N-[(3-methoxyphenyl)methyl]benzenepropanamide Oxalyl chloride (3.23 g) in $CH_2Cl_2$ (100 mL) was added to a -78° C. solution of DMSO (4.14 g) in $CH_2Cl_2$ (20 mL) over 15 mins. This mixture was stirred for 15 minutes whereupon a $CH_2Cl_2$ (30 mL) solution of 3,4-Dichloro-beta-(2-hydroxyethyl)-N-[(3-methoxyphenyl)methyl]benzenepropanamide (8.4 g) was added dropwise. The mixture was stirred for 30 minutes and then treated with a solution of Et₃N (6.43 g) in CH₂Cl₂ (30 mL) and stirred for an additional 30 minutes at -78° C., then allowed to warm to ambient temperature. The reaction mixture was washed with water (100 mL), the organic fraction separated, dried over MgSO₄, filtered and concentrated under reduced pressure to yield an oil (11 g). Silica gel chromatography eluting with 10% EtOAc/CH₂Cl₂ gave the title compound (7.75 g).

Step D

Beta-(3,4-Dichlorophenyl)-4-hydroxy-N-[(3-methoxyphenyl)methyl]-N-methyl-4-phenyl-1-piperidinepentamide 3,4-Dichloro-beta-(2-oxoethyl)-N-methyl-N-[(3-methoxyphenyl)methyl]benzenepropanamide (1.23 g), in MeOH (100 mL) was treated sequentially with molecular sieves 3A (4 g), 4-phenyl-4-hydroxypiperidine HCl (0.87 g) and NaBH₃CN (0.83 g). The resulting mixture was stirred at room temperature for 18 hours. The reaction mixture was treated with satd. NaHCO₃ solution (10 mL) and concentrated under reduced pressure. The residue was partitioned between H₂O (50 mL) and CH₂Cl₂ (100 mL) The organic layer was separated and dried over Na₂SO₄, filtered and concentrated under reduced pressure to give an oil (1.8 g). Silica gel chromatography eluting with 5% MeOH/CH₂Cl₂ gave the title compound (0.77 g). Mass spectrum (FAB): 555.

EXAMPLE 37

1-[3-(3,4-Dichlorophenyl)-5-[[3(methoxyphenyl)methyl]methylamino]pentyl]-4-phenyl-4-piperidinol Beta-(3,4-Dichlorophenyl)-4-hydroxy-N-[(3-methoxyphenyl)methyl]-N-methyl-4-phenyl-1-piperidinepentamide (0.62 g) in THF (50 mL) was treated with BH₃:DMS (0.56 mL; 10M) and heated at 50° for 18 hours. The cooled reaction mixture was then treated with MeOH (5.0 mL) and the solvent evaporated under reduced pressure. The residue was dissolved in EtOH (50 mL), treated with potassium carbonate (1.0 g) and heated at reflux temperature for 5 hours. The reaction mixture was concentrated under reduced pressure and partitioned between CH₂Cl₂ (100 mL) and H₂O (30 mL). The organic portion was separated and the aqueous rextracted with CH₂Cl₂ (2×50 mL). The combined organic was dried over MgSO₄, filtered and evaporated to give the title compound (0.6 g). Mass spectrum (FAB): 541.

EXAMPLE 38

N-[[3,5-Bis(trifluoromethyl)phenyl]methyl]-Beta-(3,4-Dichlorophenyl)-4-hydroxy-N-methyl-4-phenyl-1-piperidinepentamide Step A 3,4-Dichloro-β-[2-[[3,5-bis-(trifluoromethyl)phenylmethyl]methylamino]-2-oxoethyl]-benzenepropanoic acid 3-(3,4-Dichlorophenyl)glutaric anhydride (3.1 g, Example 1, Step C) in CH₂Cl₂ (50 mL) at 0° C. was treated sequentially with 3,5-bis-(trifluoromethyl)benzylamine (3.4 g), triethylamine (1.83 mL) and N,N-dimethylaminopyridine (150 mg). The mixture was stirred at 0° C. for two hours then allowed to warm to room temperature and stirred for 12 hours. The reaction mixture was diluted with CH₂Cl₂ (200 mL) and washed with 1N HCl (1×100 mL) and water (1×100 mL). The organic layers were dried over MgSO₄, filtered and concentrated to afford the title compound (6.1 g).

Step B

N-[[3,5-bis-(trifluoromethyl)phenyl]methyl]-3,4-dichloro-β-(2-hydroxyethyl)-N-methyl-benzenepropanamide 3,4-Dichloro-β[2-[[3,5-bis-(trifluoromethyl)phenylmethyl]methylamino]-2-oxoethyl]-benzenepropanoic acid (6.1 g) in EtOAc (75 mL) was treated with carbonyldiimidazole (2.43 g) and N,N-dimethylaminopyridine (150 mg). The resulting solution was stirred at room temperature for 15 minutes and then heated at 50° C. for two hours. The reaction mixture was cooled to 0° C. and treated with a solution of NaBH₄ (1.8 g) in H₂O (30 mL), warmed slowly to room temperature and stirred for 12 hours. The reaction mixture was diluted with EtOAc (150 mL) and washed with 1N HCl (1×100 mL), sat. NaHCO₃ (1×100 mL) and water (1×100 mL). The organic phase was dried over MgSO₄, filtered and concentrated under reduced pressure to yield the crude compound as a oil. Silica gel chromatography eluting with 0–10% MeOH/CH₂Cl₂ gave the title compound (5.7 g). Mass spectrum (FAB): 502.0791.

Step C

N-[3,5-bis-(trifluoromethyl)phenylmethyl]-3,4-dichloro-β-(2-oxoethyl)-N-methyl-benzenepropamide A mixture of N-[[3,5-bis-(trifluoromethyl)phenyl]methyl]-3,4-dichloro-β-(2-hydroxyethyl)-N-methyl-benzenepropanamide (1.0 g) and molecular sieves (4Å, 460 mg) in CH₂Cl₂ (20 mL) and was treated with TPAP (36 mg) and 4-methylmorpholine-N-oxide (460 mg) and stirred at room temperture for 2 hours. The reaction mixture was filtered through a pad of silica gel rinsed with EtOAc (100 mL) and concentrated under reduced pressure to yield an oil. Silica gel chromatography eluting with 50–75% EtOAc/Hexanes gave the desired title compound (615 mg).

Step D

N-[[3,5-bis-(trifluoromethyl)phenyl]methyl]-β-(3,4-dichlorophenyl)-4-hydroxy-N-methyl-4-phenyl-1-piperidinepentamide N-(3,5-bis-trifluoromethylphenyl)-3,4-dichloro-β-(2-oxoethyl)-N-methyl-benzenepropamide (615 mg), in MeOH/THF (1:1, 15 mL) was treated sequentially with molecular sieves 3A (525 mg), 4-phenyl-4-hydroxypiperidine HCl (525 mg) and NaBH₃CN (104 mg). The resulting mixture was stirred at room temperature for 18 hours. The reaction mixture was with quenched with water (20 mL) and diluted with CH₂Cl₂ (50 mL). The organic layer was separated and the aqueous layer extracted with CH₂Cl₂ (3×50 mL) The combined organic layers were dried over MgSO₄, filtered and concentrated under reduced pressure to give the crude oil. Silica gel chromatography eluting with 1–2% MeOH/CH₂Cl₂ gave the title compound (500 mg). Mass spectrum (FAB): 661.1811.

EXAMPLE 89

Beta-(3,4-Dichlorophenyl)-N-[(3,5-dimethoxyphenyl)methyl]-4-hydroxy-N-methyl-4-phenyl-1-piperidinepentamide Step A 3,4-Dichloro-beta-[2-[[(3,5-dimethoxyphenyl)methyl]methylamino]-2-oxoethyl]benzenepropanoic acid 3-(3,4-Dichlorophenyl)glutaric anhydride (6.45 g) in CH₂Cl₂ (60 mL) at 0° C. was treated sequentially with N-methyl-N-[3,5-dimethoxyphenyl)methyl]amine (5.4 g), triethylamine (3.14 g) and N,N-dimethylaminopyridine (0.3 g)). The mixture was stirred at 0° C. for two hours then allowed to warm to room temperature and stirred for 20 hours. The reaction mixture was washed with 1N HCl (100 mL) and water (2×100 mL). The organic layers were dried over MgSO$_4$, filtered and concentrated to afford the title compound (11.0 g).

Step B 3,4-Dichloro-beta-(2-hydroxyethyl)-N-methyl-N-[(3,5-dimethoxyphenyl)methyl]benzenepropanamide 33,4-Dichloro-beta-[2-[[(3,5-dimethoxyphenyl)methyl]methylamino]-2-oxoethyl]benzenepropanoic acid (11.0 g) in EtOAc (150 mL) was treated with carbonyldiimidazole (6.08 g) and N,N-dimethylaminopyridine (0.3 g). The resulting solution was stirred at room temperature for 15 minutes and then heated at 50° C. for 1 hour. The reaction mixture was cooled to 0° C. and treated with a solution of NaBH$_4$ (6.2 g) in H$_2$O (50 mL), warmed slowly to room temperature and stirred for 12 hours. The reaction mixture was then diluted with EtOAc (250 mL) and washed with 1N HCl (250 mL), H$_2$O (250 mL) and dried over MgSO$_4$, filtered and concentrated under reduced pressure to yield a crude oil (13 g). Silica gel chromatography eluting with 2.5% MeOH/CH$_2$Cl$_2$ gave the title compound (9.1 g).

Step C 3,4-Dichloro-beta-(2-oxoethyl)-N-methyl-N-[(3,5-dimethoxyphenyl)methyl]benzenepropanamide Oxalyl chloride (3.2 g) in CH$_2$Cl$_2$ (125 mL) was cooled to −78° C. and treated with a solution of DMSO (4.12 g) in CH$_2$Cl$_2$ (20 mL) over 15 minutes. This mixture was stirred for 15 minutes whereupon a CH$_2$Cl$_2$ (30 mL) solution of 3,4-Dichloro-beta-(2-hydroxyethyl)-N-[(3,5-dimethoxyphenyl)methyl]benzenepropanamide (9.0 g) was added dropwise. The mixture was stirred for 30 minutes and then treated with a solution of Et$_3$N (6.4 g) in CH$_2$Cl$_2$ (25 mL) and stirred for an additional 30 minutes at −78° C., then allowed to warm to ambient temperature. The reaction mixture was washed with water (125 mL), the organic fraction separated, dried over MgSO$_4$, filtered and concentrated under reduced pressure to yield an oil (12 g). Silica gel chromatography eluting with 10% EtOAc/CH$_2$Cl$_2$ gave the title compound (8.2 g).

Step D

Beta-(3,4-Dichlorophenyl)-N-[(3,5-dimethoxyphenyl)methyl]-4-hydroxy-N-methyl-4-phenyl-1-piperidinepentamide 3,4-Dichloro-beta-(2-oxoethyl)-N-methyl-N-[(3,5-dimethoxyphenyl)methyl]benzenepropanamide (1.5 g), in MeOH (75 mL) was treated sequentially with molecular sieves 3A (5 g), 4-phenyl-4-hydroxypiperidine HCl (0.98 g) and NaBH$_3$CN (0.94 g). The resulting mixture was stirred at room temperature for 18 hours. The reaction mixture was treated with satd. NaHCO$_3$ solution (10 mL) and concentrated under reduced pressure. The residue was partitioned between H$_2$O (50 mL) and CH$_2$Cl$_2$ (100 mL) The organic layer was separated and dried over Na$_2$SO$_4$, filtered and concentrated under reduced pressure to give an oil (2.1 g). Silica gel chromatography eluting with 5% MeOH/CH$_2$Cl$_2$ gave the title compound (1.2 g). Mass spectrum (FAB): 585.

EXAMPLE 40

Beta-(3,4-Dichlorophenyl)-N-[(3-fluoro-4-methoxyphenyl)methyl]-4-hydroxy-N-methyl-4-phenyl-1-piperidinepentamide Step A 3,4-Dichloro-beta-[2-[[(3-fluoro-4-methoxyphenyl)methyl]methylamino]-2-oxoethyl]benzenepropanoic acid 3-(3,4-Dichlorophenyl)glutaric anhydride (4.15 g) in CH$_2$Cl$_2$ (150 mL) at 0° C. was treated sequentially with N-methyl-N-[3-fluoro-4-methoxyphenyl)methyl]amine (3.25 g), triethylamine (2.0 g) and N,N-dimethylaminopyridine (0.2)). The mixture was stirred at 0° C. for two hours then allowed to warm to room temperature and stirred for 20 hours. The reaction mixture was washed with 1N HCl (75 mL) and water (2×75 mL). The organic layers were dried over MgSO$_4$, filtered and concentrated to afford the title compound (7.3 g).

Step B 3,4-Dichloro-beta-(2-hydroxyethyl)-N-methyl-N-[(3-fluoro-4-methoxyphenyl)methyl]benzenepropanamide 33,4-Dichloro-beta-[2-[[(3-fluoro-4-methoxyphenyl)methyl]methylamino]-2-oxoethyl]benzenepropanoic acid (7.3 g) in EtOAc (150 mL) was treated with carbonyldiimidazole (4.15 g) and N,N-dimethylaminopyridine (0.21 g). The resulting solution was stirred at room temperature for 15 minutes and then heated at 50° C. for 1 hour. The reaction mixture was cooled to 0° C. and treated with a solution of NaBH$_4$ (4.2 g) in H$_2$O (70 mL), warmed slowly to room temperature and stirred for 12 hours. The reaction mixture was then diluted with EtOAc (250 mL) and washed with 1N HCl (250 mL), H$_2$O (250 mL) and dried over MgSO$_4$, filtered and concentrated under reduced pressure to yield a crude oil (12 g). Silica gel chromatography eluting with 2.5% MeOH/CH$_2$Cl$_2$ gave the title compound (6.35 g).

Step C 3,4-Dichloro-β-(2-oxoethyl)-N-methyl-N-[(3-methoxyphenyl)methyl]benzenepropanamide Oxalyl chloride (1.44 g) in CH$_2$Cl$_2$ (100 mL) was cooled to a −78° C. and treated with a solution of DMSO (1.84 g) in CH$_2$Cl$_2$ (20 mL) over 15 mins. This mixture was stirred for 15 minutes whereupon a CH$_2$Cl$_2$ (30 mL) solution of 3,4-Dichloro-beta-(2-hydroxyethyl)-N-[(3-fluoro-4-methoxyphenyl)methyl]benzenepropanamide (3.9 g) was added dropwise. The mixture was stirred for 30 minutes and then treated with a solution of Et$_3$N (2.85 g) in CH$_2$Cl$_2$ (20 mL) and stirred for an additional 30 minutes at −78° C., then allowed to warm to ambient temperature. The reaction mixture was washed with water (100 mL), the organic fraction separated, dried over MgSO$_4$, filtered and concentrated under reduced pressure to yield an oil (5.0 g). Silica gel chromatography eluting with 10% EtOAc/CH$_2$Cl$_2$ gave the title compound (3.6 g).

Step D

Beta-(3,4-Dichlorophenyl)-N-[(3-fluoro-4-methoxyphenyl)methyl]-4-hydroxy-N-methyl-4-phenyl-1-piperidinepentamide 3,4-Dichloro-beta-(2-oxoethyl)-N-methyl-N-[(3-fluoro-4-methoxyphenyl)methyl]benzenepropanamide (1.05 g), in MeOH (50 mL) was treated sequentially with molecular sieves 3A (3 g), 4-phenyl-4-hydroxypiperidine HCl (0.71 g) and NaBH$_3$CN (0.67 g). The resulting mixture was stirred at room temperature for 18 hours. The reaction mixture was treated with satd. NaHCO$_3$ solution (10 mL) and concentrated under reduced pressure. The residue was partitioned between H₂O (50 mL) and CH₂Cl₂ (100 mL) The organic layer was separated and dried over MgSO₄, filtered and concentrated under reduced pressure to give an oil (1.2 g). Silica gel chromatography eluting with 5% MeOH/CH₂Cl₂ gave the title compound (0.92 g). Mass spectrum (FAB): 573.

EXAMPLE 41

1-[3-(3,4-Dichlorophenyl)-5-(4-hydroxy-4-phenyl-1-piperidinyl)-1-oxopentyl]-1H-indole Step A 3,4-Dichloro-beta-[[2-[1-(indolinyl)]]-2-oxoethyl]-benzenepropanoic acid.

3-(3,4-Dichlorophenyl)glutaric anhydride (10 g, Example 1, Step C) in CH₂Cl₂ (150 mL) at 0° C. was treated sequentially with indole (5.6 g), triethylamine (6.7 mL) and N,N-dimethylaminopyridine (440 mg). The mixture was stirred at 0° C. for two hours then allowed to warm to room temperature and stirred for 12 hours. The reaction mixture was diluted with CH₂Cl₂ (200 mL) and washed with 1N HCl (1×100 mL) and water (1×100 mL). The organic layers were dried over MgSO₄, filtered and concentrated to afford the title compound (14 g).

Step B

1-[3-(3,4-dichlorophenyl)-5-hydroxy-1-oxopentyl]-1H-indole 3,4-Dichloro-beta-[[2-[1-(indolinyl)]]-2-oxoethyl]-benzenepropanoic acid (14 g) in EtOAc (300 mL) was treated with 1,1'-carbonyldiimidazole (12.5 g) and N,N-dimethylaminopyridine (470 mg). The resulting solution was stirred at room temperature for 15 minutes and then heated at 50° C. for two hours. The reaction mixture was cooled to 0° C. and treated with a solution of NaBH₄ (7.3 g) in H₂O (100 mL), warmed slowly to room temperature and stirred for 12 hours. The reaction mixture was diluted with EtOAc (300 mL) and washed with 1N HCl (1×200 mL), sat. NaHCO₃ (1×200 mL) and water (1×200 mL). The organic phase was dried over MgSO₄, filtered and concentrated under reduced pressure to yield the crude compound as a oil. Silica gel chromatography eluting with 0–10% MeOH/CH₂Cl₂ gave the title compound (5.5 g)

Step C

1-[3-(3,4-dichlorophenyl)-1,5-dioxopentyl]-1H-indole

A mixture of 1-[3-(3,4-dichlorophenyl)-5-hydroxy-1-oxopentyl]-1H-indole (4.25 g) and molecular sieves (4Å, 2.75 g) in CH₂Cl₂ (40 mL) and was treated with TPAP (50 mg) and 4-methylmorpholine-N-oxide (2.75 mg) and stirred at room temperture for 2 hours. The reaction mixture was filtered through a pad of silica gel rinsed with EtOAc (100 mL) and concentrated under reduced pressure to yield an oil. Silica gel chromatography eluting with 50–75% EtOAc/Hexanes gave the desired title compound (930 mg).

Step D

1-[3-(3,4-dichlorophenyl)-5-(4-hydroxy-4-phenyl-1-piperidinyl)-1-oxopentyl]-1H -indole 1-[3-(3,4-dichlorophenyl)-1,5-dioxopentyl]-1H-indole (740 mg), in MeOH/THF (1:1, 30 mL) was treated sequentially with molecular sieves 3A (880 mg), 4-phenyl-4-hydroxypiperidine HCl (880 mg) and NaBH₃CN (130 mg). The resulting mixture was stirred at room temperature for 18 hours. The reaction mixture was with quenched with water (20 mL) and diluted with CH₂Cl₂ (50 mL). The organic layer was separated and the aqueous layer extracted with CH₂Cl₂ (3×50 mL) The combined organic layers were dried over MgSO₄, filtered and concentrated under reduced pressure to give the crude oil. Silica gel chromatography eluting with 1–2% MeOH/CH₂Cl₂ gave the title compound (600 mg). Mass spectrum (CI): 521.

EXAMPLE 42

Beta-(3,4-Dichlorophenyl)-4-hydroxy-N-[(2-methoxyphenyl)methyl]-N-methyl-4-phenyl-1-piperidinepentamide Step A 3,4-Dichloro-β-[2-[[(2-methoxyphenyl)methyl]methylamino]-2-oxoethyl]benzenepropanoic acid 3-(3,4-Dichlorophenyl)glutaric anhydride (5.9 g) in CH₂Cl₂ (80 mL) at 0° C. was treated sequentially with N-methyl-N-[2-methoxyphenyl)methyl]amine (3.8 g), triethylamine (3.5 mL) and N,N-dimethylaminopyridine (278 mg). The mixture was stirred at 0° C. for two hours then allowed to warm to room temperature and stirred for 20 hours. The reaction mixture was washed with 1N HCl (1×100 mL) and brine (1×100 mL). The organic layers were dried over MgSO₄, filtered and concentrated to afford the title compound (9.3 g).

Step B 3,4-Dichloro-β-(2-hydroxyethyl)-N-methyl-N-[(2-methoxyphenyl)methyl]benzenepropanamide 3-3,4-Dichloro-β-[2-[[(2-methoxyphenyl)methyl]methylamino]-2-oxoethyl]benzenepropanoic acid (9.3 g) in EtOAc (100 mL) was treated with 1,1'-carbonyldiimidazole (4.62 g) and N,N-dimethylaminopyridine (345 mg). The resulting solution was stirred at room temperature for 15 minutes and then heated at 50° C. for 1 hour. The reaction mixture was cooled to 0° C. and treated with a solution of NaBH₄ (3.45 g) in H₂O (50 mL), warmed slowly to room temperature and stirred for 12 hours. The reaction mixture was then diluted with EtOAc (250 mL) and washed with 1N HCl (1×100 mL), H₂O (1×100 mL) and dried over MgSO₄, filtered and concentrated under reduced pressure to yield a crude oil (13 g). Silica gel chromatography eluting with 5% MeOH/CH₂Cl₂ gave the title compound (8.7 g). Mass spectrum (FAB): 396.1124.

Step C 3,4-Dichloro-β-(2-oxoethyl)-N-methyl-N-[(2-methoxyphenyl)methyl]benzenepropanamide A solution of oxalyl chloride (1.43 mL) in CH₂Cl₂ (30 mL) was cooled to −78° C. whereupon DMSO (2.32 mL) was added dropwise over 15 mins. This mixture was stirred for 15 minutes. Whereupon a CH₂Cl₂ (20 mL) solution of 3,4-Dichloro-β-(2-hydroxyethyl)-N-methyl-N-[(2-methoxyphenyl)methyl]benzenepropanamide (1.3 g) was added over 20 minutes. The mixture was stirred for 30 minutes and then treated with Et₃N (9.2 mL) and stirred for an additional 30 minutes at −78° C., followed by 1.5 hours at room temperature. The reaction mixture was quenched with water and diluted with CH₂Cl₂ (100 mL). The organic fraction was separated, washed sequentially with 1N HCl (1×50 mL), sat. NaHCO3 (1×50 mL) and brine (1×50 mL), dried over MgSO₄, filtered and concentrated under reduced pressure to yield an oil. Silica gel chromatography eluting with 50–100% EtOAc/Hex gave the title compound (950 mg).

Step D

Beta-(3,4-Dichlorophenyl)-4-hydroxy-N-[(2-methoxyphenyl)methyl]-N-methyl-4-phenyl-1-piperidinepentamide 3,4-Dichloro-β-(2-oxoethyl)-N-methyl-N-[(2-methoxyphenyl)methyl]benzenepropanamide (950 mg), in MeOH/THF (30 mL, 1:1 ) was treated sequentially with molecular sieves 3A (770 mg), 4-phenyl-4-hydroxypiperidine HCl (770 mg) and NaBH$_3$CN (150 mg). The resulting mixture was stirred at room temperature for 18 hours. The reaction mixture was with quenched with water (20 mL) and diluted with CH$_2$Cl$_2$ (50 mL). The organic layer was separated and the aqueous layer extracted with CH$_2$Cl$_2$ (3×50 mL) The combined organic layers were dried over MgSO$_4$, filtered and concentrated under reduced pressure to give the crude oil. Silica gel chromatography eluting with 5% MeOH/CH$_2$Cl$_2$ gave the title compound (720 mg). Mass spectrum (FAB): 555.2181.

EXAMPLE 43

Beta-(3,4-Dichlorophenyl)-4-hydroxy-N-methyl-4-phenyl-N-(2-phenylethyl)-1-piperidinepentamide Step A 3,4-Dichloro-β-[2-[(2-phenylethyl)methylamino]-2-oxoethyl]benzenepropanoic acid 3-(3,4-Dichlorophenyl)glutaric anhydride (3.4 g) in CH$_2$Cl$_2$ (50 mL) at 0° C. was treated sequentially with N-methylphenethylamine (2.4 mL), triethylamine (2.3 mL) and N,N-dimethylaminopyridine (162 mg). The mixture was stirred at 0° C. for two hours then allowed to warm to room temperature and stirred for 20 hours. The reaction mixture was washed with 1N HCl (1×100 mL) and brine (1×100 mL). The organic layers were dried over MgSO$_4$, filtered and concentrated to afford the title compound (4.6 g).

Step B 3,4-Dichloro-β-(2-hydroxyethyl)-N-methyl-N-(2-phenethyl)-benzenepropanamide 3-3,4-Dichloro-β-[2-[(2-phenethyl)methylamino]-2-oxoethyl]benzenepropanoic acid (4.6 g) in EtOAc (75 mL) was treated with 1,1'-carbonyldiimidazole (2.6 g) and N,N-dimethylaminopyridine (162 mg). The resulting solution was stirred at room temperature for 15 minutes and then heated at 50° C. for 1 hour. The reaction mixture was cooled to 0° C. and treated with a solution of NaBH$_4$ (2.5 g) in H$_2$O (30 mL), warmed slowly to room temperature and stirred for 12 hours. The reaction mixture was then diluted with EtOAc (250 mL) and washed with 1N HCl (1×100 mL), H$_2$O (1×100 mL) and dried over MgSO$_4$, filtered and concentrated under reduced pressure to yield a crude oil (5 g). Silica gel chromatography eluting with 2.5% MeOH/CH$_2$Cl$_2$ gave the title compound (3.5 g). Mass spectrum (FAB): 380.1177.

Step C 3,4-Dichloro-β-(2-oxoethyl)-N-methyl-N-(2-phenethyl)-benzenepropanamide

A solution of oxalyl chloride (1.25 mL) in CH$_2$Cl$_2$ (25 mL) was cooled to −78° C. whereupon DMSO (2.03 mL) was added dropwise over 15 mins. This mixture was stirred for 15 minutes. Whereupon a CH$_2$Cl$_2$ (25 mL) solution of 3,4-Dichloro-β-(2-hydroxyethyl)-N-methyl-N-(2-phenethyl)-benzenepropanamide (1.1 g) was added over 20 minutes. The mixture was stirred for 30 minutes and then treated with Et$_3$N (9.2 mL) and stirred for an additional 30 minutes at −78° C., followed by 1.5 hours at room temperature. The reaction mixture was quenched with water and diluted with CH$_2$Cl$_2$ (100 mL). The organic fraction was separated, washed sequentially with 1N HCl (1×50 mL), sat. NaHCO3 (1×50 mL) and brine (1×50 mL), dried over MgSO$_4$, filtered and concentrated under reduced pressure to yield an oil. Silica gel chromatography eluting with 50–100% EtOAc/Hex gave the title compound (900 mg).

Step D

Beta-(3,4-Dichlorophenyl)-4-hydroxy-N-(2-phenethyl)-N-methyl-4-phenyl-1-piperidinepentamide 3,4-Dichloro-β-(2-oxoethyl)-N-methyl-N-(2-phenethyl)-benzenepropanamide (900 mg), in MeOH/THF (30 mL, 1:1) was treated sequentially with molecular sieves 3A (800 mg), 4-phenyl-4-hydroxypiperidine HCl (760 mg) and NaBH$_3$CN (150 mg). The resulting mixture was stirred at room temperature for 18 hours. The reaction mixture was with quenched with water (20 mL) and diluted with CH$_2$Cl$_2$ (50 mL). The organic layer was separated and the aqueous layer extracted with CH$_2$Cl$_2$ (3×50 mL) The combined organic layers were dried over MgSO$_4$, filtered and concentrated under reduced pressure to give the crude oil. Silica gel chromatography eluting with 1–2% MeOH/CH$_2$Cl$_2$ gave the title compound (680 mg). Mass spectrum (FAB): 539.2222.

The in vitro and in vivo activity of the compounds of formula I can be determined by the following procedures.

In vitro procedure to identify NK$_1$ activity

Test compounds are evaluated for their ability to inhibit the activity of the NK$_1$ agonist Substance P on the isolated guinea pig vas deferens. Freshly cut vas deferens are removed from male Hartley guinea pigs (230–350 g) and suspended in 25 ml tissue baths containing Kreb's Henseleit solution warmed to 37° C. and constantly aerated with 95% O$_2$ and 5% CO$_2$. Tissues are adjusted to 0.5 g and allowed to equilibrate for a period of 30 minutes. The vas deferens are exposed to an electrical field stimulation (Grass S48 Stimulator) every 60 seconds at an intensity that will cause the tissue to contract 80% of its maximum capacity. All responses are recorded isometrically by means of a Grass force displacement transducer (FT03) and Harvard electronic recorder. Substance P inhibits the electrical field stimulated-induced contractions of the guinea pig vas deferens. In unpaired studies, all tissues (control or drug treated) are exposed to cumulative concentrations of Substance P ($1 \times 10^{-10}$M–$7 \times 10^{-7}$M). Single log-concentrations of the test compounds are given to separate tissues and allowed to equilibrate for 30 minutes before a Substance P concentration-response curve is generated. At least 5 separate tissues are used for each control and individual drug-concentration for every drug assay.

Inhibition of the Substance P is demonstrated by a rightward shift of its concentration-response curve. These shifts are used to determine the pA$_2$ value, which is defined as the negative log of the molar concentration of the inhibitor which would require that twice as much agonist be used to elicit a chosen response. This value is used to determine relative antagonist potency.

Isolated Hamster Trachea NK$_2$ Assay

General methodology and characterization of hamster trachea responses to neurokinin agonists as providing an NK$_2$ monoreceptor assay is found in C. A. Maggi, et al., *Eur. J. Pharmacol.* 166 (1989) 435 and J. L. Ellis, et al., *J. Pharm. Exp. Ther.* 267 (1993) 95.

Continuous isometric tension monitoring is achieved with Grass FT-03 force displacement transducers connected to Buxco Electronics preamplifiers built into a Graphtec Linearcorder Model WR 3310.

Male Charles River LAK:LVG (SYR) hamsters, 100–200 g fed weight, are stunned by a sharp blow to the head, loss of corneal reflex is assured, the hamsters are sacrificed by thoractomy and cutting the heart. Cervical trachea segments are removed to room temperature Krebs buffer, pH 7.4, aerated with 95% O$_2$–5% CO$_2$ gas and cleaned of adhering tissue. The segments are cut into two 3–4 mm long ring segments. Tracheal rings are suspended from transducers and anchored in 15.0 ml water jacketed organ baths by means of stainless steel hooks and 6-0 silk. Baths are filled with Krebs buffer, pH 7.4, maintained at 37° C. and continuously aerated with 95% $O_2$–5% $CO_2$ gas. Tracheal rings are placed under 1.0 g initial tension and allowed a 90 min equilibration period with four 1 μM NKA challenge, wash and recovery cycles at 20 min intervals. 30 min vehicle pretreatment is followed by cumulative additions of rising doses of NKA (3 nM–1 μM final concentration, 5 min intervals between additions). The final NKA response is followed by a 15 min wash and recovery period. 30 min pretreatment with a test compound or its vehicle is followed by cumulative additions of rising doses of NKA (3 nM–10 μM final concentration if necessary, 5 min intervals between additions). The final NKA response is followed by a 1 mM carbachol challenge to obtain a maximal tension response in each tissue.

Tissue responses to NKA are recorded as positive pen displacements over baseline and converted to grams tension by comparison to standard weights. Responses are normalized as a % of the maximal tissue tension. $ED_{50}$'s are calculated for NKA from the control and treated NKA dose responses and compared. Test compounds resulting in an agonist dose ratio $\geq 2$ at a screening concentration of 1 μM (i.e. $pA_{2\geq}=6.0$) are considered actives. Further dose response data is obtained for actives so that an apparent $pA_2$ estimate can be calculated. $pA_2$ is calculated either by estimation of $K_i$ as described by Furchgott (where $pA_2$=−Log $K_i$, R. F. Furchgott, *Pharm. Rev.* 7 [1995] 183) or by Shild Plot Analysis (O. Arunlakshana & H. O. Shild, Br. *J. Pharmacol.* 14 [1959] 48) if the data is sufficient.

Effect of $NK_1$ Antagonists on Substance P-Induced Airway Microvascular Leakage in Guinea Pigs Studies are performed on male Hartley guinea pigs ranging in weight from 400–650 g. The animals are given food and water ad libitum. The animals are anesthetized by intraperitoneal injection of dialurethane (containing 0.1 g/ml diallylbarbituric acid, 0.4 g/ml ethylurea and 0.4 g/ml urethane). The trachea is cannulated just below the larynx and the animals are ventilated ($V_T$=4 ml, f=45 breaths/min) with a Harvard rodent respirator. The jugular vein is cannulated for the injection of drugs.

The Evans blue dye technique (Danko, G. et al., *Pharmacol. Commun.*, 1, 203–209, 1992) is used to measure airway microvascular leakage (AML). Evans blue (30 mg/kg) is injected intravenously, followed 1 min later by i.v. injection of substance P (10 μg/kg). Five min later, the thorax is opended and a blunt-ended 13-gauge needle passed into the aorta. An incision is made in the right atrium and blood is expelled by flushing 100 ml of saline through the aortic catheter. The lungs and trachea are removed en-bloc and the trachea and bronchi are then blotted dry with filter paper and weighed. Evans blue is extracted by incubation of the tissue at 37° C. for 18 hr in 2 ml of formamide in stoppered tubes. The absorbance of the formamide extracts of dye is measured at 620 nm. The amount of dye is calculated by interpolation from a standard curve of Evans blue in the range 0.5–10 μg/ml in formamide. The dye concentration is expressed as ng dye per mg tissue wet weight. Test compounds were suspended in cyclodextran vehicle and given i.v. 5 min before substance P.

Measurement of $NK_2$ Activity In Vivo

Male Hartley guinea pigs (400–500 gm) with ad lib. access to food and water are anesthetized with an intraperitoneal injection of 0.9 ml/kg dialurethane (containing 0.1 g/m diallylbarbituric acid, 0.4 g/ml ethylurea and 0.4 g/ml urethane). After induction of a surgical plane of anesthesia, tracheal, esophageal and jugular venous cannulae are implanted to facilitate mechanical respiration, measurement of esophageal pressure and administration of drugs, respectively.

The guinea pigs are placed inside a whole body plethysmograph and the catheters connected to outlet ports in the plethysmograph wall. Airflow is measured using a differential pressure transducer (Validyne, Northridge Calif., model MP45-1, range ±2 cm $H_2O$) which measures the pressure across a wire mesh screen that covers a 1 inch hole in the wall of the plethysmograph. The airflow signal is electrically integrated to a signal proportional to volume. Transpulmonary pressure is measured as the pressure difference between the trachea and the esophagus using a differential pressure transducer (Validyne, Northridge, Calif., model MP45-1, range ±20 cm $H_2O$). The volume, airflow and transpulmonary pressure signals are monitored by means of a pulmonary analysis computer (Buxco Electronics, Sharon, Conn., model 6) and used for the derivation of pulmonary resistance (RL) and dynamic lung compliance ($C_{Dyn}$).

Bronchoconstriction Due to NKA

Increasing iv doses of NKA are administered at half log (0.01–3 μg/kg) intervals allowing recovery to baseline pulmonary mechanics between each dose. Peak bronchoconstriction occurs within 30 seconds after each dose of agonist. The dose response is stopped when $C_{Dyn}$ is reduced 80–90% from baseline. One dose-response to NKA is performed in each animal. Test compounds are suspended in cyclodextran vehicle and given i.v. 5 min before the initiation of the NKA dose response.

For each animal, dose response curves to NKA are constructed by plotting the percent increase in $R_L$ or decrease in $C_{Dyn}$ against log dose of agonist. The doses of NKA that increased $R_L$ by 100% ($R_L100$) or decreased $C_{Dyn}$ by 40% ($C_{Dyn}40$) from baseline values are obtained by log-linear interpolation of the dose response curves.

Neurokinin Receptor Binding Assay(s)

Chinese Hamster ovary (CHO) cells transfected with the coding regions for the human neurokinin 1 ($NK_1$) of the human neurokinin 2 ($NK_2$) receptors are grown in Dulbecco's minimal essential medium supplemented with 10% fetal calf serum, 0.1 mM non-essential amino acids, 2 mM glutamine, 100units/ml of penicillin and streptomycin, and 0.8 mg of G418/ml at 37° C. in a humidified atmosphere containing 5% $CO_2$.

Cells are detached from T-175 flasks with a sterile solution containing 5 mM EDTA in phosphate buffered saline. Cells are harvested by centrifugation and washed in RPMI media at 40° C. for 5 minutes. The pellet is resuspended in Tris-HCl (pH7.4) containing 1 uM phsphoramidon and 4 ug/ml of chymostatin at a cell density of 30×10⁶ cells/ml. The suspension is then homogenized in a Brinkman Polytron (setting 5) for 30–45 seconds. The homogenate is centrifuged at 800× g for 5 min at 4° C. to collect unbroken cells and nuclei. The supernatant is centrifuged in a Sorvall RC5C at 19,000 rpm (44,00× g) for 30 min at 4° C. The pellet is resuspended, an aliquot is removed for a protein determination (BCA) and washed again. The resulting pellet is stored at −80° C.

To assay receptor binding, 50 μl of [$^3$H]-Substance P (9-Sar, 11-Met [02]) (specific activity 41 Ci/mmol) (Dupont-NEN) (0.8 nM for the NK-1 assay) or [$^3$H]-Neurokinin A (specific activity 114 Ci/mmole) (Zenca) (1.0 nM for the NK-2 assay) is added to tubes containing buffer (50 mM Tris-HCl (pH 7.4) with 1 mM $MnCl_2$ and 0.2% Bovine Serum Albumin) and either DMSO or test compound. Binding is initiated by the addition of 100 μl of membrane (10–20 μg) containing the human NK-1 or NK-2 receptor in a final volume of 200 μl. After 40 minutes at room temperature, the reaction is stopped by rapid filtration onto Whatman GF/C filters which have been presoaked in 0.3% polyethylenimine. Filters are washed 2 times with 3 ml of 50 mM Tris-HCl (pH 7.4). Filters are added to 6 mls of Ready-Safe liquid scintillation cocktail and quantified by liquid scintillation spectrometry in a LKB 1219 RackBeta counter. Nonspecific binding is determined by the addition of either 1 μM of CP-99994 ($NK_1$) or 1 μM SR-48968 ($NK_2$) (both synthesized by the chemistry department of Schering-Plough Research Institute). $IC_{50}$ values are determined from competition binding curves and Ki values are determined according to Cheng and Prusoff using the experimentally determined value of 0.8 nM for the $NK_1$ receptor and 2.4 nM for the $NK_2$ receptor.

Using the test procedures described above, the following data were obtained for representative compounds of formula I:

For all of the compounds of the invention, the $NK_1$ binding is in a range of about 7–97% inhibition at 1 μM concentration. For all of the compounds of the invention, the $NK_2$ binding is in a range of about 0–90% inhibition at 1 μM concentration. It should be understood that while the $NK_2$ binding for certain compounds of the invention is as low as 0% at 1 μM concentration, that at higher concentrations these compounds may have $NK_2$ binding inhibition activity.

Activities of representative compounds of the invention in the above Neurokinin Receptor Binding Assay are as follows:

Beta-(3,4-Dichlorophenyl)-4-hydroxy-N-methyl-N,4-diphenyl-1-piperidinepentamide

Binding; $NK_1$ $K_i$=150 nM; $NK_2$ $K_i$=5.2 nM.

Beta-(3,4-Dichlorophenyl)-4-hydroxy-N-methyl-4-phenyl-N-(phenylmethyl)-1-piperidinepentamide Binding; $NK_1$ $K_i$=6.8 nM; $NK_2$ $K_i$=108 nM.

Beta-(3,4-Dichlorophenyl)-4-hydroxy-N-[(3-methoxyphenyl)methyl]-N-methyl-4-phenyl-1-piperidinepentamide Binding; $NK_1$ $K_i$=12 nM; $NK_2$ $K_i$=215 nM.

Beta-(3,4-Dichlorophenyl)-4-hydroxy-N-[(2-methoxyphenyl)methyl]-N-methyl-4-phenyl-1-piperidinepentamide Binding; $NK_1$ $K_i$=7.5 nM; $NK_2$ $K_i$=33 nM.

Beta-(3,4-Dichlorophenyl)-4-hydroxy-N-methyl-4-phenyl-N-(2-phenylethyl)-1-piperidinepentamide Binding; $NK_1$ $K_i$=70 nM; $NK_2$ $K_i$=46 nM.

The $K_i$ of a compound is that concentration at which the compound caused 50% inhibition of either $NK_1$ or $NK_2$. For those compounds of the invention having higher than 50% inhibition of $NK_1$, $K_i$'s for $NK_1$ were determined. The $K_i$'s for $NK_1$ for such compounds fell within a range of about 6.8 nM to about 215 nM.

For those compounds of the invention having higher than 50% inhibition of $NK_2$, $K_i$'s for $NK_2$ were determined. The $K_i$'s for $NK_2$ for such compounds fell within a range of about 5.2 nM to about 215 nM.

It will be recognized that compounds of formula I exhibit $NK_1$ and $NK_2$ antagonist activity to varying degrees, i.e., certain compounds have strong $NK_1$ antagonist activity, but weaker $NK_2$ antagonist activity. Others are strong $NK_2$ antagonists, but weaker $NK_1$ antagonists. While compounds with approximate equipotency are preferred, it is also within the scope of this invention to use compounds of with unequal $NK_1$/$NK_2$ antagonist activity when clinically appropriate.

Compounds of formula I have been found to be antagonists of both $NK_1$ and $NK_2$ receptors, and are therefore useful in treating conditions caused or aggravated by the activity of $NK_1$ and $NK_2$ receptors.

The present invention also relates to a pharmaceutical composition comprising a compound of formula I and a pharmaceutically acceptable carrier. Compounds of this invention can be administered in conventional oral dosage forms such as capsules, tablets, powders, cachets, suspensions or solutions, or in injectable dosage forms such as solutions, suspensions, or powders for reconstitution. The pharmaceutical compositions can be prepared with conventional excipients and additives, using well known formulation techniques. Pharmaceutically acceptable excipients and additives include nontoxic and chemically compatible fillers, binders, disintegrants, buffers, preservatives, antioxidants, lubricants, flavorings, thickeners, coloring agents, emulsifiers and the like.

The daily dose of a compound of formula I for treating asthma, cough, bronchospasm, inflammatory disease, migraine, nociception and gastrointestinal disorders is about 0.1 mg to about 20 mg/kg of body weight per day, preferably about 0.5 to about 15 mg/kg, more preferably 0.5 to about 5 mg/kg. For an average body weight of 70 kg, the dosage range is therefore from about 1 to about 1500 mg of drug per day, preferably about 50 to about 100 mg, given in a single dose or 2–4 divided doses. The exact dose, however is determined by the attending clinician, and is dependent on the potency of the compound administered, the age, weight, condition and response of the patient.

What is claimed is:
1. A compound of the formula

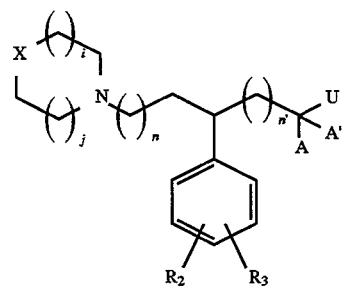

wherein each i and j is independently selected from the group consisting of 1 and 2;

each n is independently selected from the group consisting of 0, 1, 2 and 3; and each n' is independently selected from the group consisting of 1, 2 and 3;

wherein A and A' are H, or A and A' taken together are =O, =S; or =N—$R_4$;

X is selected from the group consisting O, CO, C(R, $R_1$), C=C($R_1$,$R_8$), $NR_1$, and S(O)$_e$ wherein e is 0, 1, or 2;

R is selected from the group consisting of H, $OR_8$, CON($R_8$)$_2$, CN, S(O)$_e R_8$, SO$_e$N($R_8$)$_2$, CO$_2 R_8$, and $NR_4 COR_8$;

$R_1$ is selected from the group consisting of H, ($C_1$–$C_6$)-alkyl

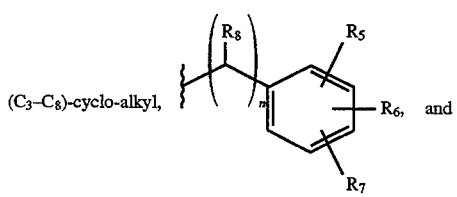

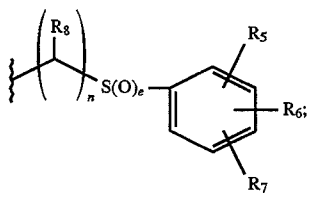

$R_2, R_3, R_5, R_6$ and $R_7$ are independently selected from the group consisting of H, halogen, $(C_1-C_6)$-alkyl, $CF_3$, $C_2F_5$, $OR_8$, $COR_8$, $CO_2R_8$, $CON(R_8, R_8)$, $N(R_8, R_8)$, $N(R_8)COR_8$, $S(O)_eR_8$, $OC(O)R_4$, $OC(O)N(R_8, R_4)$, $NR_8CO_2R_4$, $NR_8(CO)N(R_8,R_8)$, $R_{15}$-phenyl, $R_{15}$-benzyl, $NO_2$, $NR_8SO_2R_4$, $-S(O)_2N(R_8)_2$ or when $R_2$ and $R_3$ or any two of $R_5$, $R_6$ and $R_7$ are on adjacent carbons they may form a —O—$CH_2$—O— group;

each $R_4$ is independently selected from the group consisting of alkyl, substituted alkyl, substituted aryl, and substituted benzyl;

each $R_8$ is independently selected from the group consisting of H, alkyl, substituted alkyl, substituted aryl, and substituted benzyl;

each $R_{15}$ is independently H, halogen, lower alkyl, lower alkoxy; and

U is

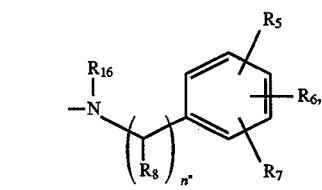 (A)

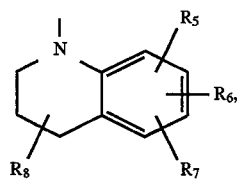 (B)

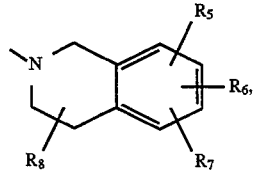 (C)

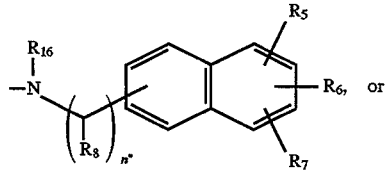 (D)

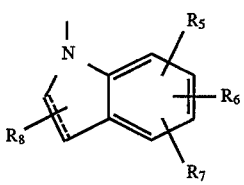 (E)

n" is independently selected from the group consisting of 0, 1, 2 and 3;

the dashed line is an optional carbon-carbon bond;

$R_{16}$ is H, $(C_1-C_6)$-alkyl, $-S(O)_2R_4$, $COR_8$, $CO_2R_4$ where $R_4$ is not H, $CON(R_8)_2$, $R_{15}$-phenyl or $R_{15}$-benzyl;

substituted means substituted with a substituent selected from the group consisting of H, $(C_1-C_6)$ alkyl, $OCF_3$, $CF_3$, and $C_2F_5$.

2. A compound according to claim 1, wherein i is 1 and j is 1.

3. A compound according to claim 1, wherein n is 1, n" is 0, 1, or 2, and n' is 1.

4. A compound according to claim 1, wherein n, n', and n" are all 1.

5. A compound according to claim 1, wherein n, and n' are both 1, and n" is 0.

6. A compound according to claim 1, wherein n, and n' are both 1, and n" is 2.

7. A compound according to claim 1, wherein A and A' are both H.

8. A compound according to claim 1, wherein A and A' taken together are =O.

9. A compound according to claim 1, wherein X is C(R, $R_1$).

10. A compound according to claim 1, wherein R is $OR_8$, $CON(R_8)_2$ CN, or $NR_4COR_4$.

11. A compound according to claim 1, wherein X is $NR_1$.

12. A compound according to claim 1, wherein $R_1$ is

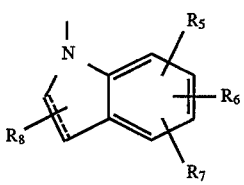

13. A compound according to claim 10, where n is 0 or 1 and $R_8$ is H.

14. A compound according to claim 10, wherein $R_2$, $R_3$, $R_5$, $R_6$ and $R_7$ are H, halogen, $C_1-C_6$ alkyl, $CF_3$, $OR_8$, $COR_8$, $CO_2R_8$, $CONR_8.R_8$, or $NR_8$, $R_8$.

15. A compound according to claim 10, wherein $R_{16}$ is H or alkyl.

16. A compound according to claim 10, wherein each R8 is selected from the group consisting of H, $C_1-C_6$ alkyl, and $R_{15}$-phenyl.

17. A compound according to claim 10, wherein $R_8$ is H or substituted alkyl.

18. A compound according to claim 10, wherein U is

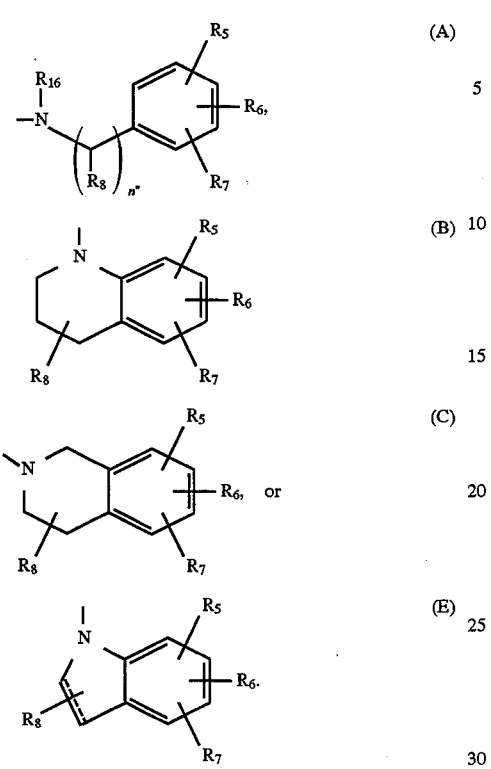

19. A method for treating chronic airway diseases; inflammatory diseases; migraine; central nervous system disorders; Down's syndrome; neuropathy; multiple sclerosis; ophthalmic disorders; conjunctivitis; auto immune disorders; graff rejection; systemic lupus erythematosus; GI disorders; disorders of bladder function; circulatory disorders; Raynaud's disease; coughing and pain which comprises administering a neurokinin antagonistic effective amount of a compound according to claim 1 to a mammal in need thereof.

20. A compound of the formula

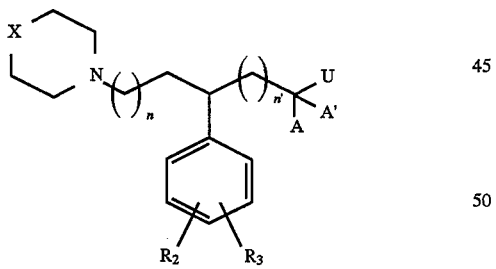

each n is independently selected from the group consisting of 0, 1, 2 and 3; and each n' is independently selected from the group consisting of 1, 2 and 3;

wherein A and A' are H, or A and A' taken together are =O, =S; or =N—$R_4$;

X is selected from the group consisting CO, C(R, $R_1$), C=C($R_1$,$R_8$);

R is selected from the group consisting of H, O$R_8$, CON($R_8$)$_2$, CN, S(O)$_e R_8$, SO$_e$N($R_8$)$_2$, CO$_2 R_8$, and N$R_4$CO$R_8$;

e is 0, 1, or 2;

$R_1$ is selected from the group consisting of H, ($C_1$–$C_6$)-alkyl

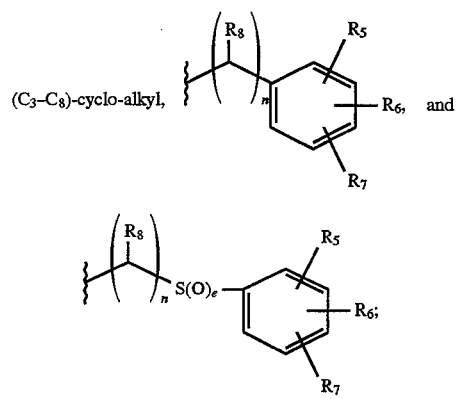

$R_2$, $R_3$, $R_5$, $R_6$ and $R_7$ are independently selected from the group consisting of H, halogen, ($C_1$–$C_6$)-alkyl, $CF_3$, $C_2F_5$, O$R_8$, CO$R_8$, CO$_2 R_8$, CON($R_8$, $R_8$), N($R_8$, $R_8$), N($R_8$)CO$R_8$, S(O)$_e R_8$, OC(O)$R_4$, OC(O)N($R_8$, $R_4$), N$R_8$CO$_2 R_4$, N$R_8$(CO)N($R_8$,$R_8$), $R_{15}$-phenyl, $R_{15}$-benzyl, NO$_2$, N$R_8$SO$_2 R_4$, —S(O)$_2$N($R_8$)$_2$ or when $R_2$ and $R_3$ or any two of $R_5$, $R_6$ and $R_7$ are on adjacent carbons they may form a —O—$CH_2$—O— group;

each $R_4$ and $R_8$ is independently selected from the group consisting of ($C_1$–$C_6$) alkyl, substituted ($C_1$–$C_6$) alkyl, substituted ($C_6$–$C_{10}$)aryl, and substituted benzyl; wherein each substituted means substituted with a substituent selected from the group consisting of H, ($C_1$–$C_6$) alkyl, OCF$_3$, CF$_3$, and $C_2F_5$;

each $R_{15}$ is independently H, halogen, ($C_1$–$C_6$) alkyl, ($C_1$–$C_6$) alkoxy; and U is

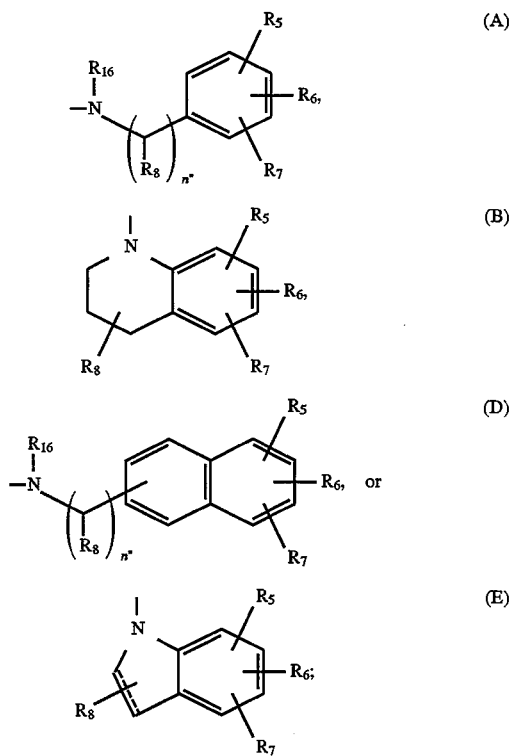

n" is independently selected from the group consisting of 0, 1,2 and 3;

the dashed line is an optional carbon-carbon bond;

$R_{16}$ is H, $(C_1-C_6)$-alkyl, $-S(O)_2R_4$, $COR_8$, $CO_2R_4$ where $R_4$ is not H, $CON(R_8)_2$, $R_{15}$-phenyl or $R_{15}$-benzyl.
21. A compound according to claim 20, selected from the group consisting of
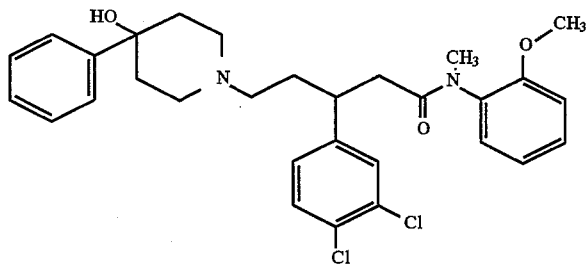
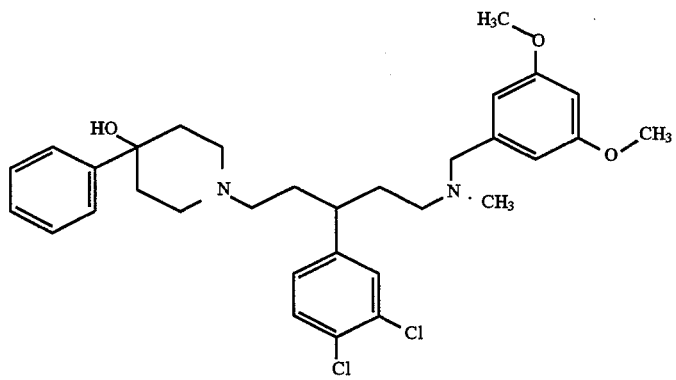
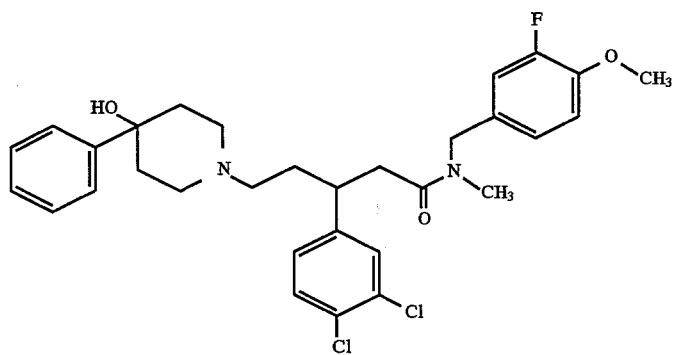
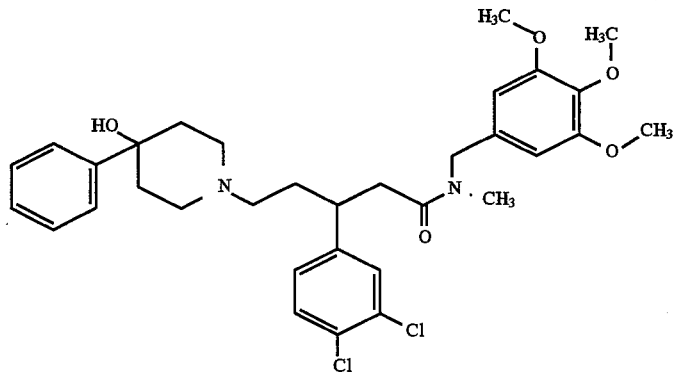

-continued
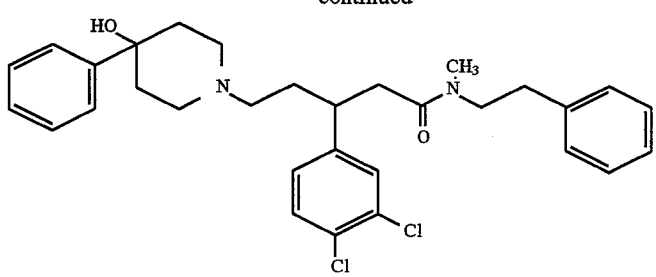
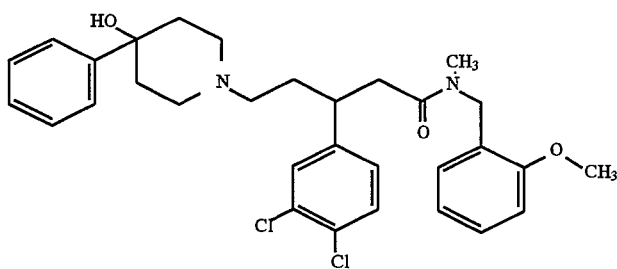
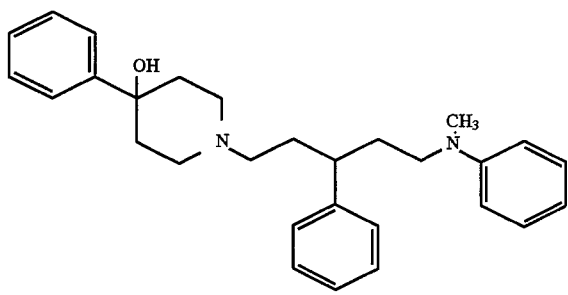
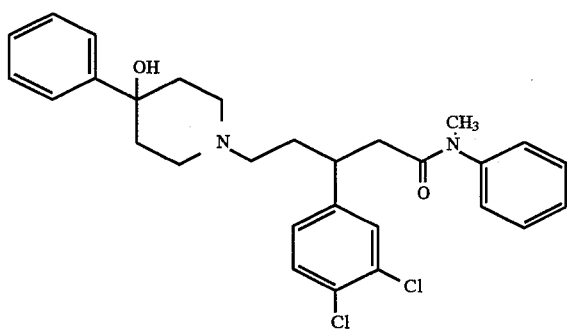
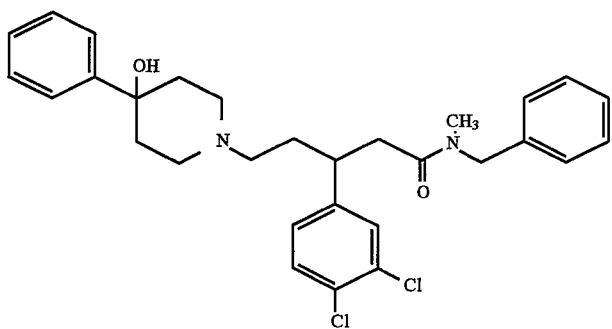

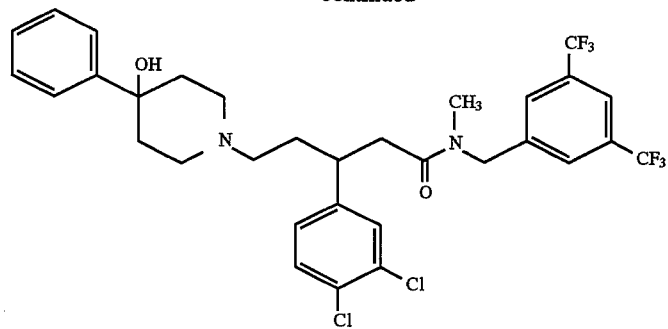
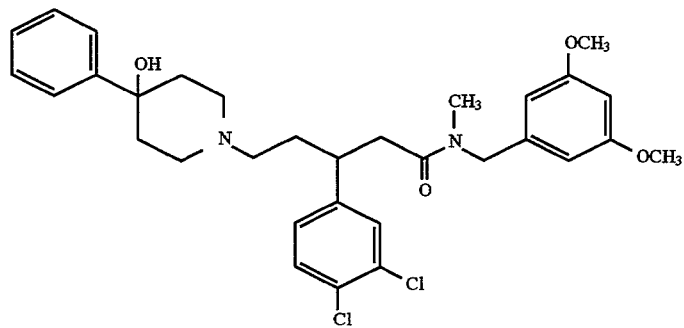
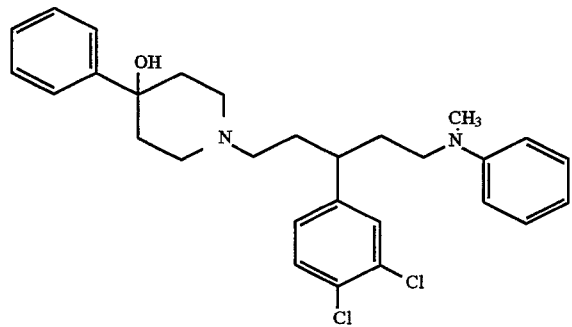
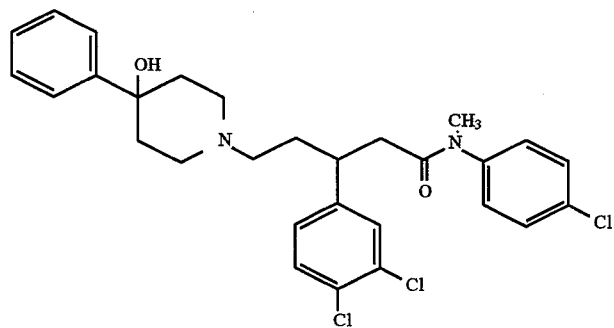
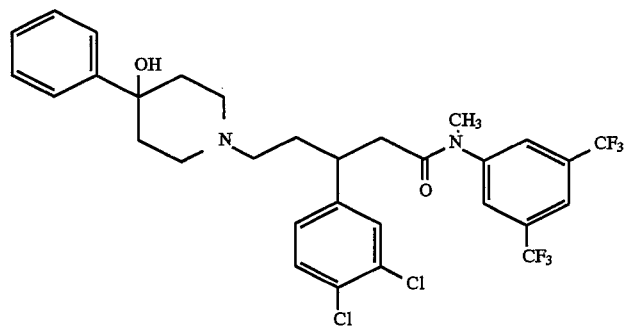

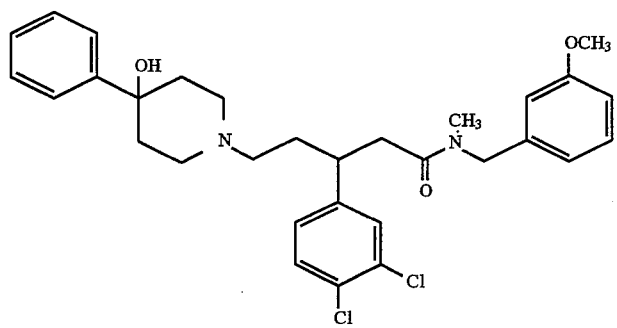
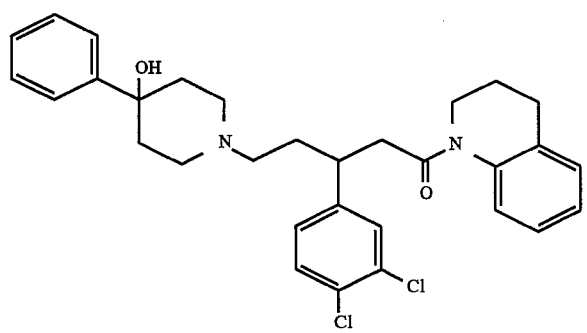
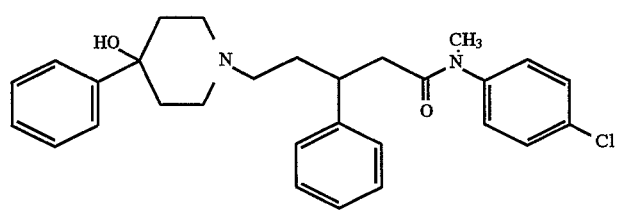
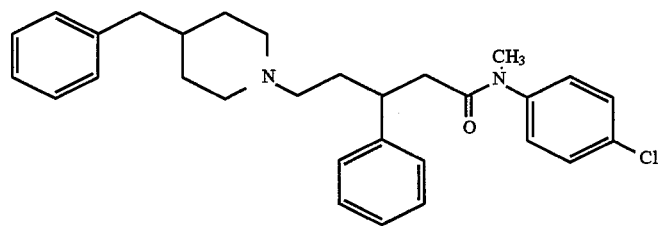
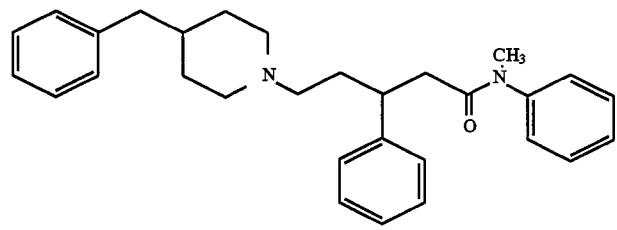
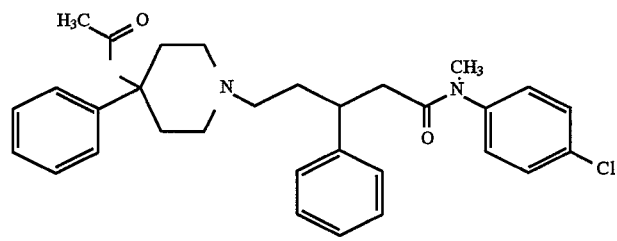

-continued
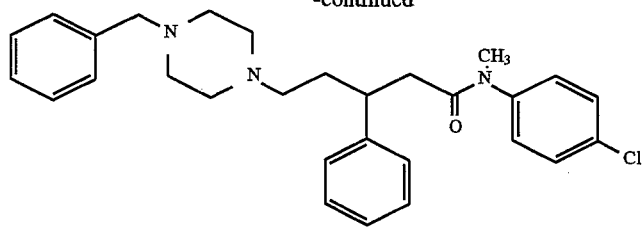
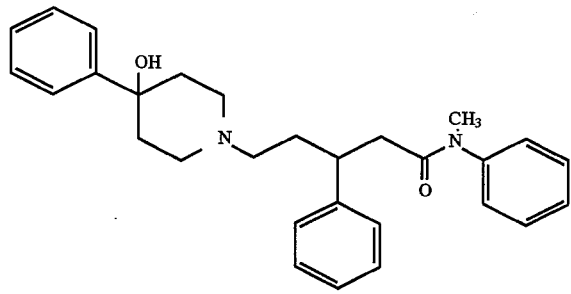
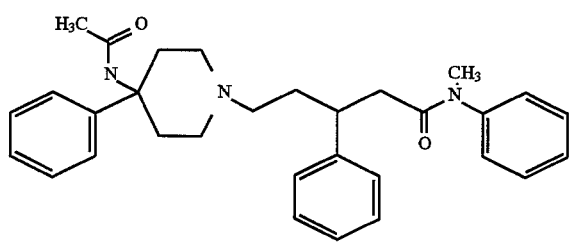
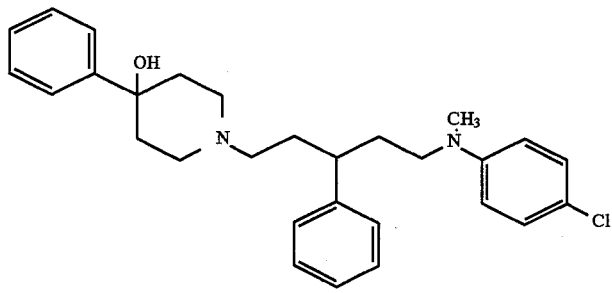
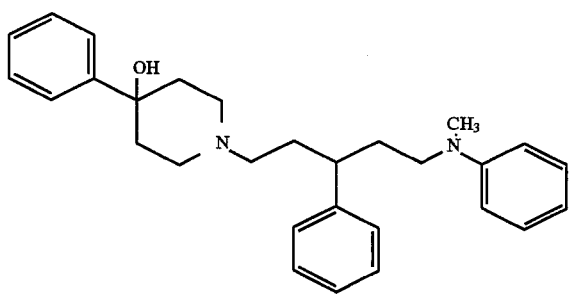
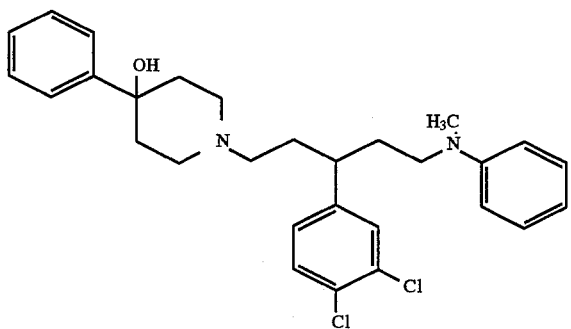

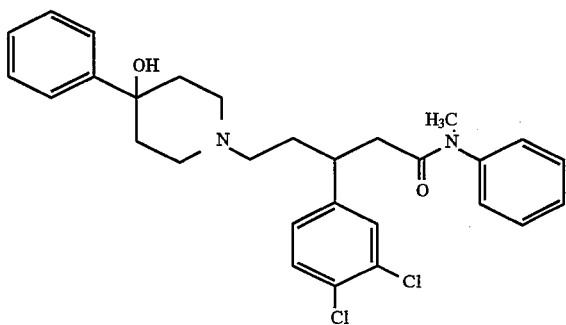
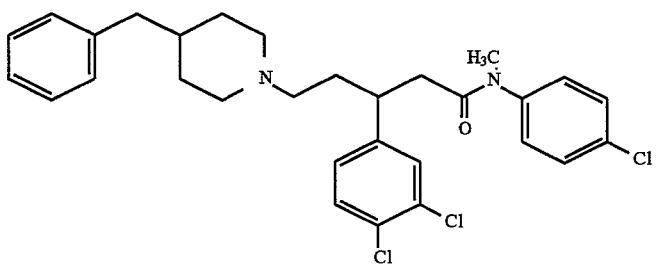
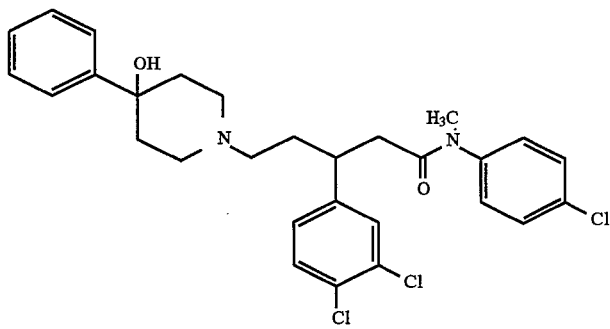
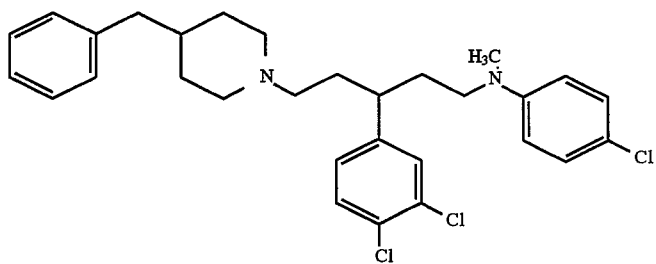
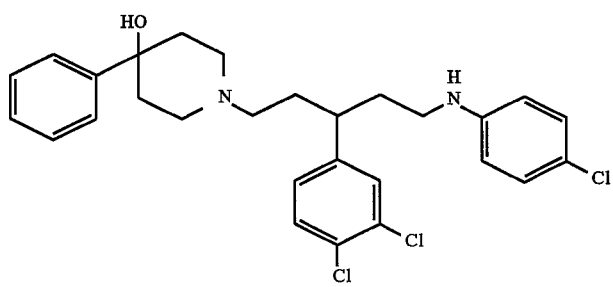

-continued
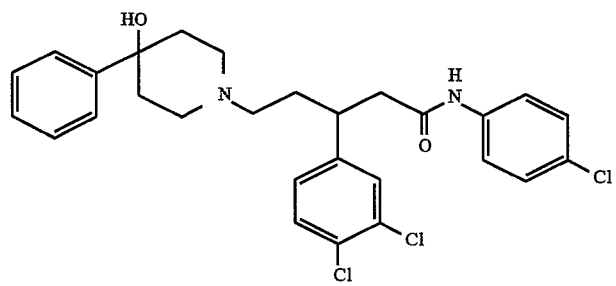
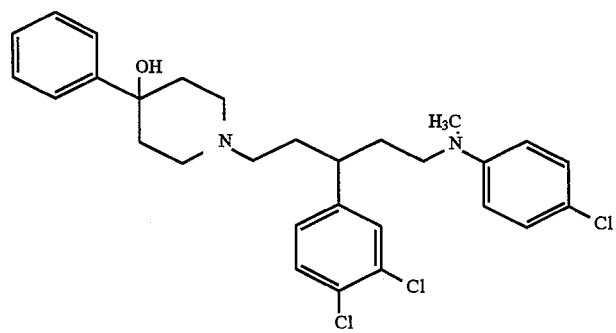
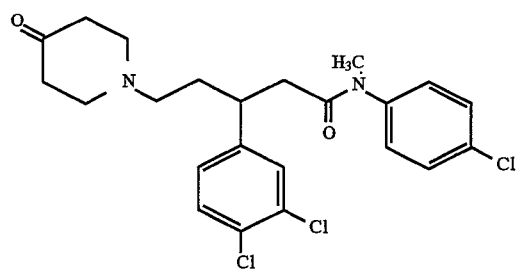
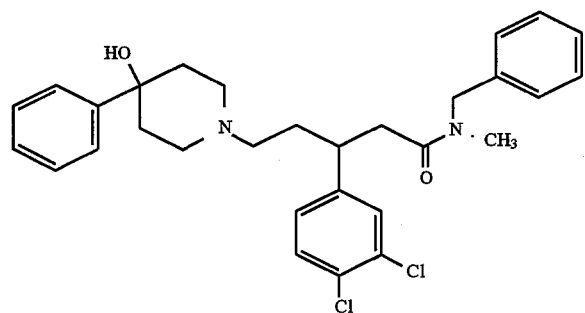
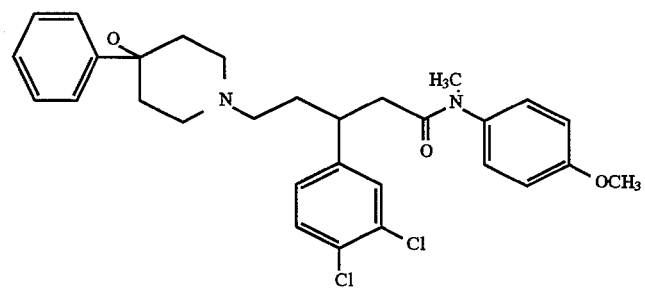

-continued
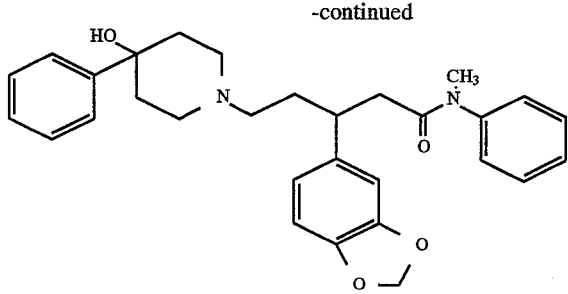
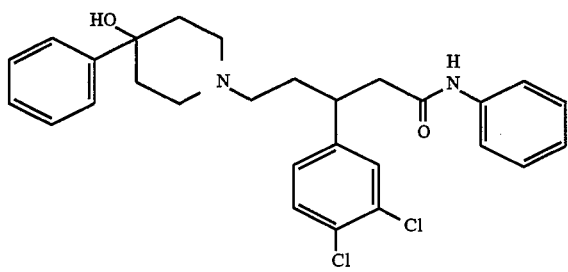
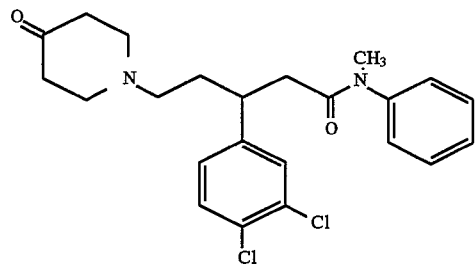
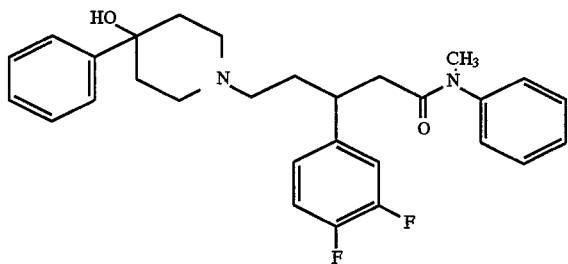
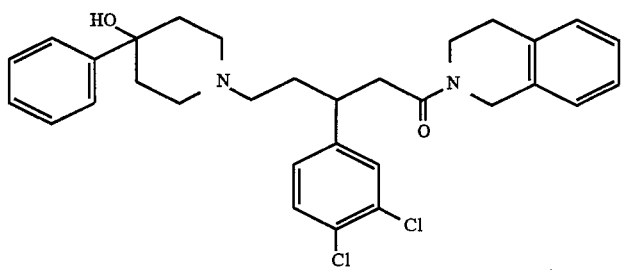
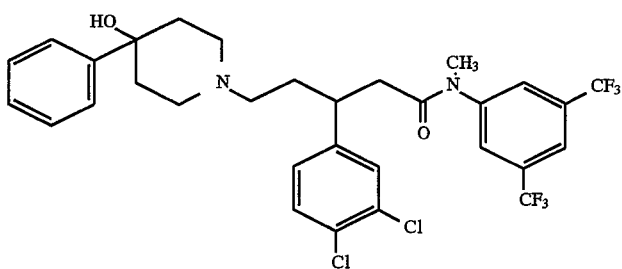

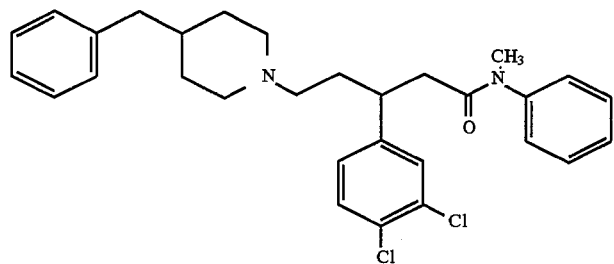
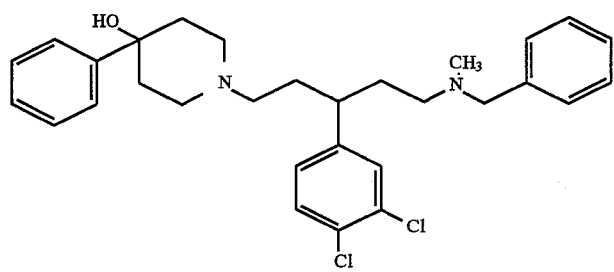
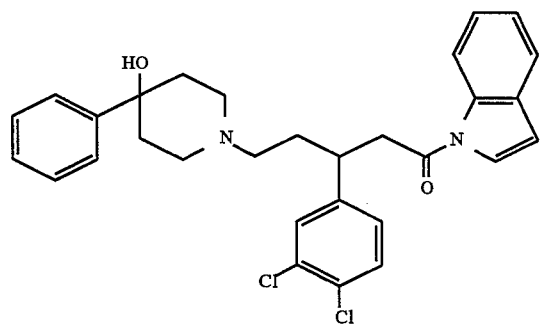
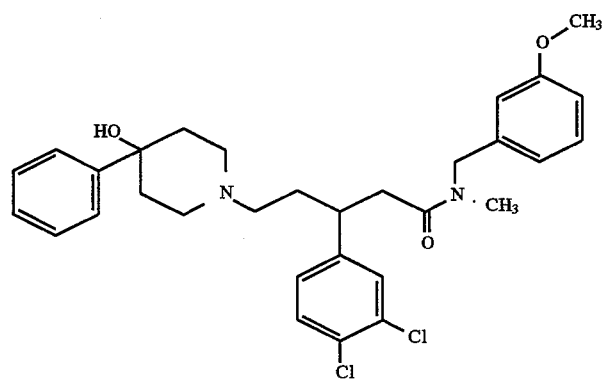
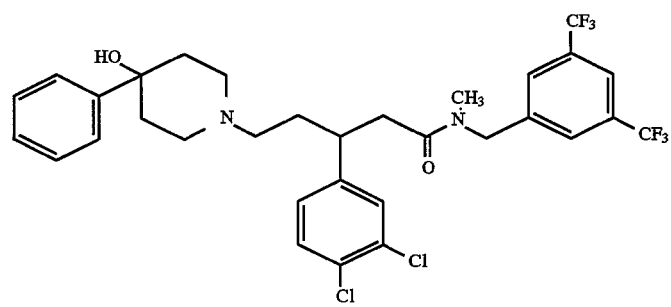

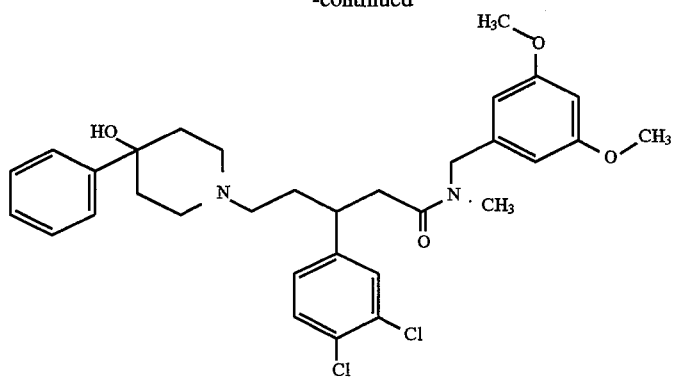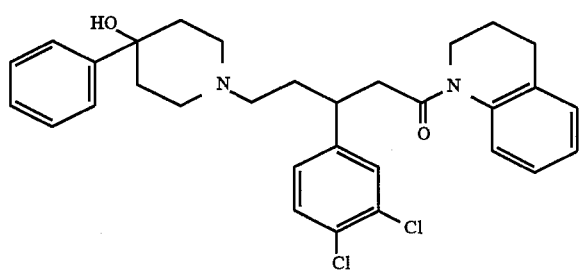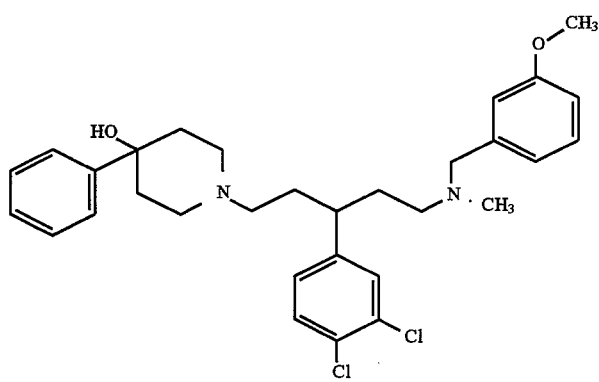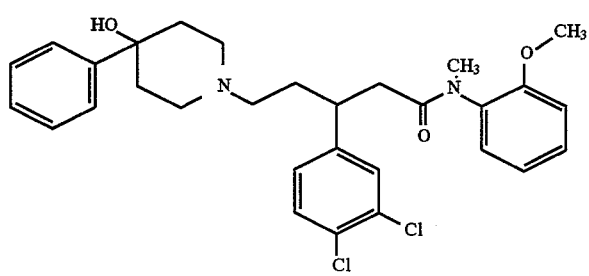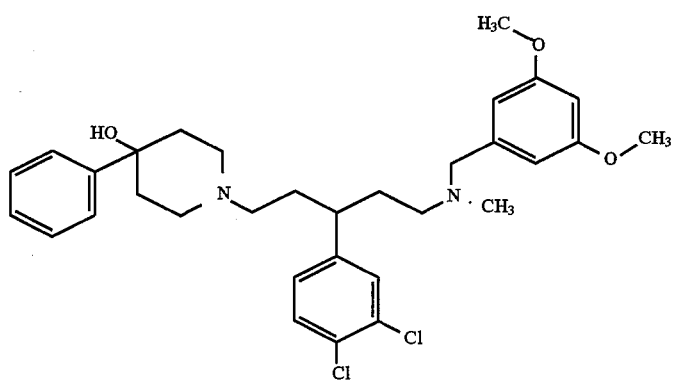

-continued

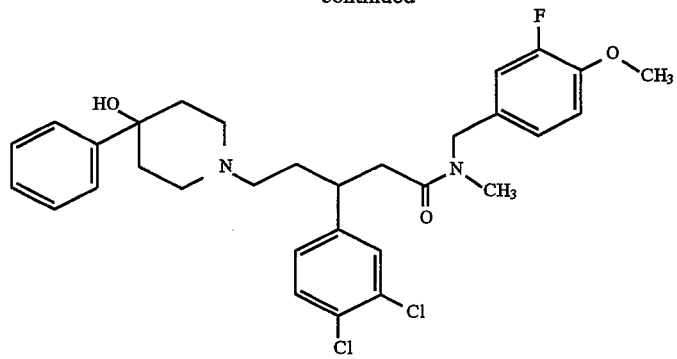

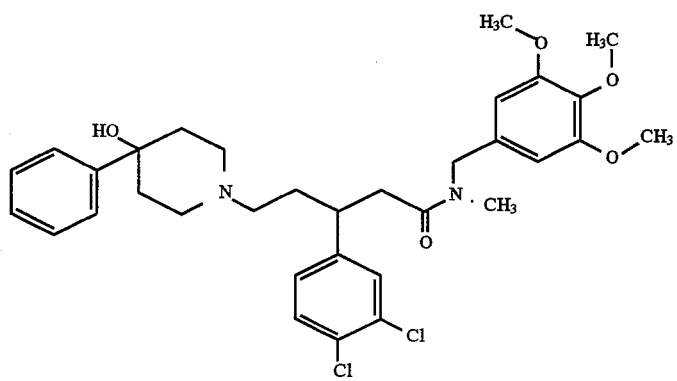

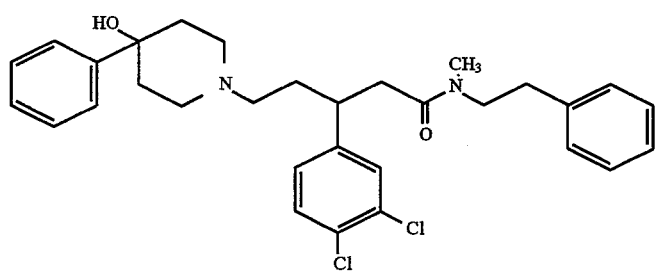

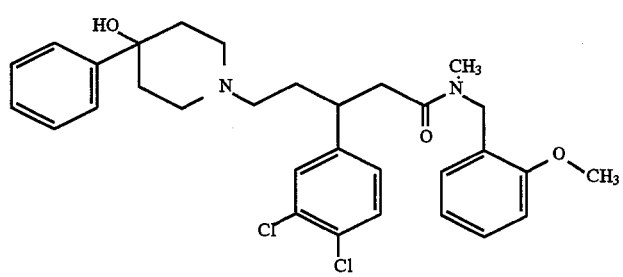

or a pharmaceutically acceptable salt thereof.

22. A composition comprising a neurokinin antagonistic effective amount of a compound according to claim 20 and a pharmaceutically acceptable carrier material.

23. A method for inducing neurokinin antagonism which comprises administering a neurokinin antagonistic effective amount of a compound according to claim 20 to a mammal in need thereof.

24. A method for treating asthma, cough, bronchospasm, inflammatory disease, migraine, nociception and gastrointestinal disorders which comprises administering a neurokinin effective amount of a compound according to claim 20 to a mammal in need thereof.

* * * * *